(12) United States Patent
Frisbee

(10) Patent No.: US 8,323,692 B2
(45) Date of Patent: *Dec. 4, 2012

(54) CONTROLLED RELEASE DOSAGE FORMS

(75) Inventor: Steven Frisbee, Reston, VA (US)

(73) Assignee: Valeant International Bermuda, Hamilton (BM)

( * ) Notice: Subject to any disclaimer, the term of this patent is extended or adjusted under 35 U.S.C. 154(b) by 37 days.

This patent is subject to a terminal disclaimer.

(21) Appl. No.: 12/328,828

(22) Filed: Dec. 5, 2008

(65) Prior Publication Data

US 2009/0142378 A1 Jun. 4, 2009

Related U.S. Application Data

(63) Continuation-in-part of application No. 10/370,109, filed on Feb. 21, 2003, now Pat. No. 7,780,987.

(60) Provisional application No. 60/357,851, filed on Feb. 21, 2002.

(51) Int. Cl.
- *A61K 9/16* (2006.01)
- *A61K 9/20* (2006.01)
- *A61K 9/28* (2006.01)
- *A61K 9/38* (2006.01)

(52) U.S. Cl. ........ 424/474; 424/464; 424/477; 424/490

(58) Field of Classification Search .................. None
See application file for complete search history.

(56) References Cited

U.S. PATENT DOCUMENTS

| | | | |
|---|---|---|---|
| 4,800,087 A | 1/1989 | Mehta | |
| 5,055,306 A * | 10/1991 | Barry et al. | 424/482 |
| 5,204,121 A | 4/1993 | Bucheler et al. | |
| 5,292,522 A | 3/1994 | Petereit et al. | |
| 5,478,573 A * | 12/1995 | Eichel et al. | 424/480 |
| 5,639,476 A | 6/1997 | Oslack et al. | |
| 5,672,359 A | 9/1997 | Digenis et al. | |
| 5,733,575 A | 3/1998 | Mehra et al. | |
| 6,022,554 A | 2/2000 | Lee et al. | |
| 6,031,004 A * | 2/2000 | Timmins et al. | 514/635 |
| 6,183,779 B1 | 2/2001 | Ouali et al. | |
| 6,340,475 B2 | 1/2002 | Shell et al. | |
| 6,475,521 B1 * | 11/2002 | Timmins et al. | 424/469 |
| 6,569,457 B2 | 5/2003 | Ullah et al. | |
| 6,620,439 B1 | 9/2003 | Mehta | |
| 6,645,527 B2 | 11/2003 | Oshlack et al. | |
| 6,676,966 B1 | 1/2004 | Odidi et al. | |
| 6,866,866 B1 | 3/2005 | Chen et al. | |
| 2002/0051818 A1 | 5/2002 | Ullah et al. | |
| 2003/0086971 A1 | 5/2003 | Kou | |
| 2003/0104049 A1 | 6/2003 | Sherman | |
| 2003/0104062 A1 | 6/2003 | Berner et al. | |
| 2003/0118647 A1 | 6/2003 | Seth | |
| 2003/0143270 A1 * | 7/2003 | Deboeck et al. | 424/468 |
| 2003/0170302 A1 | 9/2003 | Seth et al. | |
| 2003/0211154 A1 | 11/2003 | Mukherji et al. | |
| 2004/0037883 A1 | 2/2004 | Zhou et al. | |
| 2004/0058001 A1 | 3/2004 | Holzer et al. | |
| 2004/0096499 A1 | 5/2004 | Vaya et al. | |
| 2004/0096501 A1 | 5/2004 | Vaya et al. | |
| 2004/0096502 A1 | 5/2004 | Platteeuw | |
| 2004/0126428 A1 | 7/2004 | Hughes et al. | |
| 2004/0161461 A1 | 8/2004 | Seth et al. | |
| 2004/0185097 A1 | 9/2004 | Kannan et al. | |
| 2004/0241236 A1 | 12/2004 | Li et al. | |
| 2005/0019408 A1 | 1/2005 | Thumbeck et al. | |
| 2005/0025829 A1 | 2/2005 | Kim | |
| 2005/0042290 A1 | 2/2005 | Kerc et al. | |
| 2005/0048118 A1 | 3/2005 | Cucala Escoi et al. | |
| 2005/0084531 A1 | 4/2005 | Desai et al. | |
| 2005/0123596 A1 | 6/2005 | Kohane et al. | |
| 2005/0136109 A1 | 6/2005 | Rowley et al. | |
| 2005/0136111 A1 | 6/2005 | Glinecke et al. | |
| 2005/0238719 A1 | 10/2005 | Buzsaky | |
| 2007/0027213 A1 * | 2/2007 | Oberegger et al. | 514/563 |
| 2008/0075774 A1 | 3/2008 | Williams et al. | |

FOREIGN PATENT DOCUMENTS

| | | |
|---|---|---|
| DE | 198 08 634 | 3/2008 |
| EP | 0 386 440 | 9/1990 |
| EP | 1 112 738 | 7/2001 |
| JP | 01319417 | 12/1999 |
| WO | 98/27967 | 7/1998 |
| WO | 00/25756 | 5/2000 |
| WO | 0056266 | 9/2000 |
| WO | 01/49270 | 12/2001 |
| WO | 2007/078895 | 7/2007 |
| WO | 2007/143959 | 12/2007 |
| WO | 2008/064163 | 5/2008 |

* cited by examiner

*Primary Examiner* — Susan Tran

(74) *Attorney, Agent, or Firm* — Oblon, Spivak, McClelland, Maier & Neustadt, L.L.P.

(57) ABSTRACT

The invention provides stable controlled release monolithic coating compositions for use in coating pharmaceutical oral dosage forms comprising a polyglycol having a melting point greater than 55° C. and an aqueous dispersion of a neutral ester copolymer lacking functional groups.

37 Claims, No Drawings

CONTROLLED RELEASE DOSAGE FORMS

FIELD OF THE INVENTION

This invention relates to a novel monolithic film coating for obtaining controlled release of drugs from oral dosage forms.

BACKGROUND

The manner in which chemicals or drugs are administered has gained increasing attention in the past two decades. Normally, a chemical is administered in a high dose at a given time only to have to repeat that dose several hours or days later. This is not economical and sometimes results in damaging side effects. As a consequence, increasing attention has been focused on methods of giving drugs continually for prolonged time periods and in a controlled fashion. Controlled or sustained release dosage forms provide a therapeutic dose of the drug soon after administration, and then gradually release the drug over an extended period of time. The primary method of accomplishing this controlled release has been through incorporating the drugs within polymers or to surround or encapsulate a core comprising the drug with a polymer coat. Depending on the type and amount of drug, as well as the type and amount of polymer and other pharmaceutically acceptable excipients the desired controlled release profile can be obtained.

The majority of polymers used to develop coatings for controlled release dosage forms are hydrophobic and can be applied either dry, from a solution, or suspension. As most of these polymers are poorly soluble in water, they are usually applied by dissolving the polymer in an organic solvent and then sprayed onto the drug core and evaporating off the solvent. The use of organic solvents, however, is considered problematic for several reasons. The most obvious reason relates to the safety hazards associated with the use of organic solvents. Organic solvents in general are highly flammable and carcinogenic. Further, organic solvents are expensive and the storage, disposal and use of organic solvents raise environmental concerns. Accordingly, it would be desirable to prepare aqueous suspensions or solutions of controlled release coatings comprising hydrophobic polymers suitable for coating a wide variety of drug cores wherein the use of organic solvents is not required.

Eudragit® NE30D, which contains 30% solids, is one of the first aqueous polymeric dispersions used for coating pharmaceutical dosage forms. Eudragit® NE30D has many advantages over other polymers for use as a film former for obtaining a controlled release drug profile and is suited for controlled or sustained release drug formulations. The polymer forms a soft, flexible film at room temperature without any plasticizer. Also, no reactions or absorptive effects are observed when the polymer comes in direct contact with a therapeutically active agent. It is prepared by emulsion polymerization and contains neutral copolymers of ethyl acrylate-methyl methacylate esters that are insoluble over the entire physiological pH range but will still swell in water and give permeable membranes, The permeability is independent of pH and is thus suitable for the development of pH-independent modified-release oral dosage forms, provided that the solubility of the drug is also pH-independent.

One of the differences between aqueous polymeric solutions and dispersions is the role water plays during film formation. In solutions, water is a solvent and drying is accompanied by an excessive increase in viscosity, which in turn suppresses the rate of evaporation. Excess energy is therefore required to drive off the water. In contrast, in polymeric dispersions such as Eudragit® NE30D, water is only a dispersion medium and does not solvate the polymers. Consequently, less heat is needed to evaporate the water. Fast water evaporation coupled with the high solids content of the dispersion reduces processing time. These properties are even more relevant when dealing with highly water-soluble or moisture sensitive therapeutically active agents.

The pigment binding capacity of Eudragit® NE30D is very high, so that up to about 2-3 parts by weight of additives can be incorporated into 1 part by weight of dry polymer without affecting the film properties. The polymer is also compatible with a wide variety of pharmaceutical excipients.

Plasticizers are generally added to coating formulations to modify the physical properties i.e., the glass transition temperature (Tg) of the polymer to make it more usable. The Tg is the temperature at which an amorphous polymer (or the amorphous regions in a partially crystalline polymer) changes from a hard and relatively brittle condition to a viscous or rubbery condition. Plasticizers function by decreasing the Tg of the polymer so that under ambient conditions the films are softer, more pliable and often stronger, and thus better able to resist mechanical stress. Eudragit® NE30D, however, has a low Tg and accordingly does not require the use of plasticizers. In fact, addition of plasticizers can be detrimental as it can increase the viscosity of the Eudragit® NE30D formulation and negate one of the distinct advantages of the dispersion over the polymeric solution. Incorporation of plasticizers into Eudragit® NE30D formulations can also increase the tackiness of the coat and complicate the coating process.

Due to its low Tg, Eudragit® NE30D is known to be sensitive to excessive drying conditions or exposure to high temperatures. Prior art teachings state that excessive drying of Eudragit® NE30D coats can be detrimental as such conditions do not allow the coating formulation to spread out evenly and promote particle deformation and coalescence. For example, see Ghebre-Sellassie and Nesbit, *Application of Eudragit E30D in Controlled-Release Coatings* in Aqueous Polymeric Coatings for Pharmaceutical Forms, J. McGinity Ed., 1989, Marcel Dekker, Inc., pp 247-266. Also, it is known that during the coating process, the product temperature should be kept at around 26° C. If the product temperature is very high, the coating material becomes tacky owing to the low Tg of Eudragit® NE30D, which can lead to agglomeration of the coated product. The prior art teachings also state that Eudragit® NE30D coated products should not be stored at temperatures above 40° C., as stability tests conducted at elevated temperatures may not correlate with the long-term behavior of Eudragit® NE30D coated products at room temperature.

Attempts have been made in the prior art to design aqueous polymer coatings suitable for use on drug cores to obtain controlled or sustained release profiles using the Eudragit® polymers, and in particular Eudragit® NE30D It would seem that although the prior art teaches the use of aqueous acrylic dispersion coatings of Eudragit® polymers such as Eudragit® NE30D, in most part, the prior art does not seem to have overcome long term stability problems of products coated with aqueous Eudragit® NE30D dispersions. Where the products have been found to be stable, the length of curing is very long and this is inefficient to the manufacturing process and also raises problems with storage of scale-up product. Accordingly, and given the advantages and versatility of aqueous polymeric dispersion coatings such as those using Eudragit® NE30D, it would be desirable that a stable controlled or sustained release coat be developed with short curing times to enhance process times.

DEFINITIONS

The following definitions are provided in order to more specifically describe the invention. Otherwise all terms are to be accorded their ordinary meaning as they would be construed by one of ordinary skill in the art, i.e. pharmaceutical drug formulations.

The terms "treatment", "treating" or "treat" as used herein when referring to a condition, and as understood in the art, are defined to mean an approach for obtaining beneficial or desired results, including clinical results. Beneficial or desired clinical results can include, but are not limited to, alleviation of one or more symptoms of the condition, diminishment of extent of disease or condition, stabilized (i.e. not worsening) state of disease or condition, preventing spread of disease, delay or slowing of disease progression, palliation of the disease state, and remission (whether partial or total), whether detectable or undetectable. "Treatment" can also mean prolonging survival of a subject as compared to the expected survival of the subject if not receiving treatment.

The terms "subject" or "patient" as used herein are used interchangeably and mean all members of the animal kingdom (e.g. humans).

The term "effective amount" or "pharmaceutically effective amount" as used herein are used interchangeably, and are defined to mean the amount or quantity of the active drug or polymorph or enantiomer thereof which is sufficient to elicit an appreciable biological response when administered to a patient. It will be appreciated that the precise therapeutic dose will depend on the age and condition of the patient and the nature of the condition to be treated and will be at the ultimate discretion of the attendant physician.

The term "high-dose" as used herein refers to amounts of active drug that are dosed at about 500 mg or more per dosage form. Non limiting examples of "high-dose" amounts of active drug include 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, and 2000 mg.

The term "pharmaceutically acceptable" as used herein refers to compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

The term "dissolution profile" or "release profile" as used herein are used interchangeably in this application, and are defined to mean a quality control test conducted according to instructions found in the United States Pharmacopoeia ("USP"), i.e. using a USP apparatus design with a dissolution medium as found in the USP. Dissolution tests in-vitro measure the rate and extent of dissolution of the active drug in an aqueous dissolution medium. The dissolution rate or in-vitro release rates of drug from the modified release dosage forms of the present invention can be measured using one of many USP apparatus designs and dissolution media; non-limiting examples of which include a USP Type 1 apparatus design or USP Type 2 apparatus design, with a dissolution medium selected from water; 0.1N HCl; 0.1N HCl with added Sodium Chloride (e.g. 15.7 g NaCl/Liter); 0.1N HCl with added 0.1% Cetrimide; USP Buffer pH 1.5; Acetate Buffer pH 4.5; Phosphate Buffer pH 6.5; Phosphate Buffer pH 6.8; and Phosphate Buffer pH 7.4. The terms "% released" and "% dissolved", when referring to a dissolution profile, are used interchangeably in this application and are defined to mean the extent (%) of active drug released in an aqueous dissolution medium (in vitro).

The terms "active", "active agent", "active pharmaceutical agent", "active drug" or "drug" as used herein are used interchangeably and are defined to mean any active pharmaceutical ingredient ("API"), including its pharmaceutically acceptable salts (non-limiting examples of which include the hydrochloride salts, the hydrobromide salts, the hydroiodide salts, and the saccharinate salts), as well as the anhydrous, hydrated, and solvated forms, polymorphs, prodrugs, and the individually optically active enantiomers of the API. The active drug includes the molecule or ion and the appended portions of the molecule that cause the drug to be an ester or salt of the molecule.

The term "moiety" as used herein is defined to mean the molecule or ion, excluding those appended portions of the molecule that cause the drug to be an ester or salt of the molecule, responsible for the physiological or pharmacological action of the drug substance.

The terms "pharmaceutical composition" or "dosage form" as used herein are used interchangeably and are defined to mean a pharmaceutical composition, preparation or system in which doses of medicine or active drug are included. Pharmaceutical compositions or dosage forms can be administered by any route of administration known to the skilled in the art, including but not limited to oral, parenteral, pulmonary, rectal, vaginal, nasal and topical.

The term "oral dosage form" as used herein is defined to mean a dosage form which is administered by mouth, for absorption through the mucous membranes of the mouth and/or, after swallowing, through the gastrointestinal tract. Such oral dosage forms include but are not limited to solutions, syrups, suspensions, emulsions, gels, powders, granules, capsules, tablets, buccal dosage forms and sublingual dosage forms.

The term "immediate release dosage forms" or dosage forms which exhibit an "immediate release" of the active drug as used herein is defined to mean dosage forms which provide a substantially immediate rate of release of the active drug. Immediate release dosage forms typically release the drug content into the gastrointestinal tract within a short period of time after administration, and plasma drug levels generally peak shortly after dosing.

The term "modified release dosage forms" or dosage forms which exhibit a "modified release" of the active drug as used herein is defined to mean dosage forms whose drug release characteristics of time, course and/or location are designed to accomplish therapeutic or convenience objectives not offered by immediate release dosage forms. Modified release dosage forms encompass, but are not limited to, "controlled release", "sustained release", "extended release", "prolonged release", "delayed release" and "enhanced absorption" dosage forms.

The terms "controlled release dosage form", "control-releasing dosage form", "rate-controlled release dosage form" or dosage forms which exhibit a "controlled release" of the active drug as used herein are used interchangeably and defined as those whose drug release characteristics of time course and/or location are chosen to accomplish therapeutic or convenience objectives not offered by conventional immediate release dosage forms. The rate of release of the active drug from a controlled release dosage form is controlled by features of the dosage form and/or in combination with physiologic or environmental conditions rather than by physiologic or environmental conditions alone. The controlled release dosage forms of certain embodiments can be contrasted with conventional immediate release dosage forms which typically produce large maximum/minimum plasma drug concentrations (Cmax/Cmin) due to rapid absorption of the drug into the body (i.e., in-vivo, relative to the drug's therapeutic index; i.e., the ratio of the maximum drug concentration needed to produce and maintain a desirable pharmacological response). In conventional immediate release dosage forms, the drug content is released into the gastrointestinal tract within a short period of time, and plasma drug levels peak shortly after dosing. The design of conventional immediate release dosage forms is generally based on getting the fastest possible rate of drug release, and therefore absorbed, often at the risk of creating undesirable dose related side effects. The controlled release dosage forms of certain embodiments of the invention, on the other hand, improve the therapeutic value of the active drug by reducing the ratio of the maximum/minimum plasma drug concentration (Cmax/Cmin) while maintaining drug plasma levels within the therapeutic window. The controlled release dosage forms of certain embodiments attempt to deliver therapeutically effective amounts of active drug as a once-daily dose so that the ratio Cmax/Cmin in the plasma at steady state is less than the therapeutic index, and to maintain drug levels at constant effective levels to provide a therapeutic benefit over a period of time (e.g. 24-hour period). The controlled release dosage forms of certain embodiments of the invention, therefore, avoid large peak-to-trough fluctuations normally seen with conventional or immediate release dosage forms and can provide a substantially flat serum concentration curve throughout the therapeutic period. In certain embodiments controlled release dosage forms can provide a substantially constant or gradually decreasing rate of drug release so as to provide plasma levels which remain substantially invariant with time. In certain embodiments controlled release dosage forms can be designed to provide a quick increase in the plasma concentration of the drug which remains substantially constant within the therapeutic range of the drug for a period of time (e.g. 24-hour period). Alternatively, in certain other embodiments controlled release dosage forms can be designed to provide a quick increase in the plasma concentration of the drug, which although may not remain constant, declines at a rate such that the plasma concentration remains within the therapeutic range for a period of time (e.g. 24-hour period). The controlled release dosage forms of certain embodiments of the invention can be constructed in many forms known to one of ordinary skill in the drug delivery arts and described in the prior art.

The terms "sustained release dosage forms", "extended release dosage forms", "prolonged release dosage forms" or dosage forms which exhibit a "sustained release", "extended release", or "prolonged release" of the active drug, as used herein are used interchangeably and defined to mean dosage forms that provide a release of the active drug over an extended period of time compared to an immediate release dosage form, such that plasma concentrations of the active drug are maintained for a longer time at a therapeutic level, and therapeutic benefit is maintained for a prolonged period. In certain embodiments sustained release dosage forms are administered at least once-daily, and provide a release of the active drug sufficient to provide a therapeutic dose soon after administration and then a gradual release over a period of time such that the sustained-release dosage form provides a therapeutic benefit over a period of time (e.g. a 12-hour or 24-hour period).

The term "delayed-release dosage forms" or dosage forms which exhibit a "delayed release" of the active drug as used herein is defined to mean dosage forms that do not provide an immediate release of active drug following administration but provide a time delay prior to the commencement of drug release. This time delay is referred to as "lag time" and should not be confused with "onset time" which represents latency, that is, the time required for the drug to reach minimum effective concentration. In certain embodiments delayed release dosage forms are administered at least once-daily and do not effectively release drug immediately following administration but provide a time delay prior to the commencement of effective drug release. An example of a delayed release dosage form includes and is not limited to an enteric coated dosage form.

The term "enhanced absorption dosage forms" or dosage forms which exhibit an "enhanced absorption" of the active drug as used herein is defined to mean dosage forms that provide increased release and/or increased absorption of the active drug compared to other dosage forms containing the same or higher amount of the active drug, when exposed to like conditions. The same therapeutic effect can be achieved with less active drug in an enhanced absorption dosage form as compared to other dosage forms.

The term "tablet" as used herein refers to a single dosage form, i.e. the single entity containing the active pharmaceutical agent that is administered to the subject. The term "tablet" also includes a tablet that may be the combination of one or more "minitablets".

The terms "controlled release coating", "control releasing coating", "modified release coating" and "rate-controlling coating" as used herein are used interchangeably in this application, and are defined to mean a functional coating that provides controlled release of the active drug from the controlled release dosage form such that the drug release characteristics of time course and/or location are chosen to accomplish therapeutic or convenience objectives not offered by conventional immediate release dosage forms. The rate of release of the active drug from the controlled release dosage form is controlled by features of the controlled release coating and/or in combination with physiologic or environmental conditions rather than by physiologic or environmental conditions alone. The controlled release coating is a functional coating that comprises at least one controlled release polymer. The controlled release coating can modify (e.g. slow) the rate of release of an active drug from the core of the dosage form. For example, the controlled release coating can be designed such that when the coating is applied onto the core, the core in conjunction with the controlled release coating, exhibits a "modified-release", "controlled-release", "sustained-release", "extended-release" and/or "delayed-release" profile. Combinations thereof are permissible. The controlled release coating can optionally comprise additional materials that can alter the functionality of the controlled release coating. The term "coat" is interchangeable with the term "coating".

The term "AQ" as used herein when referring to controlled release coatings of certain embodiments of the present invention, is defined to mean a controlled release coating that is formed by an aqueous based process that does not involve the use of an organic solvent. The coating composition of an AQ controlled release coating is aqueous based; in contrast to prior art coating compositions that are solvent based (e.g. "PharmaPASS" composition).

The terms "moisture barrier" and "moisture barrier coat" as used herein are used interchangeably and are defined to mean a coating which impedes or retards the absorption of moisture. Certain active drugs can be susceptible to decomposition over time under high humidity conditions. The proportion of the components of the moisture barrier and the amount of the moisture barrier applied onto the controlled release coating is such that the moisture barrier does not fall within the USP definition and requirement for an enteric coat. Suitably, the moisture barrier is comprised of an enteric and/or acrylic polymer, suitably an acrylic polymer, optionally a plasticizer, and a permeation enhancer. The permeation enhancer is a hydrophilic substance, which allows water to enter without physical disruption of the coating. The moisture barrier can additionally contain other conventional inert excipients.

The term "enteric coat" as used herein is defined to mean a coating or barrier applied to a dosage form that can control the location in the digestive system where the active drug is absorbed. For example, an enteric coating can be used to: (i) protect the drug from the destructive action of the enzymes or low pH environment of the stomach; (ii) prevent nausea or bleeding associated with the irritation of the gastric mucosa by the drug; and/or (iii) deliver the drug in an undiluted form in the intestine. Based on these criteria, in certain embodiments, the enteric coated dosage form can be regarded as a type of delayed release dosage form. They differ from sustained release dosage forms in that with sustained release dosage forms, the drug release is extended over a period of time to maintain therapeutic blood levels and to decrease the incidence of side effects caused by a rapid release; whereas, with enteric coatings, the primary objective is to confine the release of the drug to a predetermined region of the gastrointestinal tract. Enteric coatings work by presenting a surface that is substantially stable at acidic pH, but breaks down at higher pH to allow release of the drug in the intestine.

The terms "coating composition", "coat composition", "coating solution", "coat solution" "coating suspension", and "coat suspension" as used herein are used interchangeably and are defined to mean a mixture of excipients that is used to create a controlled release coating. The coating composition is applied onto a core to form an intermediate coating, and the intermediate coating is cured to form the controlled release coating.

The term "intermediate coating" and "intermediate coat" as used herein are used interchangeably and are defined to mean a coating applied onto a core wherein the coating has not yet been cured. After application to the core, the intermediate coating is cured to form the controlled release coating. The intermediate coating is formed from the coating composition.

The term "enteric polymer" as used herein is defined to mean a polymeric substance that when used in an enteric coat formulation, is substantially insoluble and/or substantially stable under acidic conditions exhibiting a pH of less than about 5 and which are substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coat, a normal release matrix core, a controlled release matrix core, and/or in a controlled release coating.

Enteric polymers can be combined with other pharmaceutically acceptable excipients to either facilitate processing of a coat comprising the enteric polymer or to alter the functionality of the coat.

The term "functional coating" as used herein is defined to mean a coating that affects the rate of release in-vitro or in-vivo of the active drug(s).

The terms "overcoat", "over-coating", "non-functional overcoat" and "non-functional coat" as used herein are used interchangeably and are defined to mean a coating that does not substantially affect the rate of release in-vitro or in-vivo of the active drug, but can enhance the chemical, biological, physical stability characteristics, or the physical appearance of the modified release dosage form.

The term "core" as used herein is defined to mean a solid vehicle in which at least one active drug is uniformly or non-uniformly dispersed. The core can be formed by methods and materials well known in the art, such as for example by compressing, fusing, or extruding the active drug together with at least one pharmaceutically acceptable excipient. The core can be manufactured into, for example, a homogenous or non-homogenous unitary core, a multiparticle, or a plurality of microparticles compressed into a unitary core. Non-limiting examples of cores include tablet cores, microparticle cores, matrix cores, and osmotic cores. The core can be coated with at least one functional coat and/or non-functional coat.

The term "plasticizer" as used herein includes any compounds capable of plasticizing or softening a polymer or a binder. Plasticizers are generally used in the prior art to modify the properties and characteristics of the polymers in the coatings or core of the dosage form for convenient processing during manufacture of the coatings and/or the core of the dosage form. Once the prior art coating and/or core have been manufactured, certain plasticizers can function to increase the hydrophilicity of the coating and/or the core of the dosage form in the environment of use. During manufacture of the prior art coating and/or core, the plasticizer can lower the melting temperature or glass transition temperature (softening point temperature) of the polymer or binder. In prior art dosage forms, plasticizers are included with a polymer to lower its glass transition temperature or softening point. Plasticizers can reduce the viscosity of a polymer.

The terms "pore former", "pore forming agent", and "pore forming additive" as used herein are used interchangeably in this application, and are defined to mean an excipient that can be added to a coating, wherein upon exposure to fluids in the environment of use, the pore former dissolves or leaches from the coating to form pores, channels or paths in the coating, that can fill with the environmental fluid and allow the fluid to enter the core and dissolve the active drug, and modify the release characteristics of the formulation. The pore formers can be inorganic or organic, and include materials that can be dissolved, extracted or leached from the coating in the environment of use.

The term "steady state" as used herein means that the blood plasma concentration curve for a given drug does not substantially fluctuate after repeated doses to dose of the formulation.

"AUC" as used herein means area under the plasma concentration-time curve, as calculated by the trapezoidal rule over a time interval (e.g. complete 24-hour interval); and signifies the extent of the absorption of a drug.

"Cmax" as used herein means the highest plasma concentration of the drug attained within the dosing interval (e.g., 24 hours).

"Cmin" as used herein means the minimum plasma concentration of the drug attained within the dosing interval (e.g. 24 hours).

"Cavg" as used herein means the plasma concentration of the drug within the dosing interval (e.g. 24-hours), and is calculated as AUC/dosing interval.

"Tmax" as used herein means the time period which elapses after administration of the dosage form at which the plasma concentration of the drug attains the highest plasma concentration of drug attained within the dosing interval (e.g. 24 hours).

The term "bioequivalence" as used herein is defined as there being about a 90% or greater probability that the bioavailability (AUC) of the active drug as determined by standard methods is from about 80% to about 125% of the second orally administrable dosage form comprising the same dose of the active drug and that there is about 90% or greater probability that the maximum blood plasma concentration (Cmax) of the active drug as measured by standard methods is from about 80% to about 125% of the second orally administrable dosage form. For example, the reader is referred to the final version of the guidance approved by the US Food and Drug Administration at the time of filing of this patent application i.e., the March 2003 Guidance for Industry Bioavailability and Bioequivalence Studies for Orally Administered Drug Products General Considerations, U.S. Department of Health and Human Services, Food and Drug Administration, Center for Drug Evaluation and Research (CDER), for a detailed discussion on bioequivalence.

The term "increased stability", "greater stability" or "enhanced stability" as used herein are used interchangeably in this application, and mean that the composition and/or the drug contained in the composition, shows at least not more degradation, and in certain embodiments shows less degradation, than an otherwise similar or identical composition without the controlled release coating of the present invention, when exposed to similar or identical conditions. Degradation can be determined, for example, by the difference in dissolution profiles (i.e. difference in rate and/or extent of drug release into the dissolution medium), or any measurable difference in the retention of drug potency, after a certain time period of storage under similar or identical conditions (e.g. 1 day, one week, 1 month, or one year storage at 25° C./60% RH).

The term "increased release" as used herein means that the rate and/or extent of drug release into the dissolution medium by a composition of the present invention, is greater than the rate and/or extent of drug release of an otherwise similar or identical composition that does not contain the controlled release coating of the present invention, under similar or identical conditions (e.g. similar or identical dissolution media).

The term "external environment of use" as used herein refers to an environment where the drug can be released into from an embodiment of the present invention. Non-limiting examples of an external environment of use include a solvent (e.g. water), a solution, the oral cavity (e.g. the human oral cavity), the interior of the stomach (e.g. the interior of a human stomach), the interior of a small intestine (e.g. the interior of a human small intestine, including the duodenum, the jejunum, the ileum, and any combination thereof), the interior of a large intestine (e.g. the interior of a human large intestine, including the ascending colon, the traverse colon, the descending colon, the sigmoid colon, the rectum, and the anal canal, and any combination thereof). Further non-limiting examples of an external environment of use can include a dissolution medium, wherein the temperature can range from greater than about 0 degrees C. to about 100 degrees C., including all values, ranges, and subranges therein (e.g. dissolution mediums wherein the temperature is about 37 degrees C.+/−0.5 degrees C.), and wherein the volume can range from about 1 ml to about 10,000 liters, including all values, ranges, and subranges therein, (e.g. dissolution mediums wherein the volume is about 500 ml or about 900 ml). Non-limiting examples of dissolution mediums include water, a 0.1N HCl aqueous solution, a 0.1N HCl aqueous solution with sodium chloride added in an amount of 15.75 g/liter of the solution, a 0.1N HCl aqueous solution with added 0.1 wt % Cetrimide wherein the wt % is based on the weight of the solution, USP Buffer having a pH of 1.5, an acetate buffer having a pH of 4.5, a phosphate buffer having a pH of 6.5, a phosphate buffer having a pH of 6.8, a phosphate buffer having a of pH 7.4, and a 0.1N HCl solution containing added sodium chloride in an amount of 14 g/liter of the solution. In certain embodiments the dissolution medium can be stirred by a paddle (e.g. a USP type II paddle), at for example 50 rotations per minute or in other embodiments at 100 rotations per minute, wherein the stirring rate by the paddle can range, for example, from greater than about 0 rotations per minute to about 5000 rotations per minute, including all values, ranges, and subranges therein. In certain embodiments the pressure of the atmosphere on the dissolution medium is about 1 atmosphere, and can range, for example, from about 0.5 atmospheres to about 10 atmospheres, including all values, ranges, and subranges therein. In certain embodiments the pH of the dissolution medium, can, for example range from about −1 to about 14, including all values, ranges, and subranges therein.

The term "gastric retention properties" as used herein is defined to mean the ability of the dosage form, upon oral administration, to be retained for a period of time in the gastric region such that the dosage form provides controlled release of an effective amount of the active drug in the stomach. In at least one embodiment, the dosage form, upon oral administration, is retained for a period of time in the stomach such that there is a controlled release of an effective amount of the active drug in the stomach. In at least one embodiment the dosage form upon oral administration, is retained for a period in the stomach such that there is a controlled release of the active drug and a subsequent absorption of the active drug in the lower gastrointestinal tract.

The terms "a", "an" or "at least one" as used herein are used interchangeably in this application, and are defined to mean "one" or "one or more".

The numerical parameters set forth in the following specification and attached claims that are modified by the term "about", are approximations that can vary depending upon the technological properties of the particular case. For example, the term "about" can mean within an acceptable error range (e.g. standard deviations) for the particular value as determined by one of ordinary skill in the art, which will depend in part on how the value is measured or determined, e.g., the limitations of the measurement system. At the very least, and not as an attempt to limit the application of the doctrine of equivalents to the scope of the claims, each numerical parameter modified by the term "about" should at least be construed in light of the number of reported significant digits and by applying ordinary rounding techniques. The terms "about" and "approximately" as used herein are used interchangeably.

Other terms are defined as they appear in the following description and should be construed in the context with which they appear.

DETAILED DESCRIPTION OF THE INVENTION

In certain embodiments of the present invention, there is provided a controlled release oral dosage form comprising a core that is surrounded by a controlled release coating. In at least one embodiment the controlled release coating is further surrounded by a non-functional overcoat. In at least one embodiment the core comprises at least one therapeutically active agent and one or more first pharmaceutically acceptable excipients. In at least one embodiment the one or more first pharmaceutically acceptable excipients comprises a superdisintegrant. In at least one embodiment the controlled release coating is a stable controlled release monolithic coating that is formed by a process that comprises coating the core with a coating composition to form a coated core with an intermediate coating, and curing the coated core to form the controlled release oral dosage form with the stable controlled release coating. In at least one embodiment the coating composition comprises an aqueous dispersion of a neutral ester copolymer without any functional groups, a poly glycol having a melting point of at least about 55° C., and one or more second pharmaceutically acceptable excipients. The curing is conducted at a temperature at least equal to or greater than the melting point of the poly glycol.

In at least one embodiment the effective amount of the at least one therapeutically active agent is more than about 500 mg.

In at least one embodiment the at least one therapeutically active agent comprises at least one of metformin, a pharmaceutically acceptable salt of metformin, and a mixture thereof.

In at least one embodiment the dosage form comprises more than about 500 mg of metformin hydrochloride.

In at least one embodiment the dosage form comprises about 1000 mg of metformin hydrochloride.

In at least one embodiment, the stable controlled release coating is formed by a process that excludes usage of an organic solvent.

In at least one embodiment, the stable controlled release coating hydrates when placed in an aqueous environment (e.g. water).

In at least one embodiment the controlled release dosage form expands in a dimensionally restricted manner when placed in an aqueous environment.

In at least one embodiment the controlled release dosage form floats when placed in an aqueous environment.

In at least one embodiment, the controlled release dosage form, upon oral administration to a patient, provides controlled release of an effective amount of the active drug to at least one region of the patient's upper gastrointestinal tract (e.g. the stomach).

In at least one embodiment the one or more first pharmaceutically acceptable excipients comprises at least one of crospovidone, crosscarmelose sodium (e.g. Ac-Di-Sol®), sodium starch glycolate (e.g. Explotab®), low-substituted hydroxypropylcellulose (L-HPC), and mixtures thereof.

In at least one embodiment, the dosage form exhibits a slower dissolution rate compared to an otherwise identical dosage form that does not contain a poly glycol in an amount of from about 0.1% to about 10% by weight of the coating composition.

In at least one embodiment, the stable controlled release coating releases greater than or equal to about 10% of the active agent from the oral dosage form within 24 hours of being placed into water.

In at least one embodiment, the curing is conducted for a time period of from about 1 to about 24 hours. In at least one embodiment, the curing is conducted for a time period of from about 1 to about 16 hours. In at least one embodiment, the curing is conducted for a time period of from about 1 to about 7 hours. In at least one embodiment, the curing is conducted for a time period of from about 1 to about 3 hours.

In at least one embodiment, the core comprises metformin hydrochloride in an amount of from about 71% to about 81% by dry weight of the tablet, colloidal silicon dioxide in an amount of from about 1.4% to about 2.4% by dry weight of the tablet, polyvinyl alcohol in an amount of from about 1.1% to about 4.1% by dry weight of the tablet, crospovidone in an amount of from about 7.0% to about 11.0% by dry weight of the tablet, and glyceryl behenate in an amount of from about 0.4% to about 3.5% by dry weight of the tablet; and the controlled release coating comprises an ethyl acrylate and methyl methacrylate copolymer dispersion (e.g. Eudragit® NE30D, Eudragit® NE40D, Eudragit® NM30D, Kollicoat® EMM30D, or combinations thereof) in an amount of from about 2.0% to about 5.5% by dry weight of the tablet, hypromellose (e.g. Pharmacoat® 606) in an amount of from about 0.8% to about 2.5% by dry weight of the tablet, talc (e.g. talc 400) in an amount of from about 0.6% to about 7.0% by dry weight of the tablet, a polyethylene glycol selected from the group consisting of polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, and mixtures thereof, in an amount of from about 0.2% to about 2.8% by dry weight of the tablet, titanium dioxide in an amount of from about 0% to about 1.0% by dry weight of the tablet, simethicone emulsion in an amount of from about 0% to about 0.2% by dry weight of the tablet, and polysorbate 80 in an amount of from about 0% to about 0.2% by dry weight of the tablet.

I. Cores

The core comprises an effective amount of a therapeutically active agent and at least one first pharmaceutically acceptable excipient. In at least one embodiment the one or more first pharmaceutically acceptable excipients in the core comprises a lubricant, a binder and/or filler, a glidant, a superdisintegrant, or a mixture thereof.

A wide variety of therapeutically active agents is contemplated. These include but are not limited to anti-tussives, anti-histamines, decongestants, alkaloids, mineral supplements, vitamins, antacids, ion exchange resins, anti-cholesterolemics, anti-lipid agents, anti-arrhythmics, anti-pyretics, analgesics, appetite suppressants, anti-depressants, expectorants, anti-anxiety agents, anti-ulcer agents, anti-inflammatory substances, coronary dilators, opioid agonists, cerebral dilators, peripheral vasodilators, anti-biotics, anti-virals, psycho-tropics, anti-manics, stimulants, gastrointestinal agents, sedatives, anti-diarrheal agents, anti-anginal drugs, vasodilators, anti-hypertensive drugs, vasoconstrictors, migraine treatments, anti-infectives, tranquilizers, anti-psychotics, anti-tumor drugs, anticoagulants, antithrombic drugs, hypnotics, anti-emetics, anti-nauseants, anti-convulsants, neuromuscular drugs, hyper- and hypoglycemic agents, thyroid and anti-thyroid agents, diuretics, anti-spasmodics, uterine relaxants, mineral and nutritional additives, anti-obesity drugs, anabolic drugs, erythropoietic drugs, anti-asthmatics, cough suppressants, mucolytics, $H_2$-antagonists, anti-uricemic drugs. Mixtures are operable depending on the type of drugs. The skilled artisan will know, based on his technical knowledge, which drug combinations are acceptable. The therapeutically active agent(s) are present in an amount from about 5% to about 99% by weight of the cores. The amount present is highly dependent on the agent(s), the desired controlled release profile, and the strength of the desired dosage form. Different forms of the therapeutically active agent are also contemplated. The present invention encompasses polymorphs thereof and specific purified enantiomeric forms thereof. In certain embodiments the therapeutically active agent includes the individually optically active enantiomers of the therapeutically active agent. Pharmaceutically acceptable salts, as for example pharmaceutically acceptable addition salts, of the therapeutically active agent(s) are also suitable. Suitable pharmaceutically acceptable addition salts can include and are not limited to the hydrochloride salt, the hydrobromide salt, the hydroiodide salt, the saccharinate salt etc.

In certain embodiments the active drug comprises at least one of metformin, bupropion, tramadol, venlafaxine, quetiapine, atomoxetine, salts thereof, and combinations thereof.

In at least one embodiment the active drug comprises at least one of metformin, a pharmaceutically acceptable salt of metformin, and a mixture thereof. In certain embodiments metformin hydrochloride is present in an amount of from about 50% to about 100% by dry weight of the core, including all values and subranges therebetween. In certain other embodiments the metformin hydrochloride is present in an amount of from about 75% to about 92% by dry weight of the core, including all values and subranges therebetween; for example, including about 75%, about 76%, about 77%, about 78%, about 79% about 80%, about 81%, about 82%, about 83%, about 84%, about 85%, about 86%, about 87%, about 88%, about 89%, about 90%, about 91%, and about 92% by dry weight of the core.

In certain embodiments metformin hydrochloride is present in the core of the tablet in an amount of from about 40% to about 99% by dry weight of the tablet including all values and subranges therebetween. In other embodiments the metformin hydrochloride is present in an amount of from about 60% to about 92% by dry weight of the tablet including all values and subranges therebetween. In still other embodiments the metformin hydrochloride is present in an amount of from about 71% to about 81% by dry weight of the tablet including all values and subranges therebetween; for example, including about 71%, about 72%, about 73%, about 74%, about 75%, about 76%, about 77%, about 78%, about 79% about 80%, and about 81% by dry weight of the tablet.

In certain embodiments the dosage form comprises metformin in an amount of from about 50 mg to about 1000 mg. The range of metformin of from about 50 mg to about 1000 mg includes all values and ranges there between; for example, about 75, about 100, about 125, about 150, about 175, about 200, about 225, about 250, about 275, about 300, about 325, about 350, about 375, about 400, about 425, about 450, about 475, about 500, about 520, about 525, about 530, about 540, about 550, about 560, about 570, about 575, about 580, about 590, about 600, about 625, about 650, about 675, about 700, about 725, about 750, about 775, about 800, about 825, about 850, about 875, about 900, about 925, about 950, and about 975 mg of metformin. For example, certain embodiments include a pharmaceutical composition which comprises about 1000 mg of metformin per unit dose. Certain other embodiments can include more than about 1000 mg of metformin, e.g., from more than about 1000 mg to about 2000 mg of metformin, including all values there between, for example about 1050, about 1100, about 1150, about 1200, about 1250, about 1300, about 1350, about 1400, about 1450, about 1500, about 1550, about 1600, about 1650, about 1700, about 1750, about 1800, about 1850, about 1900, and about 1950 mg of metformin.

Glidants can be added to the core to improve the flowability of the excipient powder by reducing intraparticulate friction, and can be helpful in this regard during tablet production at high production speeds and during direct compaction. Examples of glidants include but are not limited to starch, talc, lactose, stearates (such as for example magnesium stearate), dibasic calcium phosphate, magnesium carbonate, magnesium oxide, calcium silicate, Cabosil™, colloidal silicon dioxide (e.g. Aerosil® 200), colloidal silica (Syloid™) and silicon dioxide aerogels. Glidants, if present, in certain embodiments, can range in amounts of from greater than about 0% to about 20% by weight of the core. In certain embodiments the glidant is present in an amount of from greater than about 0% to about 4% by weight of the core including all values and subranges therebetween. In other embodiments the glidant is present in an amount of from about 1.1% to about 3.1% by weight of the core, including all values and subranges therebetween. In still other embodiments the glidant is present in an amount of from about 1.6% to about 2.6% by weight of the core, including all values and subranges therebetween; for example, including about 1.7%, about 1.8%, about 1.9%, about 2.0%, about 2.1%, about 2.2%, about 2.3%, about 2.4%, and about 2.5% by weight of the core. In at least one embodiment the glidant used in the core is colloidal silicon dioxide. In certain embodiments the glidant is present in the core in an amount of from about 0% to about 4.0% by dry weight of the tablet including all values and subranges therebetween; for example, including about; in other embodiments in an amount of from about 0.9% to about 3.0% by dry weight of the tablet, including all values and subranges therebetween; and in still other embodiments in an amount of from about 1.4% to about 2.4% by dry weight of the tablet, including all values and subranges therebetween; for example, including about 1.5%, about 1.6%, about 1.7%, about 1.8%, about 1.9%, about 2.0%, about 2.1%, about 2.2%, and about 2.3%, by dry weight of the tablet.

Lubricants can be added to the core to reduce the friction between the solid and the die wall during tablet formation and ejection. High friction during tabletting can cause a series of problems, including inadequate tablet quality (capping or even fragmentation of tablets during ejection, and vertical scratches on tablet edges) and may even stop production. Such lubricants include but are not limited to adipic acid, magnesium stearate, calcium stearate, zinc stearate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil and mixtures thereof. In at least one embodiment sodium stearyl fumarate is used as the lubricant. Waxy fatty acid esters, such as glyceryl behenate, sold as "Compritol™" products (e.g. Compritol™ 888ATO), can also be used as a lubricant. In at least one embodiment the lubricant used in the core is glyceryl behenate. Other useful commercial lubricants include "Stear-O-Wet™" and "Myvatex™ TL". Mixtures are operable. Lubricants, if present, in certain embodiments, can be used in amounts ranging from greater than about 0% to about 10% by weight of the core including all values and subranges therebetween. In certain embodiments the lubricant is present in an amount of from greater than about 0% to about 6% by weight of the core, including all values and subranges therebetween. In other embodiments the lubricant is present in an amount of from about 0.1% to about 4% by weight of the core, including all values and subranges therebetween. In still other embodiments the lubricant is present in an amount of from about 1% to about 3% by weight of the core including all values and subranges therebetween; for example, including about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, and about 2.9% by weight of the core. In certain embodiments the lubricant is present in the core in an amount of from about 0% to about 10% by dry weight of the tablet including all values and subranges therebetween; in other embodiments in an amount of from about 0.01% to about 5.0% by dry weight of the tablet, including all values and subranges therebetween; and in still other embodiments in an amount of from about 0.4% to about 3.5% by dry weight of the tablet, including all values and subranges therebetween; for example, including about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, and about 3.4% by dry weight of the tablet.

It is well known in the art that besides reducing friction, lubricants may cause undesirable changes in the properties of a tablet. The presence of a lubricant in the excipient powder is thought to interfere in a deleterious way with the bonding between the particles during compaction and thus reduce tablet strength. Because many lubricants are hydrophobic, tablet disintegration and dissolution are often retarded by the addition of a lubricant. Such negative effects can be related to the amount of lubricant present. Other considerations known in the art include the manner in which a lubricant is mixed, the total mixing time and the mixing intensity. In order to avoid these negative effects, hydrophilic substances may be substituted for the hydrophobic lubricants. Examples include, but are not limited to, surface-active agents and polyethylene glycol. A combination of hydrophilic and hydrophobic substances can also be used.

Anti-adherents reduce adhesion between the excipient powder mixture and the punch faces and thus reduces the sticking of the particles to the punches, a phenomenon known in the art as "sticking" or "picking", and is affected by the moisture content of the powder. One example of antiadherent is microcrystalline cellulose. Many lubricants such as magnesium stearate have also antiadherent properties. However, other substances with limited ability to reduce friction can also act as antiadherents. Such substances include for example talc and starch. Mixtures are operable. Antiadherents, if present, range from about 0% to about 20% by weight of the core depending on the antiadherent being used.

Sorbents are substances that are capable of sorbing some quantities of fluids in an apparently dry state. Thus, oils or oil-drug solutions can be incorporated into a powder mixture, which is granulated and compacted into tablets. Other examples of sorbing substances include microcrystalline cellulose and silica.

Diluents or fillers can be added to the core to increase the bulk weight of the blend resulting in a practical size for compression. The ideal diluent or filler should fulfill a series of requirements, such as: be chemically inert, be non-hygroscopic, be biocompatible, possess good biopharmaceutical properties (e.g. water soluble or hydrophilic), good technical properties (such as compactability and dilution capacity), have an acceptable taste and be cheap. As a single substance cannot fulfill all these requirements, different substances have gained use as diluents or fillers in tablets.

In at least one embodiment the filler is lactose. Lactose possesses a series of good filler properties, e.g. dissolves readily in water, has a pleasant taste, is non-hygroscopic and fairly non-reactive and shows good compactability. Other sugars or sugar alcohols, such as glucose, sucrose, sorbitol and mannitol, have been used as alternative fillers to lactose, primarily in lozenges or chewable tablets because of their pleasant taste. Mannitol has a negative heat of solution and imparts a cooling sensation when sucked or chewed.

Apart from sugars, perhaps the most widely used fillers are celluloses in powder forms of different types. Celluloses are biocompatible, chemically inert, and have good tablet forming and disintegrating properties. They are therefore used also as dry binders and disintegrants in tablets. They are compatible with many drugs but, owing to their hygroscopicity, may be incompatible with drugs prone to hydrolyse in the solid state. One type of cellulose powder used in tablet formulation is microcrystalline cellulose. In at least one embodiment the filler is microcrystalline cellulose.

Another example of a diluent or filler is dibasic and tribasic calcium phosphate, which is insoluble in water and non-hygroscopic but is hydrophilic, i.e. easily wetted by water. Other examples of diluents include but are not limited to di- and tri-basic starch, calcium carbonate, calcium sulfate, and modified starches. Many diluents are marketed in "direct compression" form, which adds other desirable properties, such as flow and binding. There are no typical ranges used for the diluents, as targeted dose and size of a tablet are variables that influence the amount of diluent that should be used.

Binders (also sometimes called adhesives) can be added so that tablets can be formed with the required mechanical strength. Binders can be added in different ways: (1) As a dry powder, which is mixed with other ingredients before wet agglomeration; (2) As a solution, which is used as agglomeration liquid during wet agglomeration. Such binders are often referred to as "solution binders", and (3) As a dry powder, which is mixed with the other ingredients before compaction (slugging or tabletting). Such binders are often referred to as "dry binders". Common traditional solution binders are starch, sucrose, and gelatin. More commonly used binders with improved adhesive properties, are polymers such as polyvinylpyrrolidone and cellulose derivates such as for example hydropropyl methylcellulose. Examples of dry binders include microcrystalline cellulose and crosslinked polyvinylpyrrolidone. Other examples of binders include but are not limited to pregelatinized starches, methylcellulose, sodium carboxymethylcellulose, ethylcellulose, polyacrylamides, polyvinyloxoazolidone and polyvinylalcohols. In at least one embodiment the binder used is polyvinyl alcohol. Binders, if present, in certain embodiments, can range in amounts of from greater than about 0% to about 25% by weight of the core, including all values and subranges therebetween, depending on the binder used. In certain embodiments the binder is present in the core in an amount of from greater than about 0% to about 10% by weight of the core, including all values and subranges therebetween. In other embodiments the binder is present in an amount of from about 1% to about 5% by weight of the core, including all values and subranges therebetween. In still other embodiments the binder is present in an amount of from about 1.4% to about 4.3% by weight of the core, including all values and subranges therebetween; for example, including about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1% and about 4.2% by weight of the core. In certain embodiments the binder is present in the core in an amount of from about 0% to about 10% by dry weight of the tablet, including all values and subranges therebetween; in other embodiments in an amount of from about 1.0% to about 5.0% by dry weight of the tablet, including all values and subranges therebetween; and in still other embodiments in an amount of from about 1.1% to about 4.1% by dry weight of the tablet, including all values and subranges therebetween; for example, including about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, and about 4.0% by dry weight of the tablet.

Superdisintegrants are typically incorporated into immediate release dosage forms or orally disintegrating tablets to promote rapid disintegration of the dosage form and immediate release of the active agent. (A. Quadir and K. Kolter, "*A Comparative Study of Current Superdisintegrants*", Pharmaceutical Technology, Oct. 1, 2006). However, in certain embodiments of the present invention, one or more superdisintegrants are added to the core of the controlled release dosage form without there being a rapid disintegration of the dosage form. In such embodiments, the superdisintegrant promotes water uptake (for example, by the wicking of water into the core), due to their cross-linked structure, leading to hydration of the core, thereby facilitating drug dissolution at lower levels than traditional disintegrants such as starch. Further, in certain other embodiments, the superdisintegrant leads to hydration of the coating such that the hydrated dosage form is prevented from entering the small intestine and is retained in the stomach of the patient for a period of time. In such embodiments, the drug is released from the hydrated dosage form into the stomach of the patient, where many drugs are absorbed more easily. In addition, the superdisintegrant can reduce the adverse effects of fluidity or compactability when compared to traditional disintegrants. In certain embodiments of the present invention, the superdisintegrant promotes hydration of the coating and the core while unexpectedly not rupturing the controlled release coating and allowing a controlled release of the active agent from the core of the controlled release dosage form. The dosage form of the present invention is not rapidly disintegrated by the presence of a superdisintegrant in the core. In certain embodiments of the present invention the dosage form is a controlled release dosage form (e.g. once-daily oral dosage form), despite having a superdisintegrant in the core. Non-limiting examples of superdisintegrants include cross-linked polymers such as crospovidone, cross-linked celluloses such as crosscarmelose sodium (e.g. Ac-Di-Sol®), cross-linked starches such as sodium starch glycolate (e.g. Explotab®), low-substituted hydroxypropylcellulose (L-HPC), and mixtures thereof. In at least one embodiment the superdisintegrant used in the core comprises crospovidone (e.g. Kollidon® CL). In at least one other embodiment the superdisintegrant used in the core comprises crosscarmelose sodium. In certain embodiments the superdisintegrant is present in the core in an amount of from greater than about 0% to about 20% by dry weight of the tablet, including all values and subranges therebetween; in other embodiments in an amount of from about 4.0% to about 14.0% by dry weight of the tablet, including all values and subranges therebetween; and in still other embodiments in an amount of from about 7.0% to about 11.0% by dry weight of the tablet including all values and subranges therebetween; for example, including about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, about 10.5%, about 10.6%, about 10.7%, about 10.8%, and about 10.9% by dry weight of the tablet.

In at least one embodiment the one or more first pharmaceutically acceptable excipients in the core comprise at least one of colloidal silicon dioxide, polyvinyl alcohol, crospovidone, glyceryl behenate, and mixtures thereof.

The manufacturing process of the core can be as follows. The at least one therapeutically active agent is first granulated with the at least one binder, in one embodiment a granulator, but not necessarily a fluidized bed granulator. The at least one binder is first dissolved or dispersed in a suitable solvent, in one embodiment water. The solution or suspension of the at least one binder is then sprayed onto the at least one therapeutically active agent in a granulator, in one embodiment a fluidized bed granulator. For example, fluidized bed granulators manufactured by Glatt™ GmbH (Germany) or GEA™ Niro (Denmark) can be used for this operation. An alternative process can be to use a conventional low shear or high shear mixer for granulation. If necessary, the at least one therapeutically active agent can be mixed with a filler, prior to the granulation step. Granules once dried can be mixed with the other pharmaceutically acceptable excipients, especially with the at least one lubricant, but also with at least one glidant and any other pharmaceutically acceptable excipient suitable to improve processing. The mixture of granules (in one embodiment with the at least one lubricant), and optionally at least one glidant is pressed into tablets. Alternatively, the at least one therapeutically active agent and the at least one lubricant can be mixed in a granulator, in one embodiment a fluidized bed granulator, and heated to the melting point of the at least one lubricant to form granules. This mixture can then be mixed with at least one suitable filler and compressed into tablets. Also, it is possible to mix the at least one therapeutically active agent and the at least one lubricant (in one embodiment polyvinyl alcohol) in a granulator, in one embodiment a fluidized bed granulator, and then to press the resulting granules into tablets. Tablets can be obtained by standard techniques, in one embodiment on a rotary tablet press [for example Courtoy™ (GEA Pharma Systems, Belgium), Manesty™ (Oystar Manesty, U.K.), Fette™ (Fette America, U.S.), or Kilian™ (Kilian & Co., Germany)] fitted with suitable dies and punches. The resulting pressed tablets are hereinafter referred as cores.

The cores are then coated with the semi-permeable coating designed to achieve a controlled release of the at least one therapeutically active agent.

II. Coating Formulation

At least one controlled release coating surrounds the core of the oral dosage form. In certain embodiments the controlled release coating is a stable controlled release monolithic coating that is formed by a process that comprises coating the core with a coating composition to form a coated core with an intermediate coating, and curing the coated core to form the stable controlled release coating. In at least one embodiment the coating composition comprises an aqueous dispersion of a neutral ester copolymer without any functional groups, a poly glycol having a melting point of at least 55° C., and one or more second pharmaceutically acceptable excipients. The curing is conducted at a temperature at least equal to or greater than the melting point of the poly glycol. In at least one embodiment the stable controlled release coating comprises a neutral ester copolymer without any functional groups, a poly glycol having a melting point of at least 55° C., and one or more second pharmaceutically acceptable excipients.

The coating composition comprises an aqueous dispersion of a neutral ester copolymer without any functional groups. The aqueous dispersion of a neutral ester copolymer without any functional groups can be an ethyl acrylate and methyl methacrylate copolymer dispersion. Non-limiting examples of ethyl acrylate and methyl methacrylate copolymer dispersions include a 30% aqueous dispersion of a neutral copolymer based on ethyl acrylate and methyl methacrylate (e.g. Eudragit® NE30D), a 40% aqueous dispersion of a neutral copolymer based on ethyl acrylate and methyl methacrylate (e.g. Eudragit® NE40D), Eudragit® NM30D, Kollicoat® EMM30D, and combinations thereof. In at least one embodiment the neutral ester copolymer without any functional groups used in the controlled release coating composition is Eudragit® NE30D, Eudragit® NE40D, or a mixture thereof. The neutral ester copolymer without any functional groups can be present in certain embodiments in an amount of from about 1% to about 35% by weight of the coating composition, including all values and subranges therebetween, depending on the therapeutically active agent used and the controlled release profile desired. In certain embodiments the neutral ester copolymer without any functional groups is present in an amount from about 20% to about 99.5% by dry weight of the coat, including all values and subranges therebetween. In other embodiments the neutral ester copolymer without any functional groups is present in an amount from about 25% to about 60% by dry weight of the coat, including all values and subranges therebetween. In still other embodiments the neutral ester copolymer without any functional groups is present in an amount from about 37% to about 50% by dry weight of the coat, including all values and subranges therebetween; for example, including about 38%, about 39%, about 40%, about 41%, about 42%, about 43%, about 44%, about 45%, about 46%, about 47%, about 48%, and about 49% by dry weight of the coat. In certain embodiments the neutral ester copolymer without any functional groups is present in the coating composition in an amount of from about 0.4% to about 39.8% by dry weight of the tablet including all values and subranges therebetween; in other embodiments in an amount of from about 0.8% to about 24.0% by dry weight of the tablet, including all values and subranges therebetween; and in still other embodiments in an amount of from about 2.0% to about 5.5% by dry weight of the tablet, including all values and subranges therebetween; for example, including about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4% by dry weight of the tablet.

In at least one embodiment, the controlled release dosage form does not swell in a dimensionally unrestricted manner upon imbibation of water. In certain embodiments there is some swelling of the controlled release dosage form in a dimensionally restricted manner upon imbibition of water. In certain embodiments the controlled release coating restricts the swelling of the dosage form upon imbibition of water.

The coating composition also comprises a poly glycol with a melting point of at least 55° C. The poly glycol with a melting point of at least about 55° C. can be a polyethylene glycol with an average molecular weight ranging from about 4,000 daltons to about 35,000 daltons. Non-limiting examples of a polyglycol with a melting point of at least about 55° C. that can be used with the coating composition of the present invention include polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, and mixtures thereof. In certain embodiments, the poly glycol is selected from the group consisting of polyethylene glycol 6000, polyethylene glycol 8000, polyethylene glycol 10000, polyethylene glycol 12000, and mixtures thereof. In at least one embodiment the poly glycol used in the coating composition is polyethylene glycol 8000. The poly glycol can be present in certain embodiments in an amount of from about 0.1% to about 10% by weight of the coating composition, including all values and subranges therebetween. In certain embodiments the poly glycol is present in an amount of from about 0.5% to about 28% by dry weight of the coat, including all values and subranges therebetween. In other embodiments the poly glycol is present in an amount from about 4% to about 17% by dry weight of the coat, including all values and subranges therebetween. In still other embodiments the poly glycol is present in an amount from about 7.2% to about 15.2% by dry weight of the coat, including all values and subranges therebetween; for example, including about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, about 12.0%, about 12.1%, about 12.2%, about 12.3%, about 12.4%, about 12.5%, about 12.6%, about 12.7%, about 12.8%, about 12.9%, about 13.0%, about 13.1%, about 13.2%, about 13.3%, about 13.4%, about 13.5%, about 13.6%, about 13.7%, about 13.8%, about 13.9%, about 14.0%, about 14.1%, about 14.2%, about 14.3%, about 14.4%, about 14.5%, about 14.6%, about 14.7%, about 14.8%, about 14.9%, about 15.0%, and about 15.1% by dry weight of the coat. In certain embodiments the poly glycol is present in the coating composition in an amount of from about 0.1% to about 11.2% by dry weight of the tablet, including all values and subranges therebetween; in other embodiments in an amount of from about 0.1% to about 8.0% by dry weight of the tablet, including all values and subranges therebetween; and in still other embodiments in an amount of from about 0.2% to about 2.8% by dry weight of the tablet, including all values and subranges therebetween; for example, including about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, and about 2.7% by dry weight of the tablet. Other suitable polyglycol derivatives having a melting point of at least about 55° C. can be, but are not limited to, Poloxamer 188, Poloxamer 338, Poloxamer 407, Polyethylene Oxides, Polyoxyethylene Alkyl Ethers, Polyoxyethylene Stearates, and mixtures thereof.

In addition to the copolymers and the poly glycol, the coating composition comprises one or more other pharmaceutically acceptable excipients. The excipients can include but are not limited to anti-tacking agents, emulsifying agents, antifoaming agents, hydrophilic agents, flavourants, colourants, sweeteners etc, and any combination thereof. It is known in the art that depending on the intended main function, excipients can affect the properties of the coat in a series of ways, and many substances used in coat formulations can thus be described as multifunctional. A skilled worker will know, based on his technical knowledge, which pharmaceutically acceptable excipients are suitable for the desired controlled release coating composition.

Hydrophilic agents can be included in the coat to promote wetting of the coat when in contact with gastrointestinal fluids. Such hydrophilic agents include hydrophilic water soluble polymers such as hydroxypropyl methylcellulose (HPMC) (e.g. Pharmacoat® 606 or Hypromellose), hydroxypropyl cellulose (HPC), methyl cellulose, hydroxyethyl cellulose, hydroxyethyl methylcellulose, polyvinylpyrrolidone (Povidone® or Kollidon®), polyvinyl alcohol, polyethylene oxide, vinylpyrrolidone-vinyl acetate copolymer (Kollidon® VA64), polyethylene glycol-polyvinyl alcohol copolymer (Kollicoat® IR), copolymers thereof, and combinations thereof. In at least one embodiment, HPMC is the hydrophilic agent used in the coating composition. In certain embodiments, the hydrophilic agent comprises a pH-dependent polymer, non-limiting examples of which include: Cellulose Acetate Phthalate (e.g. Aquacoat® CPD); Cellulose Acetate Trimellitate, Poly(methacrylic acid, ethyl acrylate) 1:1 (e.g. Eudragit® L30D-55); Kollicoat® MAE 30 D; Poly(methacrylic acid, ethyl acrylate) 1:1 (e.g. Eudragit® L100-55); Kollicoat®& MAE 30 DP; Eudragit®& FS 30D; Hypromellose Acetate Succinate LF, MF, HF grades (e.g. AQOAT®)), Polyvinyl Acetate Phthalate, and mixtures thereof. If hydrophilic agents are to be included in the coat composition the agents can be present in certain embodiments in an amount from about 0.1% to about 10% by weight of the coating composition, including all values and subranges therebetween, in other embodiments from about 0.1% to about 5% by weight of the coating composition, including all values and subranges therebetween, and in still other embodiments from about 0.1% to about 3% by weight of the coating composition, including all values and subranges therebetween. In certain embodiments the hydrophilic agent is present in an amount of from greater than about 0% to about 35% by dry weight of the coat, including all values and subranges therebetween. In other embodiments the hydrophilic agent is present in an amount from about 8% to about 30% by dry weight of the coat, including all values and subranges therebetween. In still other embodiments the hydrophilic agent is present in an amount from about 12% to about 26% by dry weight of the coat, including all values and subranges therebetween; for example, including about 13%, about 14%, about 15%, about 16%, about 17%, about 18%, about 19%, about 20%, about 21%, about 22%, about 23%, about 24%, and about 25% by dry weight of the coat. In certain embodiments the hydrophilic agent is present in the coating formulation in an amount of from about 0% to about 14.0% by dry weight of the tablet, including all values and subranges therebetween; in other embodiments in an amount of from about 0.2% to about 6.0% by dry weight of the tablet, including all values and subranges therebetween; and in still other embodiments in an amount of from about 0.8% to about 2.5% by dry weight of the tablet, including all values and subranges therebetween; for example, including about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, and about 2.4% by dry weight of the tablet.

The tackiness of polymeric films is important for the coating of solid dosage forms and for the subsequent curing step (post coating thermal treatment). During coating with either cellulosic or acrylic polymers, an unwanted, and sometimes irreversible agglomeration of several granules or beads or, in the worst case, of the complete batch, can occur, especially at higher product processing temperatures. Accordingly, the addition of anti-tacking agents to coating formulations is desirable. The anti-tacking agents which can be used include but are not limited to adipic acid, magnesium stearate, calcium stearate, zinc stearate, hydrogenated vegetable oils, sterotex, glyceryl monostearate, talc (e.g. Talc 400), sodium benzoate, sodium lauryl sulfate, magnesium lauryl sulfate, and mixtures thereof. In at least one embodiment talc (e.g. talc 400) is used as the anti-tacking agent. Talc can also function as a wetting agent. Mixtures of the anti-tacking agents are operable. The amount of anti-tacking agent in the coating composition of certain embodiments can be in the range of from about 1% to about 15% by weight of the coating dispersion, including all values and subranges therebetween, and in certain embodiments from about 1% to about 7% by weight of the coating dispersion including all values and subranges therebetween. In certain embodiments the anti-tacking agent is present in an amount of from greater than about 0% to about 50% by dry weight of the coat including all values and subranges therebetween. In other embodiments the anti-tacking agent is present in an amount from about 2% to about 40% by dry weight of the coat including all values and subranges therebetween. In still other embodiments the anti-tacking agent is present in an amount from about 10% to about 30% by dry weight of the coat including all values and subranges therebetween; for example, including about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, and about 29% by dry weight of the coat. In certain embodiments the anti-tacking agent is present in the coating formulation in an amount of from about 0% to about 20.0% by dry weight of the tablet, including all values and subranges therebetween; in other embodiments in an amount of from about 0% to about 12.0% by dry weight of the tablet, including all values and subranges therebetween; and in still other embodiments in an amount of from about 0.6% to about 7.0% by dry weight of the tablet, including all values and subranges therebetween; for example, including about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, and about 6.9% by dry weight of the tablet.

The anti-foaming agents, which can be included in the coating composition of the invention include silicon oil, simethicone (e.g. simethicone emulsion), and mixtures thereof. In at least one embodiment the anti-foaming agent is simethicone. The anti-foaming agent, if present, can be present in certain embodiments in an amount of up to about 0.5% by weight of the coat composition, including all values and subranges therebetween, and in certain other embodiments from about 0.1% to about 0.4% by weight of the coating composition, including all values and subranges therebetween. In certain embodiments the anti-foaming agent is present in an amount of from greater than about 0% to about 3% by dry weight of the coat, including all values and subranges therebetween. In other embodiments the anti-foaming agent is present in an amount from about 0.4% to about 2% by dry weight of the coat, including all values and subranges therebetween. In still other embodiments the anti-foaming agent is present in an amount from about 0.8% to about 1.5% by dry weight of the coat, including all values and subranges therebetween; for example, including about 0.9%, about 1.0%, about 1.1%, about 1.2%, about 1.3%, and about 1.4% by dry weight of the coat. In certain embodiments the anti-foaming agent is present in the coating formulation in an amount of from about 0% to about 1.2% by dry weight of the tablet, including all values and subranges therebetween; in other embodiments in an amount of from about 0% to about 0.8% by dry weight of the tablet, including all values and subranges therebetween; and in still other embodiments in an amount of from about 0% to about 0.2% by dry weight of the tablet, including all values and subranges therebetween; for example, including about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

The inclusion of an emulsifying agent (also called emulsifiers or emulgents) can be used to facilitate actual emulsification during manufacture of the coat, and also to provide emulsion stability during the shelf-life of the product. Emulsifying agents useful for the coat composition of the invention include, but are not limited to naturally occurring materials and their semi synthetic derivatives, such as the polysaccharides, as well as glycerol esters, cellulose ethers, sorbitan esters and polysorbates. Mixtures are operable. In at least one embodiment the emulsifying agent used is Polysorbate 80 (polyoxyethylene sorbitan mono-oleate), (e.g. Tween®180). The emulsifying agent or agents, if present, can be present in certain embodiments in an amount of from greater than 0% to about 0.5% by weight of the coat composition, including all values and subranges therebetween. In at least one embodiment the emulsifying agent is present in an amount of from about 0.1% to about 0.3% by weight of the coat composition, including all values and subranges therebetween. In certain embodiments the emulsifying agent is present in an amount of from greater than about 0% to about 2% by weight of the coat, including all values and subranges therebetween. In other embodiments the emulsifying agent is present in an amount from about 0.1% to about 1% by dry weight of the coat, including all values and subranges therebetween. In still other embodiments the emulsifying agent is present in an amount from about 0.25% to about 0.75% by dry weight of the coat, including all values and subranges therebetween; for example, including about 0.30%, about 0.35%, about 0.40%, about 0.45%, about 0.50%, about 0.55%, about 0.60%, about 0.65%, and about 0.70% by dry weight of the coat. In certain embodiments the emulsifying agent is present in the coating formulation in an amount of from greater than about 0% to about 0.8% by dry weight of the tablet, including all values and subranges therebetween; in other embodiments in an amount of from greater than about 0% to about 0.4% by dry weight of the tablet, including all values and subranges therebetween; and in still other embodiments in an amount of from greater than about 0% to about 0.2% by dry weight of the tablet, including all values and subranges therebetween; for example, including about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

Any permitted colourants in a film coat formula are invariably water-insoluble colors (pigments). Pigments have certain advantages over water-soluble colors in that they tend to be more chemically stable towards light, provide better opacity and covering power, and optimize the impermeability of a given film to water vapor. Examples of suitable colorants include, but are not limited to iron oxide pigments, titanium dioxide, and aluminum Lakes. Mixtures are operable. In at least one embodiment the pigment or colorant used is titanium dioxide. The pigment or colorant, if present, can be present in certain embodiments in an amount of from about 0.1% to about 10% by weight of the coat composition, including all values and subranges therebetween. In at least one embodiment the colorant is present in an amount of from about 0.1% to about 5% by weight of the coat composition, including all values and subranges therebetween. In at least one other embodiment the colorant is present in an amount of from about 0.1% to about 2% by weight of the coat composition, including all values and subranges therebetween. In certain embodiments the colorant is present in an amount of from greater than about 0% to about 20% by dry weight of the coat, including all values and subranges therebetween. In other embodiments the colorant is present in an amount from greater than about 0% to about 10% by dry weight of the coat, including all values and subranges therebetween. In still other embodiments the colorant is present in an amount from about 2.2% to about 6.2% by dry weight of the coat, including all values and subranges therebetween; for example, including about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, and about 6.1% by dry weight of the coat. In certain embodiments the colorant is present in the coating formulation in an amount of from greater than about 0% to about 8.0% by dry weight of the tablet, including all values and subranges therebetween; in other embodiments in an amount of from greater than about 0% to about 5.0% by dry weight of the tablet, including all values and subranges therebetween; and in still other embodiments in an amount of from greater than about 0% to about 1.0% by dry weight of the tablet, including all values and subranges therebetween; for example, including about 0.1%, about 0.2%, about 0.3%, about 0.4%, about 0.5%, about 0.6%, about 0.7%, about 0.8%, and about 0.9% by dry weight of the tablet.

In at least one embodiment the second pharmaceutically acceptable excipients in the controlled release coating comprises at least one of a neutral ester copolymer without any functional groups (e.g. Eudragit® NE30D, Eudragit® NE40D, Eudragit® NM30D, Kollicoat® EMM30D, or a mixture thereof), HPMC (e.g. Pharmacoat®606), talc (e.g. Talc 400), polyethylene glycol (e.g. polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, or a mixture thereof), simethicone, polysorbate 80, titanium dioxide, and mixtures thereof.

In at least one embodiment, the stable controlled release coating hydrates when placed into water. In at least one embodiment the dosage form that is coated with the controlled release coating floats in water. In at least one embodiment, the controlled release dosage form, upon oral administration to a patient, provides controlled release of an effective amount of the active drug to at least one region of the patient's upper gastrointestinal tract (e.g. the stomach).

In certain embodiments the controlled release coating is formed by a process that does not involve the use of an organic solvent. In such embodiments the controlled release coating composition is aqueous based and not solvent based (termed "AQ" in certain examples of dosage forms coated with the aqueous based controlled release coating); in contrast to prior art coating compositions that are solvent based (e.g. "PharmaPASS™" composition).

The coating composition can be applied onto a core comprising an effective amount of the therapeutically active agent by a process, which involves the atomization (spraying) of the coating composition (solution or suspension) onto a bed of the tablet cores. Some examples of equipment suitable for film coating include: ACCELA COTA® (Manesty Machines, Liverpool, UK), HI-COATER® (Freund Company, Japan), DRIACOATER™ (Driam Metallprodukt GmbH, Germany), HTF/150™ (GS, Italy), and IDA™ (Dumoulin, France). Examples of units that function on a fluidized-bed principle include: AEROMATIC™ (Fielder, Switzerland and UK) and GLATT AG™ (Switzerland). In at least one embodiment the apparatus used is the ACCELA COTA®.

The coating composition is delivered to the coating apparatus from a peristaltic pump at the desired rate and sprayed onto the rotating or fluidizing tablet cores. The tablet cores are pre-warmed to about 30° C. During the coating process, the product temperature range is maintained between about 25° C. and about 35° C. by adjusting the flow rate of the inlet and outlet air, temperature of the inlet air and spray rate. A single layer of the coating composition is applied and once spraying is complete, the coated tablet cores are dried between about 30° C. to about 40° C. for about 3 to about 5 minutes at a low pan speed and low air flow. The pan is readjusted to jog speed, and drying continued for about 12 to about 15 minutes.

The coated tablet cores are placed onto a tray and cured (post coating thermal treatment) in an electrical or steam oven at a temperature above the temperature of the melting point of the polyethylene glycol or derivative thereof. In at least one embodiment the curing temperature is greater than the melting point of the polyethylene glycol or derivative thereof. In at least one embodiment the curing time is from about 2 to about 7 hours. The cured coated tablets are subsequently cooled to about room temperature.

In certain other embodiments, the coated tablet cores are placed onto a coating pan and cured at two-stages. During the first stage, the coated tablets are cured at a first curing temperature (for example, in certain embodiments from between about 50° C. to about 59° C.) for a period of time (for example, in certain embodiments from about 15 minutes to about 90 minutes; and in at least one embodiment for about 60 minutes). During the second stage, the coated tablets are cured at a second curing temperature that is at least equal to or greater than the melting point of the poly glycol (for example, in certain embodiments from between about 60° C. to about 70° C.) for an additional period of time (for example, in certain embodiments from about 30 minutes to about 180 minutes; and in at least one embodiment for about 120 minutes). In at least one embodiment the two-stage curing of the coated tablets reduces non-functional defects on the tablet caused by the curing process. In at least one embodiment the two-stage curing process substantially eliminates non-functional defects on the tablet caused by the curing process. Non-functional defects on the dosage form caused by the curing process can include visual defects in the coating (e.g. poor color uniformity, and/or dull appearance), defects in the surface of the coating (e.g. roughness in the surface of the coating, and/or wrinkles in the coating), and sticking of the tablets to each other and/or to the coating pan. In addition, the reduced defects in color and smoothness of the tablets allows for improved printing of the tablets The findings disclosed herein are particularly surprising and unexpected in light of the prior art teachings with regard to ethyl acrylate and methyl methacrylate copolymer dispersions (e.g. Eudragit® NE30D). Ethyl acrylate and methyl methacrylate copolymer dispersions have a low Tg, and the prior art teachings do not recommend the use of plasticizers, such as polyethylene glycol or its derivatives. In fact, the prior art teaches that the addition of plasticizers can be detrimental to ethyl acrylate and methyl methacrylate copolymer dispersions. Surprisingly and unexpectedly, however, applicants have found that addition of polyethylene glycol (having a melting point greater than 55 degrees C.) or its derivatives in the amounts described herein and curing the coated tablets at above the melting temperature of the polyethylene glycol, was not detrimental and provided for a controlled release of the therapeutically active agent. Moreover, the coated tablet cores were found to be stable in terms if dissolution rate over time, with minimal further gradual coalescence in evidence. The desired dissolution profile obtained provides a controllable lag time such as in an S-shaped Weibull profile. This is a surprising and unexpected result and is not taught in the prior art. The controlled lag time and the desired dissolution profile can be accomplished by a single coating.

As will be seen from the non-limiting examples described below, the coating of the invention is quite versatile. The coating formulation can be used to coat a variety of drug cores and can be manipulated to obtain a desired drug release profile. The length and time for the delay is controlled by rate of hydration and the thickness of the coat. The drug release rate subsequent to the delay is determined by the thickness and permeability of the hydrated coat. Thus, it is possible to regulate the rate of hydration and permeability of the coat so that the desired controlled-release drug profile can be achieved. There is no preferred coat thickness, as this will depend on the drug being used in the core and also the controlled release profile desired. Other parameters in combination with the thickness of the coat include varying the concentrations of some of the ingredients of the stable coat composition of the invention described and/or varying the curing temperature and length of curing the coated tablet cores. The skilled artisan will know which parameters or combination of parameters to change for a desired controlled release profile.

III. Non-Functional Overcoat Formulation

In certain embodiments, after the controlled release coating composition is applied to the core, an additional non-functional overcoat composition is applied over the controlled release coating composition before curing. In at least one embodiment the non-functional overcoat provides cosmetic benefits to the dosage form. In at least one embodiment the non-functional overcoat helps to protect the coated tablets from being damaged during the curing process. In at least one embodiment the non-functional overcoat reduces non-functional defects on the dosage form caused by the curing process. In at least one embodiment the non-functional overcoat substantially eliminates non-functional defects on the dosage form caused by the curing process. Non-functional defects on the dosage form caused by the curing process can include visual defects in the coating (e.g. poor color uniformity, and/or dull appearance), defects in surface of the coating (e.g. roughness in the surface of the coating, and/or wrinkles in the coating), and sticking of the dosage forms to each other and/or to the coating pan. In addition, the reduced defects in color and smoothness of the dosage form allows for improved printing of the dosage form.

In certain embodiments the non-functional overcoat comprises hydroxypropyl methylcellulose, polyethylene glycol, polydextrose, titanium dioxide, and triacetin. In certain other embodiments the non-functional overcoat comprises hydroxypropyl methylcellulose 2910, polyethylene glycol 400, polydextrose, titanium dioxide, carnuba wax, and iron oxide yellow. In at least one embodiment the non-functional overcoat comprises Opadry® II (white) in an amount of from about 0% to about 100% by dry weight of the non-functional overcoat. In certain embodiments the non-functional overcoat comprises Opadry® II (white) in an amount of from about 0% to about 10% by dry weight of the tablet; in certain other embodiments in an amount of from about 0% to about 6% by dry weight of the tablet; and in still other embodiments in an amount of from about 0% to about 3% by dry weight of the tablet. In at least one embodiment the non-functional overcoat comprises Opadry® II (white) in an amount of about 1.5% by dry weight of the tablet.

In at least one embodiment the non-functional overcoat formulation comprises Opadry® II (20.0% w/w) and purified water (80% w/w), wherein the purified water is evaporated during the coating process.

The following non-limiting examples illustrate the invention:

EXAMPLE 1

Metformin HCl Tablets 1.1 Tablet Core Preparation

The following formulation was prepared for Metformin HCl 500 mg strength tablets:

| Ingredients | % w/w |
| --- | --- |
| Metformin HCl | 95.70 |
| Silicon Dioxide* | 0.50 |
| Polyvinyl alcohol (PVA)** | 1.80 |
| Atomized Glyceryl Behenate*** | 2.00 |
| Total | 100.00 |

*Aerosil 200.
**The PVA is prepared as a 4% solution (w/w) in purified water. The purified water is not considered as part of the theoretical batch size since it is evaporated during drying of the core in the fluid bed granulator.
***Compritol 888 ATO All of the metformin and silicon dioxide was transferred to a V-blender and blended for about 10 min. The blended material was then discharged into a fluid bed granulator and granulation was carried out in the presence of the PVA solution under the following process parameters:

| Granulation Temperature (° C.) | 35-45 |
| --- | --- |
| Air Volume (m/s) | 0.5-3.0 |
| Atomization Air Pressure (Bar) | 0.5-2.0 |
| Fluid Spray Rate (g/min) | 3-11 |
| Drying Temperature (° C.) | 45-55 |

The LOD % of the granules after drying was NMT 3% as determined by moisture balance.

After drying, the granules were sized by passing the granules through a 0.71 mm screen. The screened granules were then transferred to a V-blender and blended with the remainder of the lactose and all of the atomized glyceryl behenate for about 10 min. Finally, the magnesium stearate was added and blending was carried out for about 5-10 more minutes.

The dissolution profile of the compressed tablet cores was determined under the following conditions:
Medium: 900 ml water
Method: USP Type II Apparatus, 50 rpm at 37° C.

The tablet cores are immediate release. The release of metformin HCl from the tablet cores was found to be about 100% in about 30 min.

1.2 Core Coating

The following three coating formulations were prepared:

| Ingredients | Coating MA (%) | Coating MB (%) | Coating MC (%) |
| --- | --- | --- | --- |
| Eudragit ® NE30D | 25.33 | 26.97 | 27.03 |
| Talc 400 | 6.84 | 5.30 | 5.32 |
| HPMC 606 | 5.98 | 2.47 | 2.25 |
| PEG 8000 | 2.14 | 2.25 | 2.25 |
| Titanium dioxide | 1.71 | 1.35 | 1.35 |
| Simethicone | 0.39 | 0.31 | 0.31 |
| Tween ® 80 | 0.34 | 0.23 | 0.23 |
| Purified Water | 57.27 | 61.12 | 61.26 |
| Total | 100.00 | 100.00 | 100.00 |

The metformin tablet cores were then coated with either one of the coating formulations. The coating process was carried out in a Glatt GPCG-1 apparatus equipped with a coating chamber without a Wuster column. The mesh size of the bottom screen was 200 μm and the size of the spray nozzle was 1 mm.

The coating formulation was prepared as follows:

| | Materials |
| --- | --- |
| Component A | Eudragit ® NE30D |
| | Water |
| Component B | HPMC 606 |
| | Water |
| Component C | Simethicone |
| | (DOW CORNING ®) |
| | Water |
| Component D | Tween ® 80 |
| | Water |
| Component E | Component D + C |
| Component F | Talc |
| | PEG 8000 (MT) |
| | Titanium dioxide |
| | Water |

Final coating Dispersion G (A + B + C + D + E + F)

1.2.1 Preparation of Component A

Water is transferred to a stainless steel container of a Silverson high-shear mixer and the mixer turned on at continuous low speed to produce a sufficient mixer. All of the assigned water is added to Eudragit NE 30D dispersion and mixed for about 10 min using a Caframo Mixer.

1.2.2 Preparation of Component B

All of the Pharmacoat® 606 is added to 65±5° C. water and mixed for about 5 min using a silverson high shear mixer at a low speed.

1.2.3 Preparation of Component C

All of the simethicone is placed in a 100 ml beaker to which 50 g of water is added and mixed to uniformity.

1.2.4 Preparation of Component D

All of the Tween® 80 is transferred to a 100 ml beaker to which 50 g of water is added and mixed until all the Tween 80 is dissolved.

1.2.5 Preparation of Component E

Dispersion E is prepared by uniformly mixing component D and component C.

1.2.6 Preparation of Component F

Water is transferred to a stainless steel container of a Silverson high-shear mixer and the mixer turned on at continuous low speed to produce a sufficient vortex. The PEG is added gradually to the vortex and mixed until the all of the PEG is dissolved. Components B and E are next added and mixing is continued for 5 min. All of the talc and titanium dioxide is added and mixed for another 15 min.

1.2.7 Preparation Final Coating Dispersion G

Component F is slowly added component A while stirring.

The processing parameters for coating the tablet cores were as follows:

| | |
|---|---|
| Coating Temperature (° C.) | 30-32 |
| Air Volume (m/s) | 4.0-6.5 |
| Atomization Air Pressure (Bar) | 1.3-2.3 |
| Coating Fluid Spray Rate (g/min) | 3-6 |
| Drying Temperature (° C.)** | 30-35 |

**Coated tablets were dried for about 3 min.

After application of the coating the tablets were cured in an oven at 62±2° C. for about 2 hours. This temperature is above the melting temperature of the polyethylene glycol 8000.

The metformin tablet cores were next coated with either one of the coating formulations MA, MB, or MC to a weight gain of either 14% or 16% w/w by weight of the tablet core and cured in an oven at between about 60° C. to about 75° C. for between about 2 hours to about 15 hours.

Dissolution tests of the coated tablet cores was carried out under the following dissolution conditions:

Medium: 900 ml water.

Method: USP Type II Apparatus, 50 rpm at 37° C.

The results are presented in Table 1 as a % release into the medium of the total metformin HCl in the tablet:

TABLE 1

| Time (h) | Tablet cores coated with coating formulation MA to 16% weight gain | Tablet cores coated with coating formulation MB to 14% weight gain | Tablet cores coated with coating formulation MC to 14% weight gain |
|---|---|---|---|
| 0 | 0 | 0 | 0 |
| 1 | 21.15 | 11.26 | 7.04 |
| 2 | 50.35 | 24.4 | 16.59 |
| 3 | 73.8 | 38.12 | 26.69 |
| 4 | 89.73 | 52.75 | 38.02 |
| 5 | 98.65 | 66.73 | 50.56 |

TABLE 1-continued

| Time (h) | Tablet cores coated with coating formulation MA to 16% weight gain | Tablet cores coated with coating formulation MB to 14% weight gain | Tablet cores coated with coating formulation MC to 14% weight gain |
|---|---|---|---|
| 6 | 102.24 | 79.25 | 63.31 |
| 7 | 103.55 | 88.78 | 74.98 |
| 8 | — | 95.41 | 84.71 |
| 9 | — | 99.42 | 91.92 |
| 10 | — | 101.76 | 96.47 |
| 11 | — | 103.05 | 99.45 |
| 12 | — | 103.86 | 101.21 |

A study was done to determine the effect of curing temperature and length of curing on drug dissolution. The curing temperature was set at 65° C. for 1, 2 and 5 hours. The effect on the dissolution of the drug at a curing temperature of 75° C. for about 2 hours was also determined. Dissolution tests of the coated tablets under the different curing temperatures and lengths of time were carried under the following dissolution conditions:

Medium: 900 ml water.

Method: USP Type II Apparatus, 50 rpm at 37° C.

The results are presented in Table 2 as a % release into the medium of the total metformin HCl in the tablet:

TABLE 2

| Time (h) | MB (65° C. - 60 min) | MB (65° C. - 120 min) | MB (65° C. - 300 min) | MB (75° C. - 120 min) |
|---|---|---|---|---|
| 0 | 0 | 0 | 0 | 0 |
| 1 | 9.98 | 8.08 | 7 | 6.47 |
| 2 | 23.73 | 18.65 | 17.14 | 15.76 |
| 3 | 40.53 | 29.8 | 27.62 | 25.67 |
| 4 | 61.77 | 42.52 | 39.8 | 36.6 |
| 5 | 81.77 | 56.48 | 53.84 | 48.63 |
| 6 | 92.51 | 71.32 | 67.67 | 60.74 |
| 7 | — | 80.94 | 79.85 | 72.57 |
| 8 | — | 86.35 | 88.24 | 82.13 |
| 9 | — | 90.36 | 92.96 | 88.28 |
| 10 | — | 92.69 | 95.47 | 91.68 |
| 11 | — | 94.87 | 97.57 | 94.02 |
| 12 | — | 96.14 | 98.39 | 95.67 |
| 13 | — | 97.37 | 99.23 | 96.93 |
| 14 | — | 98.21 | 99.69 | 97.56 |
| 15 | — | 98.71 | 99.97 | 98.33 |
| 16 | — | 99.47 | 100.37 | 98.83 |

A study was done to determine the effect of curing temperature and time on drug dissolution. The curing temperature was set at 55° C. for 5 and 16 hours. The effect on the dissolution of the drug at a curing temperatures of 70° C. for about 2 hours was also determined. Dissolution tests of the coated tablets under the different curing temperatures and lengths of time were carried under the following dissolution conditions:

Medium: 900 ml water.

Method: USP Type II Apparatus, 50 rpm at 37° C.

The results are presented in Table 3 as a % release into the medium of the total metformin HCl in the tablet:

TABLE 3

| Time (h) | Tablet Cores | MC (55° C. - 5 hr) | MC (55° C. - 16 hr) | MC (70° C. - 2 hr) |
|---|---|---|---|---|
| 0 | 0 | 0 | 0 | 0 |
| 1 | 103.92 | 13.08 | 11.86 | 7.04 |
| 2 | — | 37.54 | 32.76 | 16.59 |
| 3 | — | 54.51 | 54.39 | 26.69 |
| 4 | — | 67.48 | 67.85 | 38.02 |
| 5 | — | 78.38 | 78.89 | 50.56 |
| 6 | — | 87.14 | 88.15 | 63.31 |
| 7 | — | 93.31 | 93.43 | 74.98 |
| 8 | — | 96.5 | 96.12 | 84.71 |
| 9 | — | 98.11 | 97.55 | 91.92 |
| 10 | — | 99.11 | 98.36 | 96.47 |
| 11 | — | 99.51 | 98.82 | 99.45 |
| 12 | — | 99.91 | 99.13 | 101.21 |

The influence of the coat on different dissolution media relative to water was determined as follows:
Media: water, 0.1N HCl (pH1.2)+Citramide, or pH5.8 phosphate buffer+Citramide.
Method: USP Type II Apparatus, 50 rpm at 37° C.
The results are presented in Table 4 as a % release into the medium of the total metformin HCl in the tablet:

TABLE 4

| Time (h) | MC water | MB water | MC pH 5.8 + Citramide | MC pH 1.2 + Citramide | MB pH 5.8 + Citramide | MB pH 1.2 + Citramide |
|---|---|---|---|---|---|---|
| 0 | 0 | 0 | 0 | 0 | 0 | 0 |
| 1 | 7.04 | 11.26 | 5.62 | 5.74 | 8.61 | 8.98 |
| 2 | 16.59 | 24.4 | 13.28 | 13.39 | 19.69 | 20.58 |
| 3 | 26.69 | 38.12 | 20.99 | 20.83 | 31.23 | 31.96 |
| 4 | 38.02 | 52.75 | 29.47 | 28.94 | 43.42 | 43.46 |
| 5 | 50.56 | 66.73 | 38.99 | 37.84 | 56.09 | 54.97 |
| 6 | 63.31 | 79.25 | 49.47 | 47.76 | 68.35 | 66.08 |
| 7 | 74.98 | 88.78 | 60.68 | 58.06 | 78.89 | 76.22 |
| 8 | 84.71 | 95.41 | 72.25 | 68.75 | 86.79 | 84.81 |
| 9 | 91.92 | 99.42 | 81.02 | 77.34 | 92.06 | 89.75 |
| 10 | 96.47 | 101.76 | 86.63 | 83.99 | 95.01 | 92.56 |
| 11 | 99.45 | 103.05 | 90.01 | 87.32 | 96.72 | 94.64 |
| 12 | 101.21 | 103.86 | 92.45 | 90.03 | 97.77 | 95.52 |
| 13 | 102.36 | 104.25 | 94.27 | 92.21 | 98.49 | 96.58 |
| 14 | 103.38 | | 95.51 | 93.2 | 98.97 | 96.79 |
| 15 | 104.06 | | 96.61 | 94.45 | 99.34 | 97.45 |
| 16 | 104.77 | | 97.46 | 95.47 | 99.6 | 97.74 |

The stability of the tablet coated with formulation MD coated to 16% weight gain stored at 40° C./75% relative humidity (RH) was determined at periodic intervals over a 10 month period by determining the dissolution of the metformin under the following conditions:
Media: 900 ml water
Method: USP Type II Apparatus, 50 rpm at 37° C.
The dissolution data is presented in Table 5 as a % release into the medium of the total metformin HCl in the tablet:

TABLE 5

| Time (h) | 0 Month | 1 Month | 2 Month | 3 Month | 6 Month | 10 Month |
|---|---|---|---|---|---|---|
| 1 | 7 | 5.3 | 7.3 | 8.3 | 3.3 | 9.7 |
| 2 | 16.6 | 13.8 | 16.9 | 19.1 | 13.4 | 21.4 |
| 4 | 38 | 35 | 39.7 | 46.8 | 38 | 49.7 |
| 8 | 84.7 | 79 | 87.3 | 98.1 | 89.4 | 92.9 |
| 12 | 101.2 | 90.4 | 99.4 | 106.8 | 102.8 | 99.9 |

A comparative study was conducted to determine the bioavailability following administration of a single dose metformin tablet (Tables 6 and 7) or multiple-dose metformin tablet (Table 8) of the invention

TABLE 6

| Time (Hrs) | Metformin HCl 500 mg ER Tablets, q.d. (Lot # 00F167) | Metformin HCl 500 mg ER Tablets, q.d. (Lot #07(C)/00 500 XL-HT)) | Glucophage 500 mg, b.i.d. (Lot # C8J247A) |
|---|---|---|---|
| 0 | 0.00 ± 0.00 | 12.68 ± 39.85 | 2.51 ± 9.71 |
| 2 | 7.37 ± 15.46 | 53.96 ± 31.93 | 73.39 ± 59.00 |
| 4 | 343.92 ± 146.45 | 164.46 ± 65.57 | 200.20 ± 114.59 |
| 5 | 476.22 ± 151.89 | 176.46 ± 80.87 | 485.69 ± 188.37 |
| 6 | 390.96 ± 129.93 | 146.23 ± 65.48 | 630.49 ± 161.58 |
| 7 | 325.99 ± 104.84 | 116.62 ± 59.84 | 707.85 ± 215.67 |
| 8 | 284.59 ± 104.39 | 97.20 ± 51.97 | 651.46 ± 183.34 |
| 9 | 242.05 ± 95.88 | 85.26 ± 47.76 | 466.04 ± 128.06 |
| 10 | 204.51 ± 86.24 | 77.24 ± 43.17 | 259.19 ± 78.14 |
| 12 | 127.37 ± 62.84 | 49.53 ± 28.71 | 158.77 ± 42.42 |
| 16 | 60.11 ± 37.32 | 21.02 ± 19.97 | 55.69 ± 16.58 |
| 20 | 40.52 ± 30.87 | 15.63 ± 16.54 | 25.93 ± 19.96 |
| 24 | 19.64 ± 23.26 | 9.49 ± 14.00 | 6.01 ± 12.75 |

TABLE 7

| SUBJECT | Metformin HCl 500 mg ER Tablets, q.d. (Lot # 00F167) | | | Metformin HCl 500 mg ER Tablets, q.d. (Lot #07(C)/00 500 XL-HT)) | | | Glucophage 500 mg, b.i.d. (Lot # C8J247A) | | |
|---|---|---|---|---|---|---|---|---|---|
| | $C_{max}$ | $AUC_{0-t}$ | $T_{max}$ | $C_{max}$ | $AUC_{0-t}$ | $T_{max}$ | $C_{max}$ | $AUC_{0-t}$ | $T_{max}$ |
| 1 | 423.94 | 3203.04 | 5.0 | 296.51 | 1589.86 | 5.0 | 901.58 | 5608.64 | 3.0 |
| 2 | 357.51 | 4267.79 | 10.0 | — | — | — | — | — | — |
| 3 | 318.39 | 1602.89 | 5.0 | 216.55 | 1842.90 | 5.0 | 447.61 | 2971.16 | 5.0 |
| 4 | 489.60 | 2784.57 | 4.0 | 127.03 | 1447.85 | 4.0 | 510.26 | 3504.43 | 4.0 |
| 5 | 592.40 | 3864.41 | 5.0 | 166.35 | 1484.23 | 5.0 | 735.54 | 5394.77 | 4.0 |
| 6 | 414.96 | 2295.36 | 5.0 | 175.21 | 1285.79 | 5.0 | 686.09 | 4258.03 | 4.0 |
| 7 | 419.53 | 3619.34 | 5.0 | 191.15 | 1415.17 | 5.0 | 520.19 | 3435.10 | 3.0 |
| 8 | 227.86 | 1548.93 | 5.0 | 203.87 | 1373.32 | 4.0 | 806.18 | 5076.93 | 3.0 |
| 9 | 664.24 | 4366.66 | 5.0 | 187.89 | 1779.67 | 5.0 | 697.26 | 4994.51 | 2.0 |
| 10 | 583.18 | 3398.15 | 5.0 | 144.69 | 978.64 | 5.0 | 1002.36 | 6098.66 | 4.0 |
| 11 | 566.79 | 5048.15 | 6.0 | 173.95 | 1771.12 | 6.0 | 641.14 | 4709.57 | 5.0 |
| 12 | 573.18 | 3370.02 | 5.0 | 42.10 | 236.63 | 4.0 | 654.03 | 4208.54 | 4.0 |
| 13 | 302.20 | 2559.23 | 5.0 | 192.13 | 2090.60 | 5.0 | 586.54 | 4177.75 | 4.0 |
| 14 | — | — | — | 158.98 | 1152.05 | 4.0 | 1090.92 | 6671.03 | 5.0 |
| 16 | 625.70 | 4278.32 | 5.0 | 152.38 | 930.85 | 0.0 | 808.43 | 4882.53 | 4.0 |
| 19 | 640.76 | 3353.70 | 4.0 | 123.43 | 496.15 | 5.0 | 578.89 | 3108.53 | 2.0 |
| 20 | 768.94 | 4284.70 | 5.0 | 396.18 | 2689.22 | 5.0 | 1125.20 | 6308.03 | 4.0 |
| Mean | 498.1 | 3365.33 | 5.3 | 184.3 | 1410.25 | 4.5 | 737.0 | 4713.01 | 3.8 |
| SD | 151.9 | 1006.86 | 1.3 | 77.4 | 594.66 | 1.3 | 205.5 | 1133.00 | 0.9 |
| CV (%) | 30.5 | 29.92 | 25.6 | 42.0 | 42.17 | 29.3 | 27.9 | 24.04 | 24.8 |
| GeoMean | 474.1 | 3199.36 | 5.1 | 168.4 | 1247.38 | 4.8 | 711.4 | 4581.55 | 3.6 |
| Min | 227.86 | 1548.93 | 4.00 | 42.10 | 236.63 | 0.00 | 447.61 | 2971.16 | 2.00 |
| Max | 768.94 | 5048.15 | 10.00 | 396.18 | 2689.22 | 6.00 | 1125.20 | 6671.03 | 5.00 |

TABLE 8

| SUBJECT | Metformin HCl 500 mg ER Tablets, q.d. (Lot # 00F167) | | | Metformin HCl 500 mg ER Tablets, q.d. (Lot #07(C)/00 500 XL-HT)) | | | Glucophage 500 mg, b.i.d. (Lot # C8J247A) | | |
|---|---|---|---|---|---|---|---|---|---|
| | $C_{max}$ | $AUC_{0-\tau}$ | $T_{max}$ | $C_{max}$ | $ACU_{0-\tau}$ | $T_{max}$ | $C_{max}$ | $AUC_{0-\tau}$ | $T_{max}$ |
| 1 | 945.40 | 6232.57 | 5.0 | 872.61 | 5177.02 | 5.0 | 886.47 | 12899.68 | 3.0 |
| 3 | 722.90 | 8312.65 | 5.0 | 475.83 | 4403.99 | 5.0 | 628.12 | 10229.16 | 15.0 |
| 4 | 540.79 | 4332.49 | 4.0 | 155.28 | 1538.15 | 4.0 | 580.82 | 7692.77 | 3.0 |
| 5 | 1562.92 | 10130.87 | 5.0 | 401.35 | 3980.27 | 5.0 | 968.26 | 12011.86 | 3.0 |
| 6 | 770.21 | 5346.86 | 6.0 | 425.47 | 3514.28 | 4.0 | 821.17 | 10603.35 | 3.0 |
| 7 | 560.34 | 4490.96 | 5.0 | 409.97 | 3884.59 | 5.0 | 721.95 | 10518.02 | 4.0 |
| 8 | 1105.38 | 8133.56 | 5.0 | 442.39 | 4111.28 | 5.0 | 757.45 | 11971.60 | 4.0 |
| 9 | 727.04 | 4863.71 | 5.0 | 541.01 | 5228.69 | 5.0 | 977.96 | 12244.88 | 4.0 |
| 10 | 1150.00 | 7974.91 | 5.0 | 694.61 | 4673.33 | 5.0 | 1123.79 | 14656.81 | 4.0 |
| 11 | 983.35 | 6791.08 | 5.0 | 594.71 | 5228.49 | 6.0 | 817.43 | 10463.89 | 5.0 |
| 12 | 961.04 | 6548.23 | 5.0 | 454.24 | 4037.80 | 5.0 | 856.27 | 11769.61 | 4.0 |
| 13 | 963.88 | 8612.93 | 6.0 | 430.68 | 4788.57 | 5.0 | 734.24 | 12074.02 | 4.0 |
| 14 | — | — | — | 615.73 | 5939.67 | 5.0 | — | — | — |
| 16 | 990.87 | 5890.99 | 5.0 | 359.87 | 3273.11 | 5.0 | 567.54 | 7890.22 | 3.0 |
| 19 | 835.28 | 4797.61 | 4.0 | 368.31 | 2801.78 | 5.0 | 893.94 | 11735.13 | 4.0 |
| 20 | 3835.55 | 11037.19 | 6.0 | 774.96 | 6522.10 | 5.0 | 970.78 | 15109.04 | 6.0 |
| Mean | 1110.3 | 6899.77 | 5.1 | 501.1 | 4318.94 | 4.9 | 820.4 | 11458.00 | 4.6 |
| SD | 795.1 | 2072.53 | 0.6 | 176.3 | 1222.75 | 0.5 | 158.5 | 2042.45 | 3.0 |
| CV (%) | 71.6 | 30.04 | 11.7 | 35.2 | 28.31 | 10.3 | 19.3 | 17.83 | 65.1 |
| GeoMean | 973.3 | 6620.63 | 5.0 | 469.2 | 4119.36 | 4.8 | 805.7 | 11278.47 | 4.1 |
| Min | 540.79 | 4332.49 | 4.00 | 155.28 | 1538.15 | 4.00 | 567.54 | 7692.77 | 3.00 |
| Max | 3835.55 | 11037.19 | 6.00 | 872.61 | 6522.10 | 6.00 | 1123.79 | 15109.04 | 15.00 |

EXAMPLE 2

Bupropion HCl Tablets 2.1 Tablet Core Preparation

The following formulation was prepared for Bupropion HCl 300 mg and 150 mg strength tablets:

| Ingredients | % w/w |
|---|---|
| Bupropion HCl | 93.75 |
| Polyvinyl alcohol (PVA)* | 3.31 |
| Atomized Glyceryl Behenate** | 2.94 |
| Total | 100.00 |

**The PVA is prepared as a 4.6% solution (w/w) in purified water. The purified water is not considered as part of the theoretical batch size since it is evaporated during drying of the core in the fluid bed granulator.
*** Compritol 888 ATO The tablet cores were prepared as described above for oxycodone HCl. The granules were compressed into either 320 mg tablets (for 300 mg strength tablets) or 160 mg tablets (for 150 mg strength tablets). The dissolution profile of the compressed tablets was determined under the following conditions:

Medium: 900 ml water
Method: USP Type II Apparatus, 50 rpm at 37° C.

The release of bupropion HCl from the tablet cores was found to be about 100% in about 30 minutes.

2.2 Core Coating

The following four coating formulations were prepared for the bupropion HCl 300 mg strength tablet cores:

| Ingredients | BA (% w/w) | BB (% w/w) | BC (% w/w) | BD (% w/w) | BE (% w/w) |
|---|---|---|---|---|---|
| Eudrgit ® NE 30D (Liquid) | 26.82 | 26.82 | 26.82 | 26.82 | 26.82 |
| Talc 400 | 4.83 | 4.02 | 3.62 | 4.43 | 4.02 |
| Titanium Dioxide | 0.81 | 0.81 | 0.81 | 0.81 | 0.81 |
| HPMC | 2.01 | 2.82 | 3.22 | 2.41 | 2.82 |
| PEG 8000 | 2.01 | 2.01 | 2.01 | 2.01 | 2.01 |
| Simethicone | 0.2 | 0.2 | 0.2 | 0.2 | 0.2 |
| Tween ® 80 | 0.1 | 0.1 | 0.1 | 0.1 | 0.1 |
| Purified water | 63.22 | 63.22 | 63.22 | 63.22 | 63.22 |
| Total | 100.00 | 100.00 | 100.00 | 100.00 | 100.00 |

The following two coating formulations were prepared for the bupropion HCl 150 mg strength tablet cores:

| Ingredients | BF (w/w %) | BG (% w/w) |
|---|---|---|
| Eudrgit ® NE 30D (Liquid) | 26.82 | 26.82 |
| Talc 400 | 4.02 | 3.62 |
| Titanium Dioxide | 0.81 | 0.81 |
| HPMC 606 | 2.82 | 3.22 |
| PEG 8000 | 2.01 | 2.01 |
| Somethicone | 0.2 | 0.2 |
| Tween ® 80 | 0.1 | 0.1 |
| Purified water | 63.22 | 63.22 |
| Total | 100.00 | 100.00 |

The bupropion HCl 300 mg core tablets were coated with either one of the coat formulations BA-BE to 15% weight gain as described for the metformin HCl core tablets. Coated tablet cores were cured at 62±2° C. Dissolution tests of the coated tablet cores was carried out under the following dissolution conditions:

Medium: 900 ml 0.1N HCl or water
Method: USP Type I Apparatus, 75 rpm at 37° C.

The results are presented in Table 9 and 10 as a % release into 0.1N HCl and water respectively of the total bupropion HCl in the 300 mg tablet:

TABLE 9

| Time (h) | BB | BC | BD | BE |
|---|---|---|---|---|
| 0 | 0 | 0 | 0 | 0 |
| 1 | 2.6 | 4.18 | 1.73 | 2.2 |
| 2 | 5.9 | 9.03 | 4.23 | 4.58 |
| 3 | 9 | 14.3 | 6.44 | 6.62 |
| 4 | 12 | 19.89 | 8.43 | 10.25 |

TABLE 9-continued

| Time (h) | BB | BC | BD | BE |
|---|---|---|---|---|
| 5 | 15.5 | 27.23 | 10.44 | 12.93 |
| 6 | 19.3 | 33.14 | 12.6 | 16.65 |
| 7 | 23.7 | 40.45 | 14.9 | 20.43 |
| 8 | 28.5 | 46.81 | 17.32 | 24.39 |
| 9 | 33.7 | 52.46 | 20.04 | 29.24 |
| 10 | 39.1 | 59.59 | 23 | 34.72 |
| 11 | 44.5 | 64.57 | 26.3 | 38.98 |
| 12 | 49.9 | 69.7 | 29.84 | 44.62 |
| 13 | 55 | 74.6 | 33.66 | 47.26 |
| 14 | 59.9 | 78.17 | 37.69 | 51.94 |
| 15 | 64.5 | 81.99 | 41.85 | 56.03 |
| 16 | 69 | 85.05 | 46.37 | 60.72 |
| 17 |  | 88.58 | 50.72 | 63.61 |
| 18 |  | 91.14 | 54.7 | 67.4 |
| 19 |  | 92.25 | 58.4 | 70.4 |
| 20 |  | 93.62 | 62.1 | 73.93 |
| 21 |  | 94.86 | 65.6 | 76.55 |
| 22 |  | 95.72 | 68.9 | 77.86 |
| 23 |  | 96.25 | 72.1 | 79.97 |
| 24 |  | 96.69 | 75.1 | 82.32 |

TABLE 10

| Time (h) | BA | BB | BC | BD | BE |
|---|---|---|---|---|---|
| 0 | 0 | 0 | 0 | 0 | 0 |
| 1 | 1 | 1.97 | 4.62 | 1.6 | 2.4 |
| 2 | 2.5 | 4.65 | 8.73 | 3.6 | 5.1 |
| 3 | 3.8 | 7.3 | 12.7 | 5.3 | 7.3 |
| 4 | 4.8 | 9.93 | 17.09 | 6.8 | 9.3 |
| 5 | 5.8 | 12.73 | 21.96 | 8.2 | 11.4 |
| 6 | 6.7 | 16 | 27.37 | 9.6 | 13.5 |
| 7 | 7.6 | 19.3 | 33.18 | 11 | 15.8 |
| 8 | 8.5 | 22.5 | 39.22 | 12.5 | 18.3 |
| 9 | 9.4 | 26 | 45.16 | 14 | 21 |
| 10 | 10.3 | 29.1 | 50.78 | 15.7 | 23.9 |
| 11 | 11.2 | 33.2 | 56.13 | 17.5 | 27.15 |
| 12 | 12.3 | 36.7 | 61.09 | 19.5 | 30.52 |
| 13 | 13.4 | 40.7 | 65.72 | 21.7 | 34.11 |
| 14 | 14.6 | 44.5 | 69.95 | 24.2 | 37.89 |
| 15 | 15.8 | 47.8 | 73.76 | 26.8 | 41.58 |
| 16 | 17.2 | 51.5 | 77.15 | 29.8 | 45.27 |
| 17 |  | 54.9 | 80.1 | 33.3 | 48.91 |
| 18 |  | 58.6 | 82.65 | 37.1 | 52.59 |
| 19 |  | 61.7 | 84.75 | 40.7 | 56.06 |
| 20 |  | 64.7 | 86.51 | 45.6 | 59.35 |
| 21 |  | 68.2 | 87.97 | 50.1 | 62.5 |
| 22 |  | 71.4 | 89.15 | 53.8 | 65.67 |
| 23 |  | 74.3 | 90.12 | 57.3 | 68.49 |
| 24 |  | 77 | 90.96 | 60.4 | 71.1 |

The 150 mg tablet cores were coated with formulations BF and BG to to 15% and 25% weight gain respectively and dissolution tests were performed on these tablets under the following conditions:

Media: 900 ml 0.1N HCl
Method: USP Type I Apparatus, 75 rpm at 37° C.

The dissolution data is presented in Table 11 as a % release into the medium of the total bupropion HCl:

TABLE 11

| Time (h) | BG (25% weight gain) | BF (15% weight gain) |
|---|---|---|
| 0 | 0 | 0 |
| 1 | 1.61 | 2.89 |
| 2 | 5.75 | 6.9 |
| 3 | 9.89 | 10.83 |
| 4 | 14.3 | 15.3 |
| 5 | 19.3 | 20.38 |
| 6 | 24.58 | 25.98 |

TABLE 11-continued

| Time (h) | BG (25% weight gain) | BF (15% weight gain) |
|---|---|---|
| 7 | 29.97 | 31.91 |
| 8 | 35.18 | 37.86 |
| 9 | 40.18 | 43.79 |
| 10 | 44.87 | 49.29 |
| 11 | 49.33 | 54.64 |
| 12 | 53.55 | 59.58 |
| 13 | 57.49 | 64.28 |
| 14 | 61.33 | 68.63 |
| 15 | 64.87 | 72.65 |
| 16 | 68.24 | 76.34 |
| 17 | 71.41 | 79.71 |
| 18 | 74.32 | 82.7 |
| 19 | 77.05 | 85.31 |
| 20 | 79.55 | 87.52 |
| 21 | 81.84 | 89.38 |
| 22 | 83.92 | 90.97 |
| 23 | 85.64 | 92.34 |
| 24 | 87.31 | 93.47 |

The stability of the tablet coated with formulation BG supplemented with 0.65% titanium dioxide and 0.12% synthetic iron oxide pigment. The tablet was coated to 20% weight gain stored at 40° C./75% relative humidity (RH) was determined at periodic intervals over a 3 month period by determining the dissolution of the bupropion under the following conditions:
Media: 900 ml 0.1N HCl
Method: USP Type I Apparatus, 75 rpm at 37° C.
The dissolution data is presented in Table 12 as a % release into the medium of the total bupropion HCl in the tablet:

TABLE 12

| Time (h) | 0 Month | 1 Month | 3 Month |
|---|---|---|---|
| 2 | 6.0 | 6.2 | 6.4 |
| 4 | 14.4 | 15.3 | 15.7 |
| 8 | 36.6 | 41.0 | 42.1 |
| 16 | 72.8 | 82.6 | 84.2 |
| 24 | 92.3 | 99.4 | 93.6 |

A comparative study was conducted to determine the bioavailability following administration of a single dose bupropion tablet (Tables 13 and 14) the invention

TABLE 13

| Time (Hrs) | Bupropion HCl 150 mg ER Tablets. (Lot # Bup-Bio (AQ) 02C-02/150-NE) | Bupropion HCl 150 mg ER Tablets. (Lot # Bup-Bio (AQ) 03A-02/150-S) | Bupropion HCl XL Tablets, 150 mg. (Lot # 02A063) |
|---|---|---|---|
| 0 | 0.00 ± 0.00 | 0.00 ± 0.00 | 0.00 ± 0.00 |
| 0.5 | 0.00 ± 0.00 | 0.00 ± 0.00 | 0.00 ± 0.00 |
| 1 | 0.14 ± 0.51 | 0.00 ± 0.00 | 0.00 ± 0.00 |
| 1.5 | 1.37 ± 1.55 | 0.00 ± 0.00 | 0.00 ± 0.00 |
| 2 | 4.27 ± 2.25 | 0.00 ± 0.00 | 0.81 ± 1.64 |
| 2.5 | 7.14 ± 2.76 | 0.43 ± 0.60 | 3.25 ± 3.40 |
| 3 | 9.55 ± 3.57 | 1.15 ± 0.96 | 11.56 ± 10.81 |
| 3.5 | 11.49 ± 4.68 | 2.35 ± 1.72 | 22.75 ± 16.54 |
| 4 | 12.12 ± 4.91 | 3.26 ± 2.25 | 30.24 ± 18.87 |
| 4.5 | 13.35 ± 5.35 | 5.37 ± 4.20 | 39.88 ± 23.52 |
| 5 | 17.35 ± 6.80 | 7.27 ± 3.59 | 53.42 ± 20.15 |
| 5.5 | 17.40 ± 6.69 | 8.53 ± 3.34 | 60.76 ± 19.45 |
| 6 | 16.07 ± 5.48 | 9.40 ± 3.82 | 62.08 ± 18.83 |
| 8 | 13.00 ± 5.34 | 8.98 ± 4.17 | 46.47 ± 16.36 |
| 10 | 22.40 ± 10.48 | 16.39 ± 20.64 | 44.23 ± 15.86 |
| 12 | 34.46 ± 13.26 | 18.57 ± 13.43 | 35.14 ± 15.55 |
| 16 | 28.01 ± 9.36 | 27.36 ± 15.05 | 20.40 ± 6.96 |
| 24 | 17.87 ± 8.27 | 19.81 ± 8.32 | 10.11 ± 3.58 |
| 36 | 6.76 ± 3.93 | 8.51 ± 7.13 | 4.94 ± 1.58 |
| 48 | 3.51 ± 1.36 | 4.01 ± 2.26 | 3.41 ± 1.66 |
| 72 | 1.35 ± 0.88 | 1.65 ± 0.83 | 1.21 ± 0.90 |
| 96 | 0.19 ± 0.46 | 0.35 ± 0.55 | 0.21 ± 0.51 |
| 120 | 0.00 ± 0.00 | 0.00 ± 0.00 | 0.00 ± 0.00 |

TABLE 14

| | Bupropion HCl 150 mg ER Tablets. (Lot # Bup-Bio (AQ) 02C-02/150-NE) | | | Bupropion HCl 150 mg ER Tablets. (Lot # Bup-Bio (AQ) 03A-02/150-S) | | | Bupropion HCl XL Tablets, 150 mg. (Lot # 02A063) | | |
|---|---|---|---|---|---|---|---|---|---|
| SUBJECT | AUC | CMAX | TMAX | AUC | CMAX | TMAX | AUC | CMAX | TMAX |
| 1 | 783.88 | 27.72 | 24.0 | 637.03 | 36.23 | 12.0 | 654.49 | 74.73 | 5.5 |
| 2 | 366.41 | 28.05 | 12.0 | 550.51 | 30.78 | 16.0 | 534.11 | 53.70 | 6.0 |
| 3 | 1179.19 | 52.75 | 16.0 | 1223.27 | 86.66 | 10.0 | 1223.86 | 91.77 | 6.0 |
| 4 | 789.01 | 44.01 | 12.0 | 167.84 | 17.49 | 4.5 | 954.87 | 106.52 | 5.5 |
| 5 | 730.90 | 44.92 | 10.0 | 518.11 | 29.30 | 16.0 | 881.67 | 62.52 | 6.0 |
| 7 | 577.62 | 27.97 | 16.0 | 577.76 | 24.60 | 24.0 | 677.27 | 54.21 | 10.0 |
| 8 | 1095.68 | 32.75 | 24.0 | 1094.55 | 32.36 | 24.0 | 1098.80 | 75.11 | 10.0 |
| 9 | 494.33 | 23.05 | 12.0 | 495.00 | 17.49 | 16.0 | 440.79 | 43.58 | 5.5 |
| 10 | 1000.63 | 35.30 | 16.0 | 911.09 | 35.40 | 24.0 | 1093.05 | 70.28 | 5.5 |
| 12 | 837.22 | 32.33 | 12.0 | 877.09 | 23.13 | 36.0 | 747.36 | 50.07 | 5.0 |
| 13 | 855.14 | 46.38 | 12.0 | 911.36 | 58.44 | 16.0 | 836.02 | 69.49 | 6.0 |
| 14 | 806.11 | 55.63 | 12.0 | 572.52 | 21.93 | 16.0 | 1050.24 | 85.35 | 8.0 |
| 15 | 612.93 | 27.04 | 16.0 | 717.12 | 36.47 | 16.0 | 613.25 | 72.73 | 5.5 |
| 16 | 654.03 | 57.51 | 12.0 | 699.39 | 23.97 | 16.0 | 1082.74 | 71.07 | 6.0 |
| Mean | 770.22 | 38.24 | 14.71 | 710.90 | 33.87 | 17.61 | 849.18 | 70.08 | 6.46 |
| Std. Dev | 224.61 | 11.70 | 4.41 | 272.38 | 18.43 | 7.55 | 243.23 | 17.02 | 1.65 |
| CV (%) | 29.16 | 30.58 | 29.97 | 38.32 | 54.41 | 42.85 | 28.64 | 24.29 | 25.47 |
| GeoMean | 737.74 | 36.63 | 14.20 | 650.74 | 30.60 | 16.00 | 814.20 | 68.19 | 6.30 |
| Min | 366.41 | 23.05 | 10.00 | 167.84 | 17.49 | 4.50 | 440.79 | 43.58 | 5.00 |
| Max | 1179.19 | 57.51 | 24.00 | 1223.27 | 86.66 | 36.00 | 1223.86 | 106.52 | 10.00 |

EXAMPLE 3

Tramadol HCl Tablets

3.1 Tablet Core Preparation

The following formulation was prepared for tramadol HCl 40 mg or 80 mg strength tablets:

| Ingredients | % w/w | % w/w |
|---|---|---|
| Tramadol HCl | 40.0 | 80.0 |
| Silicon Dioxide* | 0.4 | 0.4 |
| Polyvinyl alcohol (PVA)** | 1.1 | 0.9 |
| Lactose Anhydrous DT | 56.5 | 16.69 |
| Atomized Glyceryl Behenate*** | 2.00 | 2.00 |
| Total | 100.00 | 100.00 |

*Aerosil 200.
**The PVA is prepared as a 3.8% solution (w/w) in purified water. The purified water is not considered as part of the theoretical batch size since it is evaporated during drying of the core in the fluid bed granulator.
***Compritol 888 ATO All of the ingredients were transferred into a V-blender and processed as described above for metformin HCl. The granules were subsequently compressed into tablets.

The dissolution profile of the compressed tablet cores was determined under following conditions:

Medium: 900 ml water

Method: USP Type II Apparatus, 75 rpm at 37° C.

The tablet cores are immediate release. The release of tramadol HCl from the tablet cores was found to be 100% in about 30 min.

3.2 Core Coating

The following four coat formulations were prepared:

| Ingredients | TA (% w/w) | TB (% w/w) | TC (% w/w) | TD (% w/w) |
|---|---|---|---|---|
| Eudrgit ® NE 30D (Liquid) | 38.5 | 33.3 | 27.74 | 28.82 |
| Talc 400 | 4.7 | 4.21 | 4.14 | 4.32 |
| Titanium Dioxide | 1.6 | 1.35 | 1.2 | 1.24 |
| HPMC 606 | 1.4 | 1.35 | 1.02 | 1.05 |
| PEG 8000 | 0 | 1.18 | 0 | 0.43 |
| Simethicone | 0.32 | 0.25 | 0.2 | 0.21 |
| Tween ® 80 | 0.24 | 0.2 | 0.12 | 0.12 |
| Purified water | 53.24 | 58.16 | 65.58 | 63.81 |
| Total | 100 | 100 | 100 | 100 |

The coating procedure was carried out as described above for metformin HCl tablet cores. Coated tablet cores were cured at 62±° C. for about 2 hours.

The tramadol tablet cores were coated with either one of the coating formulations TA, TB, TC, and TD. The coating was applied to a weight gain of approximately 8% to about 18%. Curing temperatures ranged from about 60° C. to about 65° C. and curing times were for either 3 or 4 hours. Dissolution tests were carried out as follows:

Medium: 900 ml 0.1N HCl (pH 1.2)

Method: USP Type I Apparatus, 75 rpm at 37° C.

The dissolution data is presented in Table 15 as a % release into the medium of the total tramadol HCl:

TABLE 15

| Time (h) | TD (8% weight gain, cured at 65° C. for 3 hrs) | TC (8% weight gain, cured at 60° C. for 3 hrs) | TB (13% weight gain, cured at 60° C. for 4 hrs) | TA (18% weight gain, cured at 60° C. for 3 hrs) |
|---|---|---|---|---|
| 0 | 0 | 0 | 0 | 0 |
| 1 | 1.15 | 1.64 | 0.29 | 1.31 |
| 2 | 3.05 | 5.16 | 0.44 | 1.94 |
| 3 | 5.48 | 10.83 | 0.89 | 2.5 |
| 4 | 8.32 | 21.09 | 1.73 | 3.23 |
| 5 | 11.26 | 37.21 | 2.89 | 3.92 |
| 6 | 15.07 | 51.97 | 4.1 | 4.93 |
| 7 | 20 | 65.54 | 5.32 | 5.94 |
| 8 | 25.01 | 76.21 | 6.55 | 6.97 |
| 9 | 30.96 | 83.67 | 7.92 | 8.24 |
| 10 | 36.99 | 90.23 | 9.22 | 9.65 |
| 11 | 43.48 | 94.47 | 10.58 | 12.1 |
| 12 | 49.4 | 97.8 | 12.07 | 17.08 |
| 13 | 55.33 | 100.02 | 13.55 | 21.78 |
| 14 | 60.97 | 101.6 | 15.25 | 31.93 |
| 15 | 66.43 | 102.66 | 17.02 | 38.89 |
| 16 | 71.33 | 103.39 | 19.12 | 44.12 |
| 17 | 76.25 | 103.92 | 21.3 | 48.31 |
| 18 | 80.54 | — | 23.76 | 52.18 |
| 19 | 84.05 | — | 26.36 | 55.78 |
| 20 | 87.18 | — | 28.93 | 58.96 |
| 21 | 89.85 | — | 31.48 | 61.62 |
| 22 | 91.87 | — | — | 64.63 |
| 23 | 93.65 | — | — | 66.97 |
| 24 | 95.2 | — | — | 69.54 |

Tablets coated with formulation TC were cured at either 60° C. for 3 hrs or for 22 hrs or at 70° C. for 3 hrs. Dissolution tests were conducted as follows:

Media: 900 ml 0.1N HCl

Method: USP Type I Apparatus, 75 rpm at 37° C.

The dissolution data is presented in Table 16 as a % release into the medium of the total tramadol HCl:

TABLE 16

| Time (h) | TC cured at 60° C. for 22 hrs | TC cured at 70° C. for 3 hrs. | TC cured at 60° C. for 3 hrs |
|---|---|---|---|
| 0 | 0 | 0 | 0 |
| 1 | 1.4032 | 1.3888 | 1.64 |
| 2 | 3.9566 | 3.8022 | 5.16 |
| 3 | 7.9378 | 7.3746 | 10.83 |
| 4 | 13.631 | 12.784 | 21.09 |
| 5 | 21.956 | 20.607 | 37.21 |
| 6 | 32.55 | 31.338 | 51.97 |
| 7 | 44.124 | 42.846 | 65.54 |
| 8 | 54.9 | 53.873 | 76.21 |
| 9 | 64.3 | 63.568 | 83.67 |
| 10 | 73 | 71.219 | 90.23 |
| 11 | 79.5 | 77.418 | 94.47 |
| 12 | 84 | 82.787 | 97.8 |
| 13 | 88.5 | 86.683 | 100.02 |
| 14 | 91.5 | 89.748 | 101.6 |
| 15 | 94 | 92.209 | 102.66 |
| 16 | 96 | 94.006 | 103.39 |
| 17 | 97.7 | 95.484 | 103.92 |
| 18 | 98.9 | 96.959 | |
| 19 | 100 | 97.853 | |
| 20 | 100.6 | 98.695 | |
| 21 | 101.4 | 99.294 | |
| 22 | 101.9 | | |
| 23 | 102.4 | | |
| 24 | 102.6 | | |

The 80 mg tramadol tablet core was coated to about 8% weight gain with formulation TD and cured at about 65° C. for about 3 hours. Dissolution tests on the tablets was conducted under the following conditions:

Media: 900 ml, 0.1N HCl, pH 5.8 phosphate buffer or pH 6.8 phosphate buffer.

Method: USP Type I Apparatus, 75 rpm at 37° C.

The dissolution data is presented in Table 17 as a % release into the medium of the total tramadol HCl:

TABLE 17

| Time (h) | TD-pH 1.2 | TD-pH 5.8 | TD-pH 6.8 |
|---|---|---|---|
| 0 | 0 | 0 | 0 |
| 1 | 0.58 | 0.5 | 0.44 |
| 2 | 1.49 | 1.96 | 1.61 |
| 3 | 2.66 | 3.81 | 2.84 |
| 4 | 4.12 | 6.2 | 4.58 |
| 5 | 6.18 | 7.79 | 6.99 |
| 6 | 9.34 | 12.6 | 11.16 |
| 7 | 14.43 | 18.73 | 19.19 |
| 8 | 22.98 | 28.78 | 32.31 |
| 9 | 34.85 | 42.14 | 48.55 |
| 10 | 49.13 | 55.48 | 62.39 |
| 11 | 62.65 | 65.45 | 71.68 |
| 12 | 73.37 | 72.39 | 78.03 |
| 13 | 81.08 | 77.11 | 82.39 |
| 14 | 85.36 | 80.71 | 85.52 |
| 15 | 88.37 | 83.36 | 87.77 |
| 16 | 90.66 | 85.54 | 89.72 |
| 17 | 92.34 | 87.33 | 91.14 |
| 18 | 93.79 | 88.83 | 92.42 |
| 19 | 94.92 | 89.9 | 93.44 |
| 20 | 95.74 | 91.04 | 94.3 |
| 21 | 96.36 | 91.72 | 95.08 |
| 22 | 96.97 | 92.63 | 95.65 |
| 23 | 97.51 | 93.11 | 96.25 |
| 24 | 97.94 | 93.68 | 96.78 |

EXAMPLE 4

Venlafaxine HCl Tablets

Tablet Core Preparation

The following formulation was prepared for Venlafaxine 150 mg strength tablets:

| Ingredients | % w/w |
|---|---|
| Venlafaxine HCl* | 54.05 |
| Xanthan Gum** | 22.29 |
| Polyvinylpyrrolidone (PVP)*** | 5.73 |
| Hydroxypropylmethylcellulose**** | 15.90 |
| Sodium Stearyl Fumarate N.F. | 2.00 |
| Isopropyl Alcohol 99% | |
| Total | 100.00 |

*Venlafaxine was calculated based on the base of Venlafaxine HCl, which has a content of 89 to 88.5% w/w based on Vanlafaxine HCl.
**Xantural 180
***Plasdone K29/32. The PVP is prepared as a 13.85% solution in Isopropyl Alcohol. The Isopropyl Alcohol is not considered part of the theoretical batch size since it is evaporated during drying of the core in the fluid bed granulator.
****Methocel Premium E3 LV With the exception of the sodium stearyl fumarate, all of the remaining ingredients were transferred into a high shear mixer/granulator such as a Fileder PMA 65 or Robot Coupe® RSI 10VB. The mixture is dry mixed at an impeller speed of 200-400 rpm and chopper speed of 0-300 rpm for 5 minutes. While the impeller and chopper are running the PVP solution is added to the high shear mixer and the mixture mixed for about 1-3 minutes.

The granulate is next dried at 55±5° C. to achieve a loss on drying (LOD) of less than about 2% of the granules.

The granules are next passed through a Comil with a 0.062 inch opening screen and the milled granules are loaded into a V-blender. At this point the sodium stearyl fumarate is added to the granules in the V-blender and the entire mixture is now blended for about 10 minutes. The blended granules are subsequently compressed into tablets.

The dissolution profile of the compressed venlafaxine tablet cores was determined under the following conditions:

Medium: 1000 ml water

Method: USP Type I Apparatus, 40 mesh, 75 rpm at 37° C.

The dissolution data is presented in the Table 18 as a % w/w release of venlafaxine from the tableted cores:

TABLE 18

| Time (hr) | VEN 150 mg tablet core tablets |
|---|---|
| 0 | 0 |
| 0.25 | 11 |
| 0.5 | 19 |
| 0.75 | 31 |
| 1 | 37 |
| 2 | 54 |
| 3 | 66 |
| 4 | 76 |
| 5 | 83 |
| 6 | 87 |
| 7 | 90 |
| 8 | 92 |
| 9 | 94 |
| 10 | 96 |

The tableted venlafaxine cores are sustained release with about 100% of the venlafaxine released in about 10 hrs.

Coating

The venlafaxine tablet cores are next coated with coating formulations F-1, F-2, and F-3 as shown in the table below to a weight gain of about 8%, 11%, 15% and 18% w/w by weight of the tablet core and cured in an oven at about 63±3° C. for about 3 hours:

| Ingredients | F-1 | F-2 | F-3 |
|---|---|---|---|
| Eudragit ® NE 30D | 26.87 | 26.87 | 26.87 |
| Talc 400 | 4.03 | 5.04 | 6.05 |
| Titanium Dioxide | 0.77 | 0.77 | 0.77 |
| Pharmacoat ® 606 (HPMC) | 2.82 | 2.82 | 2.82 |
| PEG 8000 | 2.02 | 1.01 | 0 |
| Somethicone | 0.2 | 0.2 | 0.2 |
| Tween ® 80 (Polysorbate 80) | 0.1 | 0.1 | 0.1 |
| Purified water | 63.19 | 63.19 | 63.19 |
| Total | 100 | 100 | 100 |

Dissolution tests were performed on each of the tablet cores coated with coat formulations F-1, F-2 and F-3 for each of the 8, 11, 15 and 18% weight gains under the following conditions:

Medium: 1000 ml water

Method: USP Type I Apparatus, 40 mesh, 75 rpm at 37° C.

The dissolution data are presented in Tables 19-21:

TABLE 19

| Time (hr) | F-1-8.3% | F-1-11.5% | F-1-15.3% | F-1-18.3% |
|---|---|---|---|---|
| 0 | 0 | 0 | 0 | 0 |
| 1 | 7 | 5 | 2 | 1 |
| 2 | 18 | 12 | 7 | 1 |
| 3 | 31 | 21 | 13 | 7 |
| 4 | 43 | 32 | 21 | 12 |
| 5 | 67 | 50 | 31 | 19 |
| 6 | 78 | 72 | 47 | 32 |
| 7 | 83 | 80 | 66 | 43 |
| 8 | 86 | 84 | 77 | 63 |
| 9 | 89 | 87 | 81 | 71 |
| 10 | 91 | 90 | 84 | 75 |

TABLE 19-continued

| Time (hr) | F-1-8.3% | F-1-11.5% | F-1-15.3% | F-1-18.3% |
|---|---|---|---|---|
| 11 | 94 | 91 | 86 | 79 |
| 12 | 96 | 92 | 87 | 83 |
| 13 | 98 | 93 | 89 | 87 |
| 14 | 100 | 94 | 90 | 89 |
| 15 | 102 | 95 | 93 | 91 |
| 16 | 102 | 96 | 95 | 93 |
| 17 | 102 | 97 | 96 | 95 |
| 18 | 103 | 98 | 97 | 97 |
| 19 | 103 | 100 | 99 | 99 |
| 20 | 103 | 100 | 99 | 100 |

TABLE 20

| Time (hr) | F-2-8.3% | F-2-11.5% | F-2-15.3% | F-2-18.3% |
|---|---|---|---|---|
| 0 | 0 | 0 | 0 | 0 |
| 1 | 2 | 1 | 1 | 0 |
| 2 | 8 | 4 | 2 | 1 |
| 3 | 16 | 10 | 6 | 3 |
| 4 | 26 | 16 | 10 | 6 |
| 5 | 47 | 28 | 17 | 9 |
| 6 | 62 | 53 | 28 | 13 |
| 7 | 69 | 64 | 50 | 18 |
| 8 | 74 | 68 | 58 | 31 |
| 9 | 78 | 72 | 63 | 45 |
| 10 | 81 | 75 | 67 | 54 |
| 11 | 85 | 77 | 70 | 58 |
| 12 | 87 | 80 | 72 | 61 |
| 13 | 89 | 82 | 75 | 64 |
| 14 | 91 | 84 | 77 | 66 |
| 15 | 92 | 85 | 79 | 68 |
| 16 | 94 | 87 | 81 | 70 |
| 17 | 95 | 89 | 83 | 72 |
| 18 | 96 | 90 | 85 | 73 |
| 19 | 96 | 91 | 86 | 74 |
| 20 | 97 | 92 | 88 | 76 |

TABLE 21

| Time (hr) | F-3-8.3% | F-3-11.5% | F-3-15.3% | F-3-18.3% |
|---|---|---|---|---|
| 0 | 0 | 0 | 0 | 0 |
| 1 | 3 | 1 | 0 | 0 |
| 2 | 15 | 5 | 3 | 1 |
| 3 | 28 | 16 | 9 | 4 |
| 4 | 39 | 28 | 20 | 11 |
| 5 | 49 | 38 | 29 | 21 |
| 6 | 58 | 47 | 38 | 30 |
| 7 | 64 | 55 | 46 | 38 |
| 8 | 71 | 62 | 53 | 45 |
| 9 | 76 | 68 | 59 | 52 |
| 10 | 80 | 73 | 65 | 58 |
| 11 | 83 | 78 | 70 | 63 |
| 12 | 87 | 82 | 75 | 69 |
| 13 | 91 | 85 | 79 | 72 |
| 14 | 93 | 88 | 82 | 78 |
| 15 | 95 | 90 | 85 | 81 |
| 16 | 97 | 93 | 88 | 83 |
| 17 | 98 | 94 | 91 | 85 |
| 18 | 99 | 96 | 93 | 87 |
| 19 | 100 | 97 | 94 | 89 |
| 20 | 101 | 98 | 95 | 91 |

As mentioned above, the prior art teaches that conditions or ingredients which increase the viscosity of Eudragit® NE30D films such as the addition of plasticizers and/or high temperatures can be detrimental to the functionality of Eudragit® NE30D films. However, in stark contrast to the teachings of the prior art, the inventors have surprisingly found, as shown by the examples below, that certain uses of poly glycols with a melting point of greater than 55° C. can impart beneficial characteristics not appreciated in the prior art. The amount of the poly glycol to be incorporated into the coating formulation of certain embodiments varies from about 1% to about 35% by weight of the coat.

In this example, the PEG contents are 25%, 12.5% and 0% based on dry Eudragit® NE 30D, in formulation F-1, F-2 and F-3 respectively. The formulations F-1, F-2 and F-3 (Tables 22 and 23) have the same composition, except that the lesser amounts of PEG in the F-2 and F-3 formulations are replaced by additional amounts of Talc 400 (an inert glidant).

TABLE 22

Dissolution data of the formulation F-2 vs. F-3

| Time (hr) | F-2-8.3% (PEG 12.5%) | F-2-11.5% (PEG 12.5%) | F-2-15.3% (PEG 12.5%) | F-2-18.3% (PEG 12.5%) | F-3-8.3% (PEG 0%) | F-3-11.5% (PEG 0%) | F-3-15.3% (PEG 0%) | F-3-18.3% (PEG 0%) |
|---|---|---|---|---|---|---|---|---|
| 0 | 0 | 0 | 0 | 0 | 0 | 0 | 0 | 0 |
| 1 | 2 | 1 | 1 | 0 | 3 | 1 | 0 | 0 |
| 2 | 8 | 4 | 2 | 1 | 15 | 5 | 3 | 1 |
| 3 | 16 | 10 | 6 | 3 | 28 | 16 | 9 | 4 |
| 4 | 26 | 16 | 10 | 6 | 39 | 28 | 20 | 11 |
| 5 | 47 | 28 | 17 | 9 | 49 | 38 | 29 | 21 |
| 6 | 62 | 53 | 28 | 13 | 58 | 47 | 38 | 30 |
| 7 | 69 | 64 | 50 | 18 | 64 | 55 | 46 | 38 |
| 8 | 74 | 68 | 58 | 31 | 71 | 62 | 53 | 45 |
| 9 | 78 | 72 | 63 | 45 | 76 | 68 | 59 | 52 |
| 10 | 81 | 75 | 67 | 54 | 80 | 73 | 65 | 58 |
| 11 | 85 | 77 | 70 | 58 | 83 | 78 | 70 | 63 |
| 12 | 87 | 80 | 72 | 61 | 87 | 82 | 75 | 69 |
| 13 | 89 | 82 | 75 | 64 | 91 | 85 | 79 | 72 |

TABLE 22-continued

Dissolution data of the formulation F-2 vs. F-3

| Time (hr) | F-2-8.3% (PEG 12.5%) | F-2-11.5% (PEG 12.5%) | F-2-15.3% (PEG 12.5%) | F-2-18.3% (PEG 12.5%) | F-3-8.3% (PEG 0%) | F-3-11.5% (PEG 0%) | F-3-15.3% (PEG 0%) | F-3-18.3% (PEG 0%) |
|---|---|---|---|---|---|---|---|---|
| 14 | 91 | 84 | 77 | 66 | 93 | 88 | 82 | 78 |
| 15 | 92 | 85 | 79 | 68 | 95 | 90 | 85 | 81 |
| 16 | 94 | 87 | 81 | 70 | 97 | 93 | 88 | 83 |
| 17 | 95 | 89 | 83 | 72 | 98 | 94 | 91 | 85 |
| 18 | 96 | 90 | 85 | 73 | 99 | 96 | 93 | 87 |
| 19 | 96 | 91 | 86 | 74 | 100 | 97 | 94 | 89 |
| 20 | 97 | 92 | 88 | 76 | 101 | 98 | 95 | 91 |

The dissolution data shows that the F-2 formulation (12.5% PEG) had a slower drug release rate compared to the F-3 formulation (0% PEG) with same coating weight gain.

TABLE 23

Dissolution data of the formulation F-2 vs. F-1

| Time (hr) | F-2-8.3% (PEG 12.5%) | F-2-11.5% (PEG 12.5%) | F-2-15.3% (PEG 12.5%) | F-2-18.3% (PEG 12.5%) | F-1-8.3% (PEG 25%) | F-1-11.5% (PEG 25%) | F-1-15.3% (PEG 25%) | F-1-18.3% (PEG 25%) |
|---|---|---|---|---|---|---|---|---|
| 0 | 0 | 0 | 0 | 0 | 0 | 0 | 0 | 0 |
| 1 | 2 | 1 | 1 | 0 | 7 | 5 | 2 | 1 |
| 2 | 8 | 4 | 2 | 1 | 18 | 12 | 7 | 1 |
| 3 | 16 | 10 | 6 | 3 | 31 | 21 | 13 | 7 |
| 4 | 26 | 16 | 10 | 6 | 43 | 32 | 21 | 12 |
| 5 | 47 | 28 | 17 | 9 | 67 | 50 | 31 | 19 |
| 6 | 62 | 53 | 28 | 13 | 78 | 72 | 47 | 32 |
| 7 | 69 | 64 | 50 | 18 | 83 | 80 | 66 | 43 |
| 8 | 74 | 68 | 58 | 31 | 86 | 84 | 77 | 63 |
| 9 | 78 | 72 | 63 | 45 | 89 | 87 | 81 | 71 |
| 10 | 81 | 75 | 67 | 54 | 91 | 90 | 84 | 75 |
| 11 | 85 | 77 | 70 | 58 | 94 | 91 | 86 | 79 |
| 12 | 87 | 80 | 72 | 61 | 96 | 92 | 87 | 83 |
| 13 | 89 | 82 | 75 | 64 | 98 | 93 | 89 | 87 |
| 14 | 91 | 84 | 77 | 66 | 100 | 94 | 90 | 89 |
| 15 | 92 | 85 | 79 | 68 | 102 | 95 | 93 | 91 |
| 16 | 94 | 87 | 81 | 70 | 102 | 96 | 95 | 93 |
| 17 | 95 | 89 | 83 | 72 | 102 | 97 | 96 | 95 |
| 18 | 96 | 90 | 85 | 73 | 103 | 98 | 97 | 97 |
| 19 | 96 | 91 | 86 | 74 | 103 | 100 | 99 | 99 |
| 20 | 97 | 92 | 88 | 76 | 103 | 100 | 99 | 100 |

The dissolution data shows that the F-1 formulation (25% PEG) had a faster drug release rate compared to the F-2 formulation (12.5% PEG) with same coating weight gain.

Film Elasticity and Strength Test

In order to evaluate the influence of PEG on the elasticity and strength of the coating films, a test was designed. The film elasticity of the coated tablets was evaluated by measuring the tablet diameter over time as the tablets hydrated upon exposure to water. The film strength was evaluated by measuring the film cracking or the tablet burst time.

Three tablets taken from the formulations F-1, F-2 and F-3 were put into 150 ml of water contained in a 250 ml glass beaker respectively, and allowed to sit for 24 hours. The diameters of the tablets are measured at time 0, 6 and 24 hours. All the coated tablets taken from the three formulations have the same coating weight gain of 8.3% w/w on the cores, but different PEG content. The content of PEG 8000 is 25%, 12.5 and 0%, for F-1, F-2 and F-3 respectively.

After absorbing the water through the pores of the film, the coated tablets expand. Expansion of the coated tablet is dimensionally restricted by the film. The lower the elasticity of film, the smaller the hydration diameter of the tablets. The lower the film strength, the shorter the film cracking or tablet burst time.

The results showed that the film from the F-3 formulation (0% PEG) burst in 24 hours. The results also showed that increasing the PEG 8000 content from 12.5% (the F-2 formulation) to 25% (the F-1 formulation), allowed for a greater tablet diameter upon hydration.

Further, the film composed of 12.5% PEG (the F-2 formulation) had the highest film strength. The film of the F-1 formulation (25% PEG) cracked in about 32 hours, but films of the F-2 formulation (12.5% PEG) were not broken in the same time.

TABLE 24

Data of film elasticity and strength test

| | Diameter of tablet (mm) | | |
|---|---|---|---|
| Time (hours) | F-1 (PEG 25%) | F-2 (PEG 12.5%) | F-3 (PEG 0%) |
| 0 | 9.5 | 9.5 | 9.5 |
| 6 | 12.3 | 11.5 | 11.5 |
| 24 | 17.2 | 15.7 | Burst |

EXAMPLE 5

Metformin HCl 750 mg ER (AQ) Tablet Cores

The following formulations were prepared for Metformin HCl ER (AQ) 750 mg tablet cores:

TABLE 25

Core formulation (Lot 1249-76)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 303.5 | 27.5 |
| Compritol ® 888 ATO | 22.4 | 2.00 |
| Total | 1120.0 | 100.00 |

TABLE 26

Core formulation (Lot 1249-77)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 29.4 | 2.63 |
| Compritol ® 888 ATO | 22.4 | 2.00 |
| Ac-Di-Sol ® (crosscarmelose sodium) | 274.1 | 24.47 |
| Total | 1120.0 | 100.00 |

TABLE 27

Core formulation (Lot 1249-78)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 29.4 | 2.63 |
| Compritol ® 888 ATO | 22.4 | 2.00 |
| Explotab ® NF (sodium starch glycolate) | 274.1 | 24.47 |
| Total | 1120.0 | 100.00 |

TABLE 28

Core formulation (Lot 1249-79)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 29.4 | 2.63 |
| Compritol ® 888 ATO | 22.4 | 2.00 |
| Xantural ® 180 | 274.1 | 24.47 |
| Total | 1120.0 | 100.00 |

TABLE 29

Core formulation (Lot 1249-80)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 29.4 | 2.63 |
| Compritol ® 888 ATO | 22.4 | 2.00 |
| Pharmacoat ® 606G (USP HPMC 2910) | 274.1 | 24.47 |
| Total | 1120.0 | 100.00 |

TABLE 30

Core formulation (Lot 1249-81)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 29.4 | 2.63 |
| Compritol ® 888 ATO | 22.4 | 2.00 |
| L-HPC | 274.1 | 24.47 |
| Total | 1120.0 | 100.00 |

TABLE 31

Core formulation (Lot 1249-86)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 29.4 | 2.63 |
| Compritol ® 888 ATO | 22.4 | 2.00 |
| Lactose 315 | 162.1 | 14.47 |
| Explotab ® NF (sodium starch glycolate) | 112.0 | 10.0 |
| Total | 1120.0 | 100.00 |

TABLE 32

Core formulation (Lot 1249-88)

| Ingredients | Mg/Tablet | % w/w |
|---|---|---|
| Metformin HCl | 750.0 | 66.96 |
| Aerosil ® 200 | 18.6 | 1.66 |
| Polyvinyl Alcohol | 25.5 | 2.28 |
| Kollidon ® CL | 141.1 | 12.63 |
| Compritol ® 888 ATO | 22.4 | 2.00 |
| Lactose ® 315 | 162.1 | 14.47 |
| Total | 1120.0 | 100.00 |

Controlled Release Coating

The following controlled release coating formulation was prepared for Metformin HCl ER (AQ) 750 mg tablets as well as for Metformin HCl ER (AQ) 1000 mg tablets:

TABLE 33

Controlled Release Coating Formulation

| Ingredients | % w/w |
|---|---|
| Eudragit ® NE 30D | 26.87 |
| Talc 400 | 4.03 |
| Titanium Dioxide | 0.77 |
| Pharmacoat ® 606 | 2.82 |
| PEG 8000 | 2.02 |
| Simethicone Emulsion | 0.20 |
| Polysorbate 80 | 0.10 |
| Purified Water | 63.19 |
| Total | 100.00 |

EXAMPLE 6

Dissolution Data of Metformin HCl 750 mg (AQ) and Metformin HCl 1000 mg (AQ) ER Coated Tablets in Water and in MSGF (pH 1.2)

Dissolution tests were carried out with Metformin HCl 750 mg ER (AQ) coated tablets and with Metformin HCl 1000 mg ER (AQ) coated tablets, to measure the drug release rate in water and in simulated gastric fluid (pH 1.2).
Apparatus: USP <711> Apparatus 1 (Baskets, 40 mesh), 100 RPM, 37.0±0.5° C.
Media: 900 ml water, and 900 ml modified simulated gastric fluid (msgf) pH 1.2
Sample times: 1, 2, 4, 6, 8, 10 and 12 hours
Analysis: A HPLC system, at wavelength of 210 nm

TABLE 34

Dissolution Data of Metformin HCl Coated Tablets

| Time (hr) | MET HCl 750 mg 1249-85-50-NEC- (27% Kollidon CL)- Msgf-100 rpm | MET HCl 750 mg 1249-85-50-NEC (27% Kollidon CL)- Water | MET HCl ER 1000 mg- Bio26400603 (3.5% Kollidon CL)- Water | MET HCl ER 1000 mg- Bio26400603 (3.5% Kollidon CL)- Msgf-100 rpm |
|---|---|---|---|---|
| 0 | 0 | 0 | 0 | 0 |
| 1 | 18 | 20 | 20 | 20 |
| 2 | 38 | 38 | 36 | 36 |
| 4 | 63 | 61 | 63 | 63 |
| 6 | 79 | 79 | 83 | 83 |
| 8 | 91 | 91 | 94 | 93 |
| 10 | 100 | 97 | 99 | — |
| 12 | 105 | 100 | 100 | 100 |

The tests showed that the coated tablets presented similar dissolution profiles in water as well as in simulated gastric fluid (pH 1.2).

EXAMPLE 7

Metformin HCl 1000 mg ER (AQ) Tablets

The following formulations were prepared for Metformin HCl ER (AQ) 1000 mg tablets:

TABLE 35

Core formulation (Lot 1249-90)

| Ingredients | Mg/Tablet | % w/w |
|---|---|---|
| Metformin Hydrochloride | 1000.0 | 83.33 |
| Aerosil ® 200 | 25.4 | 2.12 |
| Polyvinyl Alcohol | 34 | 2.83 |
| Kollidon ® CL | 116.6 | 9.72 |
| Compritol ® 888 ATO | 24 | 2.00 |
| Total | 1200.0 | 100.00 |

TABLE 36

Metformin HCl 1000 mg ER (AQ) Tablet formulation (dry solids only)

| Ingredient | Mg/Tablet | % of Tablet |
|---|---|---|
| Metformin Hydrochloride | 1000 | 76.336 |
| Colloidal Silicon Dioxide (Aerosil ® 200) | 25.4 | 1.939 |
| Polyvinyl Alcohol | 34.0 | 2.595 |
| Crospovidone (Kollidon ® CL) | 116.6 | 8.901 |
| Glyceryl Behenate (Compritol ® 888ATO) | 24.0 | 1.832 |
| Eudragit ® NE 30D (as dry) | 40.312 | 3.077 |
| Hypromellose (Pharmacoat ® 606) | 16.125 | 1.231 |
| Talc 400 | 18.142 | 1.385 |
| Polyethylene Glycol (PEG) 8000 | 10.078 | 0.769 |
| Titanium Dioxide | 3.853 | 0.294 |
| Simethicone Emulsion | 1.006 | 0.077 |
| Polysorbate 80 | 0.484 | 0.037 |
| Opadry ® II White | 20.0 | 1.527 |
| Total | 1310.0 | 100.0 |

EXAMPLE 8

Coating Formulation

Metformin HCl 1000 mg ER (AQ) Tablets

The following coating formulation was prepared for Metformin HCl ER (AQ) 1000 mg tablets:

TABLE 37

Coating formulation

| Ingredient | % w/w in Dry Solids | % in Suspension |
|---|---|---|
| Eudragit ® NE 30D (as dry) | 44.792 | 8.063 |
| Hypromellose (Pharmacoat ® 606) | 17.916 | 3.225 |
| Polyethylene Glycol (PEG) 8000 | 11.198 | 2.016 |
| Talc 400 | 20.158 | 3.628 |
| Titanium Dioxide | 4.280 | 0.770 |
| Simethicone Emulsion | 1.118 | 0.201 |
| Polysorbate 80 | 0.538 | 0.097 |
| Total Dry Solids | 100.00 | 18.000 |
| Water | — | 82.000 |
| Total | — | 100.000 |

The tablet cores are coated with three coating levels at dry solids 50 mg, 60 mg and 70 mg per tablet. The cores were compressed using Tooling C (Old oval shape), which was used for MET HCl 1000 mg ER, (Solvent based, PharmaPass™).

TABLE 38

The coating formulations with different weight gains

| Ingredient | Lot 1249-96-50-NEC-Old oval (mg/tablet) | Lot 1249-96-60-NEC-Old oval (mg/tablet) | Lot 1249-96-70-NEC-Old oval (mg/tablet) |
|---|---|---|---|
| Eudragit ® NE 30D (dry) | 22.396 | 26.875 | 31.354 |
| Pharmacoat ® 606 | 8.958 | 10.75 | 12.542 |
| PEG 8000 | 5.599 | 6.719 | 7.838 |
| Talc 400 | 10.079 | 12.095 | 14.11 |
| Titanium Dioxide | 2.14 | 2.569 | 2.997 |
| Simethicone Emulsion | 0.559 | 0.67 | 0.783 |
| Polysorbate 80 | 0.269 | 0.322 | 0.376 |
| Total Dry Solids | 50.000 | 60.000 | 70.000 |
| Water | 227.778 | 273.334 | 318.89 |
| Total | 277.778 | 333.34 | 388.89 |
| Core tablet weight | 1200 | 1200 | 1200 |
| % (w/w) Weight gain on the core tablet | 4.167 | 5.000 | 5.833 |

The drug release profiles of the above samples were compared to drug release profiles of Metformin HCl 1000 ER tablets (solvent based, PharmaPass™) and the Metformin HCl 500 ER tablets (Depomed™ product). The dissolution was performed using the following method: Apparatus: USP <711>, Apparatus II (Paddles), 50 RPM, 37.0±0.5° C.;
Medium: DI water, 900 ml
Sample Times: 1, 2, 3, 4, 5, 6, 7, 8, 9, 10, 11, 12, 13, 14, 15 and 16 hours Analysis: An automatically UV-Vis spectrophotometer system, at analytical wavelength of 240 nm.

The dissolution results show that the drug release rates of MET HCl 1000 mg ER (AQ) tablets of the three coating levels are similar, and only slightly affected by the coating weight gains. These coating formulations provide a targeted slower drug release rate than the Metformin HCl 1000 ER tablets (solvent base, PharmaPass™): the average values are about 6%, 7% and 8% slower in 12 hours, for 50 mg, 60 mg and 70 mg coating weight gain, respectively.

TABLE 39

The dissolution data of MET HCl 1000 mg (AQ) coated tablets (% drug released)

| Time (hr) | MET HCl 1000 mg-Bio26390503 (Old oval-Solvent Pharma Pass ™) | MET HCl 1000 mg (AQ)-1249-96-50-NEC-Old oval | MET HCl 1000 mg (AQ)-1249-96-60-NEC-Old oval | MET HCl 1000 mg (AQ)-1249-96-70-NEC-Old oval |
|---|---|---|---|---|
| 0 | 0 | 0 | 0 | 0 |
| 1 | 20 | 19 | 18 | 17 |
| 2 | 36 | 35 | 33 | 32 |
| 3 | 51 | 47 | 46 | 44 |
| 4 | 63 | 58 | 56 | 53 |
| 5 | 74 | 66 | 66 | 63 |
| 6 | 83 | 74 | 73 | 72 |
| 7 | 89 | 79 | 79 | 79 |
| 8 | 94 | 84 | 84 | 83 |
| 9 | 97 | 87 | 88 | 87 |
| 10 | 99 | 90 | 91 | 91 |
| 11 | 100 | 93 | 93 | 93 |
| 12 | 101 | 95 | 95 | 95 |
| 13 | 101 | 96 | 96 | 96 |
| 14 | 101 | 97 | 97 | 97 |
| 15 | 101 | 98 | 98 | 98 |
| 16 | 101 | 99 | 99 | 99 |

EXAMPLE 9

Process Description

Metformin HCl 1000 mg ER (AQ) Tablets

Step 1: Wet Granulation Process:

Delump Metformin HCl API using the milling machine (e.g. Fitzmill® M5A) with an appropriate screen (e.g. from about 6 Mesh to about 30 Mesh; preferably about 20-Mesh screen), and at a speed of from about 1800 to about 4500 rpm, preferably about 3400 rpm to about 3600 rpm. The granulation solution is heated and prepared in a stainless steel container with a mixer. The Purified Water is mixed with the Polyvinyl Alcohol (PVA). The PVA water solution is prepared at a temperature of from about 50° C. to about 90° C., preferably about 70° C. to about 80° C. When the PVA is completely dissolved and the solution is cooled, it is passed through a screen (e.g. from about 20-Mesh to about 40-Mesh, preferably from about 25-Mesh to about 30-Mesh screen) to remove any agglomerates. Metformin HCl API is placed with the Aerosil® 200 in the fluid bed granulator/dryer product container. The granulation solution is top-sprayed to form the Metformin HCl granules. During the processing, the inlet temperature is set at from about 63° C. to about 83° C. to maintain a product temperature of from about 40° C. to about 50° C. After spraying the granulation solution, the inlet temperature is adjusted to a temperature of from about 30° C. to about 40° C. (preferably about 35° C.). Once the inlet temperature drops to a temperature of from about 30° C. to about 40° C. (preferably about 35° C.), the granules are then dried at a temperature of from about 30° C. to about 40° C. (preferably about 35° C.) for about 20 minutes. The formed granules are then sieved with an appropriate screen (from about 12-Mesh to about 30-Mesh, preferably about a 20-Mesh screen)

| Major Process Parameters of Granulation | |
|---|---|
| Parameters | Ranges |
| Total Air Volume | 800-1650 CFM |
| Process Air Volume | 600-1500 CFM |
| Inlet Air Temperature | 73 ± 10° C. |
| Inlet Dew Point Temperature | 7 ± 3° C. |
| Exhaust Air Temperature | 45 ± 10° C. |
| Product Temperature | 45 ± 5° C. |
| Spray Rate | 190 ± 20 g/min. |
| Filter Shake Duration | 10 seconds |
| Filter Shake Interval | 30 seconds |
| Atomization Air Pressure | 4.5-5.5 Bar |
| Atomization Purge Pressure | 1.0 Bar |
| Spray Pump | 10% |

Step 2: Blend and Compression Processes:

Metformin HCl granules are loaded into a V-blender (e.g. 10 ft$^3$ or 20 ft$^3$ V-blender) with the Aerosil® 200 and mixed for about two (2) minutes. Kollidon® CL is added to the V-blender and the materials are mixed for about five (5) additional minutes. The Compritol® 888 is finally added to the V-blender and the materials are mixed for about five (5) minutes. Material is discharged and compressed into tablets using a tablet press (e.g. Courtoy® R190 tablet press; or Killian T300). Compression speed can be between 20,000-55,000 tablets per hour.

Step 3: Coating and Curing Process:

Pharmacoat® 606, Simethicone Emulsion, Polysorbate 80, and PEG 8000 are added/dissolved in separate portions of Purified Water. Talc 400, Titanium Dioxide, the Simethicone Emulsion dispersion and Polysorbate 80 solution mixes are added to the PEG 8000 solution and mixed, and added into the Pharmacoat® 606 solution while mixing. This suspension is then mixed with Eudragit® NE30D to form the final coating suspension. The suspension is filtered (using a screen of from about 30-Mesh to about 60-Mesh, preferably a 60-Mesh screen) and is stirred continuously through the coating process. The Metformin HCl 1000 mg uncoated tablets are loaded into an appropriately sized vented coating pan (from about 12" to about 60" diameter, preferably from about 15" to about 36" diameter coating pan, O'Hara® or equivalent). The coating suspension is sprayed onto the tablets in the coating pan which is equipped with spray nozzle(s) (e.g. three spray nozzles having from about 0.5 mm to about 1.5 mm, preferably about 1.0 mm openings) until the theoretical amount of suspension calculated is sprayed. The nozzles/pumping system is then rinsed with Purified Water to clean the system in preparation for over coating. Opadry® II (white) is mixed with Purified Water to form overcoat suspension and then sprayed onto tablets until the theoretical amount of suspension calculated is sprayed. The coated tablets are first dried in the pan, then "cured" by jogging the pan at the specified increased inlet temperature for the specified time period. The coated tablets can also be cured using an oven (e.g. Metro® C199 Series Insulated Heated Cabinet) at, for example, from about 60° C. to about 66° C. for about 3 hours.

TABLE 40

| Coating Process Parameters | |
|---|---|
| Process parameters | Range |
| Inlet Temperature (° C.) | SV: 40 ± 5 |
|  | PV: 40 ± 10 |
| Exhaust Temperature (° C.) | 30-40 |
| Product Temperature (° C.) | 27-35 |
| DP Differential Pressure (IN. W.C.) | −0.1 to −0.12 |
| Supply Air Flow (CFM) | 200 ± 50 |
| Pan Speed (rpm) | 3-8 |
| Atomizing Air (psi) | 20-24 |
| Pattern Air (psi) | 18-22 |
| Spraying Rate (g/min) | 5.0-15.0 |
| Angle of gun | 30-50° |
| Gun distance (cm) | 10-15 |

Step 4: Printing Process:

The coated tablets are loaded into the Tablet Printer hopper and printed with the strength and logo.

EXAMPLE 10

Dissolution of Uncoated Core Tablets

Metformin HCl 1000 mg

The dissolution data (see below) showed that the drug release was more than 90% w/w in 10 minutes and reached about 100% in 20 minutes. The batch size is 65 kg. The data represents average of beginning, middle, and end tablets.

The dissolution was performed using the following method:

Apparatus: USP <711>, Apparatus I (Baskets, 40 mesh), 100 RPM, 37.0±0.5° C.;

Medium: Modified Simulated Gastric Fluid (mSGF), USP, 900 ml

Analysis: A HPLC system, at wavelength 210 nm

The compression results indicated that the compression process is stable and all samples of core tablets from beginning, middle, and end of process have similar characteristics in chemical and physical results.

TABLE 41

| Specification | | |
|---|---|---|
|  | Target | Range |
| Tablet Weight (g) | 1.200 | ±5% for individual (1.140-1.260) |
|  |  | ±3% for average of 10 tablets |
|  |  | (1.164-1.236) |
| Tablet Hardness (Kp) | 14.0 | 10-16 |
| Friability (% w/w) | n/a | <0.8% |

TABLE 42

| Content Uniformity of Uncoated Tablets of MET HCl 1000 mg | | | |
|---|---|---|---|
|  | % Label claim (Lot 27140404) | | |
| Sample | Begin | Middle | End |
| 1 | 100.74 | 99.44 | 103.10 |
| 2 | 101.15 | 100.72 | 101.59 |
| 3 | 102.63 | 100.92 | 100.03 |
| 4 | 101.61 | 100.19 | 101.17 |
| 5 | 99.69 | 100.64 | 101.61 |
| 6 | 100.97 | 100.36 | 100.51 |

TABLE 42-continued

Content Uniformity of Uncoated Tablets of MET HCl 1000 mg

| | % Label claim (Lot 27140404) | | |
|---|---|---|---|
| Sample | Begin | Middle | End |
| 7 | 101.35 | 101.34 | 100.97 |
| 8 | 101.36 | 101.64 | 101.60 |
| 9 | 100.73 | 101.19 | 101.30 |
| 10 | 100.20 | 101.34 | 101.70 |
| Mean | 101.04 | 100.78 | 101.36 |
| Max | 102.63 | 101.64 | 103.10 |
| Min | 99.69 | 99.44 | 100.03 |
| % RSD | 0.79 | 0.65 | 0.81 |

TABLE 43

Physical characteristics of uncoated tablets of MET HCl 1000 mg (Lot 27140404)

| Tests | | Begin | Middle | End |
|---|---|---|---|---|
| Moisture % | | 0.50 | 0.60 | 0.60 |
| Friability % | | 0.06 | 0.06 | 0.02 |
| Hardness (kp) | Mean | 15.3 | 15.6 | 15.5 |
| | Min | 13.3 | 13.7 | 13.6 |
| | Max | 16.5 | 17.1 | 17.1 |
| Weight Variation (mg) | Mean | 1205 | 1202 | 1210 |
| | Min | 1191 | 1183 | 1192 |
| | Max | 1226 | 1226 | 1228 |
| | MinDiff | 1.20% | 1.60% | 1.50% |
| | MaxDiff | 1.70% | 2.00% | 1.50% |
| | % RSD | 0.84% | 0.93% | 0.81% |

TABLE 44

Dissolution data of uncoated core tablets of MET HCl 1000 mg (Lot 27140404)

| Time (min) | Bio-27140404-Beginning | Bio-27140404-Middle | Bio-27140404-End |
|---|---|---|---|
| 0 | 0 | 0 | 0 |
| 5 | 90 | 77 | 84 |
| 10 | 98 | 95 | 97 |
| 15 | 100 | 99 | 102 |
| 20 | 101 | 101 | 103 |
| 30 | 101 | 101 | 103 |
| 45 | 101 | 102 | 103 |
| 60 | 101 | 102 | 103 |

TABLE 45

Dissolution data comparison of uncoated core tablets of MET HCl 1000 mg (Average, n = 6)

| Time (min) | Bio-27140404 (Large oval shape) | Bio-27610105 (Wide large oval shape) | Bio-27640105 (Wide large oval shape) | Bio-27670105 (Wide large oval shape) |
|---|---|---|---|---|
| 0 | 0 | 0 | 0 | 0 |
| 10 | 97 | 98 | 95 | 99 |
| 20 | 100 | 101 | 101 | 102 |
| 30 | 102 | 102 | 102 | 101 |
| 45 | 102 | 102 | 102 | 102 |
| 60 | 102 | 102 | 102 | 102 |
| 120 | 102 | 102 | 102 | 102 |

EXAMPLE 11

Dissolution of Coated Tablets

Metformin HCl 1000 mg ER (AQ)

The dissolution data showed that three batches, Lot 1249-102-60, Lot 1249-107-60 and Lot 1249-109-60 have very similar dissolution profiles in mSGF and in water.

The dissolution in mSGF was performed using the following method:
Apparatus: USP <711>, Apparatus I (Baskets, 40 mesh), 100 RPM, 37.0±0.5° C.;
Medium: mSGF, USP, 900 ml
Analysis: A HPLC system, at wavelength 210 nm The dissolution in water was performed using the following method:
Apparatus: USP <711>, Apparatus II (Paddles), 50 RPM, 37.0±0.5° C.;
Medium: DI water, 900 ml
Analysis: An automatically UV-Vis spectrophotometer system, at analytical wavelength of 240 nm.

TABLE 46

Dissolution profiles of Metformin HCl 1000 mg ER(AQ) coated tablets in mSGF

| Time (hr) | MET HCl 1000 mg-1249-102-60-NEC | Std Dev | Min | Max | MET HCl 1000 mg-1249-107-60-NEC | Std Dev | Min | Max | MET HCl 1000 mg-1249-109-60-NEC | Std Dev | Min | Max |
|---|---|---|---|---|---|---|---|---|---|---|---|---|
| 0 | 0 | 0 | 0 | 0 | 0 | 0 | 0 | 0 | 0 | 0 | 0 | 0 |
| 1 | — | — | — | — | 15 | 2 | 12 | 16 | 17 | 1 | 15 | 18 |
| 2 | 29 | 2 | 25 | 31 | 27 | 2 | 24 | 31 | 29 | 2 | 27 | 33 |
| 4 | 51 | 3 | 45 | 54 | 49 | 3 | 44 | 54 | 52 | 4 | 48 | 59 |
| 6 | — | — | — | — | 65 | 3 | 63 | 70 | 68 | 4 | 64 | 76 |
| 8 | 80 | 3 | 75 | 83 | 77 | 4 | 71 | 84 | 78 | 4 | 74 | 85 |
| 10 | — | — | — | — | 85 | 2 | 83 | 89 | 84 | 3 | 80 | 88 |
| 12 | 94 | 3 | 89 | 97 | 91 | 2 | 88 | 94 | 89 | 3 | 86 | 94 |
| 14 | — | — | — | — | 95 | 2 | 93 | 99 | 92 | 2 | 90 | 94 |
| 16 | — | — | — | — | 96 | 3 | 90 | 98 | 94 | 2 | 92 | 96 |

TABLE 47

Dissolution profiles of Metformin HCl 1000 mg ER(AQ) coated tablets in water

| Time (hr) | MET HCl 1000 mg 1249-102-60-NEC | Min | Max | Std Dev | MET HCl 1000 mg-1249-107-60-NEC | Min | Max | Std Dev | MET HCl 1000 mg-1249-109-60-NEC | Min | Max | Std Dev |
|---|---|---|---|---|---|---|---|---|---|---|---|---|
| 0 | 0 | 0 | 0 | 0 | 0 | 0 | 0 | 0 | 0 | 0 | 0 | 0 |
| 1 | 19 | 18 | 22 | 2 | 19 | 15 | 20 | 2 | 20 | 15 | 23 | 3 |
| 2 | 35 | 32 | 39 | 2 | 33 | 29 | 35 | 2 | 35 | 29 | 39 | 4 |
| 3 | 48 | 45 | 52 | 3 | 45 | 41 | 47 | 2 | 47 | 41 | 51 | 4 |
| 4 | 59 | 56 | 63 | 3 | 55 | 52 | 56 | 2 | 58 | 53 | 61 | 4 |
| 5 | 68 | 66 | 72 | 2 | 64 | 62 | 66 | 2 | 67 | 61 | 70 | 4 |
| 6 | 75 | 73 | 79 | 2 | 71 | 68 | 73 | 2 | 72 | 65 | 77 | 5 |
| 7 | 81 | 79 | 85 | 3 | 76 | 69 | 78 | 4 | 78 | 72 | 83 | 4 |
| 8 | 86 | 84 | 90 | 2 | 82 | 79 | 84 | 2 | 83 | 78 | 88 | 4 |
| 9 | 90 | 88 | 93 | 2 | 86 | 84 | 88 | 1 | 87 | 83 | 91 | 3 |
| 10 | 93 | 91 | 96 | 2 | 90 | 88 | 91 | 1 | 87 | 70 | 94 | 9 |
| 11 | 96 | 94 | 98 | 2 | 92 | 90 | 93 | 1 | 91 | 78 | 96 | 7 |
| 12 | 97 | 95 | 100 | 2 | 95 | 94 | 95 | 1 | 93 | 85 | 98 | 5 |
| 13 | 98 | 94 | 101 | 2 | 97 | 96 | 97 | 1 | 92 | 67 | 99 | 12 |
| 14 | 100 | 97 | 103 | 2 | 96 | 88 | 98 | 4 | 95 | 82 | 100 | 7 |
| 15 | 101 | 98 | 104 | 2 | 99 | 98 | 100 | 1 | 98 | 93 | 101 | 3 |
| 16 | 102 | 98 | 105 | 2 | 98 | 87 | 100 | 5 | 98 | 90 | 102 | 4 |

EXAMPLE 12

Dissolution of Coated Tablets

Metformin HCl 1000 mg ER (AQ)

The dissolution in mSGF was performed using the following method:

Apparatus: USP <711>, Apparatus I (Baskets, 40 mesh), 100 RPM, 37.0±0.5° C.;

Medium: mSGF, USP, 900 ml

Analysis: A HPLC system, at wavelength 210 nm

TABLE 48

Dissolution data of feasible final formulations

| Time (hr) | MET HCl 1000 mg ER (AQ) Bio 27170504 (n = 12) | MET HCl 1000 mg ER (AQ) Target (5% slower than Biobatch) | MET HCl 1000 mg-1263-62-90-NEC-oven-3 h | MET HCl 1000 mg-1263-72-90-NEC-pan-2 h | MET HCl 1000 mg-1263-62-40-NEC-oven-3 h | MET HCl 1000 mg-1263-56-120-NEC-oven-3 h |
|---|---|---|---|---|---|---|
| 0 | 0 | 0 | 0 | 0 | 0 | 0 |
| 2 | 30 | 25 | 27 | 27 | 37 | 18 |
| 4 | 52 | 47 | 47 | 47 | 61 | 34 |
| 8 | 81 | 76 | 77 | 78 | 85 | 67 |
| 12 | 93 | 88 | 90 | 91 | 96 | 83 |

EXAMPLE 13

Coating Formulations

Influence of Coating Weight Gains on Drug Release

The biobatch (Lot MET HCl 1000 mg ER (AQ) Bio 27170504) has a coating weight gain of 60 mg per tablet. The influence of coating weight gains on the drug release is investigated using different coating weight gains from 40 to 120 mg per tablet. The coating formulations have the same composition but different weight gains.

The core tablets used for further study are produced using the same formulation, tooling (Large oval shape) and processes as the core tablets used for the previous biobatch.

The different weight gains are sampled and cured using an oven at about 63±3.0° C. for about 3 hours. The samples cured by oven are used for the investigation of influence of weight gain on drug release. The remaining final coated tablets are used for curing studies in coating pans.

TABLE 49

Coating formulation with different weight gains

| Ingredient | Mg/tablet | | | | | | | |
|---|---|---|---|---|---|---|---|---|
| Eudragit ® NE 30D (dry) | 17.916 | 22.396 | 26.875 | 31.354 | 35.833 | 40.312 | 44.791 | 53.75 |
| Pharmacoat ® 606 | 7.167 | 8.958 | 10.75 | 12.542 | 14.333 | 16.125 | 17.916 | 21.5 |
| PEG 8000 | 4.48 | 5.599 | 6.719 | 7.838 | 8.958 | 10.078 | 11.198 | 13.437 |
| Talc 400 | 8.063 | 10.079 | 12.095 | 14.11 | 16.127 | 18.142 | 20.158 | 24.19 |
| Titanium Dioxide | 1.712 | 2.14 | 2.569 | 2.997 | 3.425 | 3.853 | 4.281 | 5.137 |
| Simethicone Emulsion | 0.447 | 0.559 | 0.67 | 0.783 | 0.894 | 1.006 | 1.118 | 1.341 |
| Polysorbate 80 | 0.215 | 0.269 | 0.322 | 0.376 | 0.43 | 0.484 | 0.538 | 0.645 |
| Film total dry solids | 40.000 | 50.000 | 60.000 | 70.000 | 80.000 | 90.000 | 100.000 | 120.000 |

The coating processes were scaled up from 2.3 kg (Bio-batch 27170504) to 10 kg, 40 kg and up to 50 kg. The experimental batches are listed in the table below. The coating process parameters are also listed below for 24" coating pan and for the 36" coating pan.

TABLE 50

Experimental batches of coating study

| Lot No. | Batch size (kg) | Weight gain (mg) | Coating pan size (inches) | Curing study |
|---|---|---|---|---|
| Lot 1263-51-(50-80) | 10.0 | 50, 60 and 80 | 24 | Oven and coating pan |
| Lot 1263-56-(40-120) | 40.0 | 40, 60, 80, 100 and 120 | 36 | Oven and coating pan |
| Lot 1263-62-(40-100) | 50.0 | 40, 60, 80, 90, and 100 | 36 | Oven and coating pan |
| Lot 1263-72-(40-100) | 50.0 | 60, 80 and 90 | 36 | Oven and coating pan |

TABLE 51

Coating process parameters

| Process Parameters | 24" coating pan | 36" coating pan |
|---|---|---|
| Inlet Temperature (° C.) | SV: 40 ± 5 PV: 40 ± 10 | SV: 40 ± 10 |
| Exhaust Temperature (° C.) | 35 ± 5 | 35 ± 5 |
| Product Temperature (° C.) | 27-35 | 27-35 |
| DP Differential Pressure (IN. W.C.) | −0.1 to −0.12 | −0.1 to −0.12 |
| Supply Air Flow (CFM) | 300 ± 100 | 800 ± 100 |
| Pan Speed (rpm) | 3-8 | 3-8 |
| Atomizing Air (psi) | 20-25 | 30-32 |
| Pattern Air (psi) | 18-22 | 20-22 |
| Spraying Rate (g/min) | 35 ± 5 | 125 ± 25 |
| Angle of gun (°) | 30-50 | 30-50 |
| Gun distance (cm) | 10-15 | 10-15 |

The dissolution data showed that all the dissolution profiles from the different batches are very similar. The standard deviations are less than 4 in all cases.

TABLE 52

Dissolution data of scale-up reproducibility
(USP <711>, Apparatus 1, Baskets 40 mesh, 100 RPM, 37.0 ± 0.5° C., mSGF, USP, 900 ml)

| Time (hr) | MET HCl 1000 mg ER (AQ) Bio 27170504 (n = 12)-2.3 kg | MET HCl 1000 mg 1263-51-60-NEC-oven-3 h-10 kg | Std Dev | Min | Max | MET HCl 1000 mg 1263-56-60-NEC-oven-3 h-40 Kg | Std Dev | Min | Max |
|---|---|---|---|---|---|---|---|---|---|
| 0 | 0 | 0 | 0 | 0 | 0 | 0 | 0 | 0 | 0 |
| 2 | 30 | 28 | 3 | 25 | 33 | 29 | 1 | 27 | 30 |
| 4 | 52 | 48 | 4 | 44 | 52 | 48 | 2 | 46 | 52 |
| 8 | 81 | 77 | 3 | 73 | 80 | 75 | 3 | 71 | 79 |
| 12 | 93 | 90 | 3 | 86 | 93 | 88 | 2 | 85 | 91 |

TABLE 53

Dissolution data of scale-up reproducibility
(USP <711>, Apparatus 1, Baskets 40 mesh, 100 RPM,
37.0 ± 0.5° C., mSGF, USP, 900 ml)

| Time (hr) | MET HCl 1000 mg 1263-62-60-NEC-oven-3 h-50 kg | Std Dev | Min | Max | MET HCl 1000 mg 1263-72-60-NEC-oven-3 h-50 kg | Std Dev | Min | Max |
|---|---|---|---|---|---|---|---|---|
| 0 | 0 | 0 | 0 | 0 | 0 | 0 | 0 | 0 |
| 2 | 33 | 2 | 30 | 35 | 31 | 3 | 28 | 34 |
| 4 | 54 | 3 | 49 | 57 | 53 | 3 | 48 | 57 |
| 8 | 81 | 4 | 74 | 85 | 82 | 3 | 78 | 86 |
| 12 | 93 | 3 | 88 | 96 | 94 | 3 | 89 | 97 |

The influence of the coating weight gain on drug release was evaluated. The results showed that drug release could be adjusted using different weight gains from 40 to 120 mg dry solids per tablets. The drug release profiles are very similar for the weight gains from 60, 70 and 80 mg per tablets. (see tables below)

TABLE 54

Dissolution data of different coating weight gains
(USP <711>, Apparatus 1, Baskets 40 mesh, 100 RPM, 37.0 ± 0.5° C., mSGF, USP, 900 ml)

| Time (hr) | MET HCl 1000 mg ER (AQ) Bio 27170504 (n = 12) | MET HCl 1000 mg-1263-56-40-NEC-oven-3 h | MET HCl 1000 mg-1263-51-50-NEC-oven 3 h | MET HCl 1000 mg-1263-56-60-NEC-oven-3 h | MET HCl 1000 mg 1263-51-70-NEC-oven-3 h | MET HCl 1000 mg 1263-56-80-NEC-oven-3 h | MET HCl 1000 mg-1263-72-90-NEC-oven-3 h | MET HCl 1000 mg-1263-56-100-NEC-oven-3 h | MET HCl 1000 mg-1263-56-120-NEC-oven-3 h |
|---|---|---|---|---|---|---|---|---|---|
| 0 | 0 | 0 | 0 | 0 | 0 | 0 | 0 | 0 | 0 |
| 2 | 30 | 39 | 33 | 29 | 28 | 26 | 22 | 22 | 18 |
| 4 | 52 | 59 | 53 | 48 | 49 | 45 | 40 | 40 | 34 |
| 8 | 81 | 82 | 82 | 75 | 79 | 73 | 75 | 69 | 67 |
| 12 | 93 | 93 | 94 | 88 | 90 | 86 | 90 | 84 | 83 |

TABLE 55

Dissolution data of different coating weight gains
(USP <711>, Apparatus 1, Baskets 40 mesh, 100 RPM,
37.0 ± 0.5° C., mSGF, USP, 900 ml)

| Time (hr) | MET HCl 1000 mg-1263-51-60-NEC-oven-3 h | MET HCl 1000 mg 1263-51-70-NEC-oven-3 h | MET HCl 1000 mg 1263-51-80-NEC-oven-Mult.layer-3 h |
|---|---|---|---|
| 0 | 0 | 0 | 0 |
| 2 | 28 | 28 | 27 |
| 4 | 48 | 49 | 48 |
| 8 | 77 | 79 | 76 |
| 12 | 90 | 90 | 89 |

EXAMPLE 14

Overcoat Formulation

During curing, some coated tablets stuck together or stuck to the coating pan. The cosmetic over-coating (1-2% w/w) (formulation listed below) was found to help protect (i.e. reduce sticking) the functional coating of the tablets in pan curing process. The formulation with a 20 mg Opadry® II (85F18422) per tablet is used for the over-coating to have a uniform appearance.

TABLE 56

| Overcoat Formulation | |
|---|---|
| Ingredient | % w/w |
| Opadry ® II (85F18422) (dry) | 20.0 |
| Purified Water* | 80.0 |
| Total | 100.0 |

*Evaporated during coating process

Dissolution profiles of tablets without the Opadry® overcoat and tablets with the Opadry® overcoat were compared. The dissolution profile of the tablets without the Opadry® overcoat were very similar to that of the tablets with the Opadry® overcoat.

TABLE 57

Dissolution data of influence of the Opadry ® Overcoat (OP)
(USP <711>, Apparatus 1, Baskets 40 mesh, 100 RPM,
37.0 ± 0.5° C., mSGF, USP, 900 ml)

| Time (hr) | Lot # 1263-57-120-NEC-PAN-3 HOURS-without OP | Lot # 1263-61-120-NEC-OP-2%-PAN-3 HOURS | Lot # 1263-60-120-NEC-OP-1%-PAN-3 HOURS | Lot # 1263-60-120-NEC-OP-1%-OVEN-3 HOURS |
|---|---|---|---|---|
| 0 | 0 | 0 | 0 | 0 |
| 2 | 18 | 21 | 18 | 20 |
| 4 | 33 | 37 | 34 | 37 |
| 8 | 65 | 69 | 65 | 68 |
| 12 | 82 | 85 | 81 | 85 |

EXAMPLE 15

Curing

Metformin HCl 1000 mg ER (AQ) Tablets

Curing studies performed in an oven were compared to curing in a coating pan. The curing equipment and process parameters were investigated. The curing process was successfully scaled from 2 kg, to 10 kg and finally up to 50 kg, from oven to different size coating pans (see table below).

TABLE 58

Coating pan and the batch size used for curing study

| Coating Pan Size (inches) | Curing Batch Size (kg) |
|---|---|
| 15 | 2.0 |
| 24 | 10.0 |
| 36 | 40-50 |

The process parameters are listed in the tables below for the different steps. The steps included:
(i) Set the pan on jog mode at 5 on/600 off (seconds)
(ii) Prewarm the coated tablets to a product temperature of about 50° C.
(iii) Cure the coated tablets at a product temperature between about 50-59° C. for about one hour (see Table 59
(iv) Increase the product temperature to about 60° C., and cure the coated tablets at a product temperature between about 60-70° C. for about two hours (see Table 61
(v) Turn off the process heating (keeping all other process parameters the same), and cool the tablets for about 10 minutes.

TABLE 60

Curing process parameters for first one hour

| Parameters | U.O.M | Initial Setting |
|---|---|---|
| Process Air Volume | cfm | 400 ± 50 |
| Inlet Air Temperature | ° C. | SV: 62 ± 3 |
| Exhaust Temperature | ° C. | 50-59 |
| Product Temperature | ° C. | 50-59 |
| ΔP Differential Pressure | In. W.C. | −0.1 to −0.12 |
| Pan Speed | RPM | Jog |
| Jog Interval | Sec | 5 on/600 off |

TABLE 61

Curing process parameters for additional two hours

| Parameters | U.O.M | Initial Setting |
|---|---|---|
| Process Air Volume | cfm | 400 ± 50 |
| Inlet Air Temperature | ° C. | SV: 72 ± 3 |
| Exhaust Temperature | ° C. | 60-70 |
| Product Temperature | ° C. | 60-70 |
| ΔP Differential Pressure | In. W.C. | −0.1 to −0.12 |
| Pan Speed | RPM | Jog |
| Jog Interval | Sec | 5 on/600 off |

Curing in an oven was compared to curing with different size coating pans. The Lot 1263-62-90-NEC-oven was cured in an oven, and Lot 1263-72-90-NEC-pan and Lot 1236-75-NEC were cured in a pan. The dissolution data showed that the three batches had very similar dissolution profiles (see table below).

TABLE 62

Dissolution data of tablets cured in oven and tablets cured
with coating pans (% Drug Release)
(USP <711>, Apparatus 1, Baskets 40 mesh, 100 RPM,
37.0 ± 0.5° C., mSGF, USP, 900 ml)

| Time (hr) | MET HCl 1000 mg-1263-62-90-NEC-OVEN-3 h | MET HCl 1000 mg-1263-72-90-NEC-PAN-2 h | MET HCl 1000 mg-1236-75-NEC-PAN |
|---|---|---|---|
| 0 | 0 | 0 | 0 |
| 2 | 27 | 27 | 26 |
| 4 | 47 | 47 | 48 |
| 8 | 77 | 78 | 81 |
| 12 | 90 | 91 | 94 |

Coated tablets were cured in an oven and compared to coated tablets from the same lot cured in a 15 inch coating pan. The dissolution profiles were very similar.

TABLE 63

Influence of the Curing Equipment Dissolution data (% Drug Release)
(USP <711>, Apparatus 1, Baskets 40 mesh, 100 RPM,
37.0 ± 0.5° C., mSGF, USP, 900 ml)

| Time (hr) | MET HCl 1000 mg 1263-51-80-NEC-OVEN-Mult.layer-3 h | MET HCl 1000 mg 1263-53-80-NEC-PAN-3 h |
|---|---|---|
| 0 | 0 | 0 |
| 2 | 27 | 28 |
| 4 | 48 | 48 |
| 8 | 76 | 78 |
| 12 | 89 | 91 |

Lot "1263-56-120-NE-uncured" are uncured coated tablets and Lot "1263-56-120-NEC-oven-3h" are the same coated tablets but cured in oven at 63±3° C. for 3 hours. The results indicated that the curing process has a surprising and unexpected influence on the drug release (see table below). The cured tablets have a much slower drug release rate compared to the uncured tablets.

The dissolution profiles of the coated tablets cured between 1 and 3 hours were very similar.

TABLE 64

Dissolution data - Influence of curing and the curing time
(% Drug Release)
(USP <711>, Apparatus 1, Baskets 40 mesh, 100 RPM,
37.0 ± 0.5° C., mSGF, USP, 900 ml)

| Time (HR) | MET HCl 1000 mg-1263-56-120-NEC-oven-3 h | MET HCl 1000 mg 1263-56-120-NEC-UNCURED | MET HCl 1000 mg 1263-53-80-NEC-PAN-1 h | MET HCl 1000 mg 1263-53-80-NEC-PAN-1.5 h | MET HCl 1000 mg 1263-53-80-NEC-PAN-2 h | MET HCl 1000 mg 1263-53-80-NEC-PAN-2.5 h | MET HCl 1000 mg 1263-53-80-NEC-PAN-3 h |
|---|---|---|---|---|---|---|---|
| 0 | 0 | 0 | 0 | 0 | 0 | 0 | 0 |
| 2 | 18 | 101 | 25 | 29 | 28 | 29 | 28 |
| 4 | 34 | 101 | 46 | 50 | 49 | 50 | 48 |
| 8 | 67 | 101 | 76 | 78 | 76 | 78 | 78 |
| 12 | 83 | 100 | 91 | 92 | 90 | 90 | 91 |

Curing conditions were compared. Coated tablets were spread on trays in one layer or multiple layers. The dissolution profiles of the coated tablets that were cured while spread on the tray in one layer were very similar to the coated tablets that were cured while spread in multiple layers.

TABLE 65

Influence of Curing Condition Dissolution data (% Drug Release)
(USP <711>, Apparatus 1, Baskets 40 mesh, 100 RPM,
37.0 ± 0.5° C., mSGF, USP, 900 ml)

| Time (hr) | MET HCl 1000 mg 1263-51-80-NEC-OVEN-Mult.layer-3 h | MET HCl 1000 mg 1263-51-80-NEC-OVEN-1 layer-3 h |
|---|---|---|
| 0 | 0 | 0 |
| 2 | 27 | 25 |
| 4 | 48 | 45 |
| 8 | 76 | 75 |
| 12 | 89 | 88 |

Cured tablets with "wrinkles" ("bubbles") were compared to cured tablets without such "wrinkles" (or bubbles). "Wrinkles (or bubbles)" were observed on the surfaces of cured tablets in early pan curing trials. This was attributed to the dynamic movement of the coated tablets during the pan curing process. "Wrinkles (or bubbles)" were eliminated when reducing the dynamic movement of tablets by setting the pan mode at "Jog on" for 5 seconds and "Jog off" for 10 minutes during a 3 hour curing process [by a lower temperature (55-59° C.) curing for 1 hour and following a higher temperature (60-70° C.) curing for 2 hours]. The cosmetic over-coat may have added a protective layer to avoid this frictional effect as well. The dissolution profiles of the cured tablets having "wrinkles (or bubbles)" were found to be very similar to that of the cured tablets without such "wrinkles" (or bubbles).

TABLE 66

Influence of "Wrinkles" (or "Bubbles") Dissolution data
(% Drug Release)
(USP <711>, Apparatus 1, Baskets 40 mesh, 100 RPM,
37.0 ± 0.5° C., mSGF, USP, 900 ml)

| Time (hr) | MET HCl 1000 mg 1263-51-80-NEC-Pan-3 h-without bubble | MET HCl 1000 mg 1263-51-80-NEC-Pan-3 h-with bubble |
|---|---|---|
| 0 | 0 | 0 |
| 2 | 25 | 26 |
| 4 | 46 | 46 |
| 8 | 73 | 73 |
| 12 | 88 | 88 |

EXAMPLE 16

Stability Studies

Metformin HCl 1000 mg ER (AQ) Tablets

Stability studies were carried out at the following conditions:

Apparatus: USP <711> Apparatus 1 (Baskets, 40 mesh), 100 RPM, 37.0+0.5° C.

Medium: Modified simulated gastric fluid (mSGF), pH 1.2, USP, 900 ml

Sample times: 2, 4, 8 and 12 hours

Analysis: A HPLC system, at wavelength of 210 nm

The Metformin HCl 1000 mg ER (AQ) Tablets used were:

Lot #27840305B

Bottled Printed Tablets-30CT

Storage Condition: 25° C./60% RH

The data indicates that the product had good stability at 24 months. The dissolution data is summarized in the table below.

TABLE 67

Dissolution data as % dissolved (standard deviation) - Stability
in 24 months
Metformin HCl 1000 mg ER (AQ) Tablets (Lot #27840305B)
(USP <711>, Apparatus 1, Baskets 40 mesh, 100 RPM,
37.0 ± 0.5° C., mSGF, USP, 900 ml)

| TIME (HR) | INITIAL % (SD) | 3 MO % (SD) | 6 MO % (SD) | 9 MO % (SD) | 12 MO % (SD) | 18 MO % (SD) | 24 MO % (SD) |
|---|---|---|---|---|---|---|---|
| 2  | 26 (1) | 27 (2) | 26 (1) | 27 (1) | 26 (1) | 27 (1) | 27 (2) |
| 4  | 48 (2) | 48 (4) | 48 (2) | 49 (2) | 47 (2) | 48 (2) | 49 (2) |
| 8  | 80 (2) | 78 (2) | 78 (1) | 80 (2) | 78 (2) | 79 (4) | 81 (2) |
| 12 | 94 (2) | 92 (2) | 92 (2) | 94 (2) | 91 (2) | 93 (2) | 95 (1) |

Stability studies were also carried out at conditions of 25° C./60% RH and 40° C./75% RH. The stability data in 6 months indicates that the product has good stability in both conditions. The assay is 98.4-100.7% at 25° C./60% RH, and 99.1-101.4 at 40° C./75% RH. The impurities are lower than the limits. The dissolution data is summarized in the table below.

TABLE 68

Dissolution data of stability in 6 months (% drug released)
(USP <711>, Apparatus 1, Baskets 40 mesh, 100 RPM, 37.0 ± 0.5° C., mSGF, USP, 900 ml)

| Time (h) | MET HCl 1000 mg (AQ)- Bio 27170504- 0 M | MET HCl 1000 mg (AQ)- Bio 27170504- 1 M- 25° C./60% RH | MET HCl 1000 mg (AQ)- Bio 27170504- 3 M- 25° C./60% RH | MET HCl 1000 mg (AQ)- Bio 27170504- 6 M- 25° C./60% RH | MET HCl 1000 mg (AQ)- Bio 27170504- 1 M- 40° C./75% RH | MET HCl 1000 mg (AQ)- Bio 27170504- 3 M- 40° C./75% RH | MET HCl 1000 mg (AQ)- Bio 27170504- 6 M- 40° C./75% RH |
|---|---|---|---|---|---|---|---|
| 2  | 30 | 28 | 30 | 30 | 29 | 31 | 32 |
| 4  | 52 | 51 | 54 | 53 | 52 | 54 | 55 |
| 8  | 81 | 82 | 82 | 82 | 81 | 83 | 84 |
| 12 | 93 | 92 | 94 | 94 | 94 | 96 | 95 |

EXAMPLE 17

A Two-Way, Crossover, Open-Label, Single-Dose, Fed, Comparative Bioavailability Study of Metformin HCl ER (AQ) 1000 mg Tablets Versus Metformin HCl ER 2×500 Mg Tablets in Normal Healthy Non-Smoking Male and Female Subjects Study Design and Phase of Development: Two-way crossover, randomized, open-label, single-dose, fed, comparative bioavailability study Objectives: The objective of this study was to evaluate the dosage strength proportionality between two strengths of Metformin HCl ER Tablets by evaluating the relative peak and systemic exposure of the prototype Metformin HCl ER (AQ) 1000 mg Tablets against the Metformin HCl ER 500 mg Tablets given as 2×500 mg under single dose fed conditions.

Main Criteria for Inclusion: Normal, healthy, non-smoking male and female subjects within the age range of 18 to 55 years.

Test Product/Investigational Product, Lot Number and Mode of Administration: Following a fast of at least 4 hours, and 30 minutes after the start of a standardized dinner, 1 Metformin HCl ER (AQ) 1000 mg Tablet, Lot #: 27840305B (potency value=98.2% of label claim), administered orally with 240 mL of ambient temperature water.

Reference Product, Batch or Lot Number and Mode of Administration: Following a fast of at least 4 hours, and 30 minutes after the start of a standardized dinner, 2 Metformin HCl ER 500 mg Tablets, Lot #: PR-05-003CL (potency value=98.6% of label claim), administered orally with 240 mL of ambient temperature water.

Number of Subjects (planned and analyzed): There were 48 subjects dosed in Period I, 46 of whom completed the study. One subject was dismissed due to emesis within 24 hours of dosing and I subject was dismissed due to administrative reasons. Pharmacokinetic and statistical analyses were performed on 45 subjects who completed the study, as I subject vomited approximately 3 minutes after Period II dosing.

Blood Draw Timepoints: During each study period, 17 blood samples were collected from each subject at the following timepoints: 0.0 (pre-dose), 1.0, 2.0, 3.0, 4.0, 5.0, 6.0, 7.0, 8.0, 9.0, 10.0, 12.0, 16.0, 20.0, 24.0, 36.0, and 48.0 hours post-dose.

Criteria for Evaluation: The pharmacokinetic analysis was performed on 45 subjects who completed the 2 study periods, as I subject vomited approximately 3 minutes after Period II dosing. The safety assessment was performed on all subjects who received at least 1 dose during the course of the study.

Pharmacokinetics (PK): The following pharmacokinetic parameters for metformin were calculated by standard non-compartmental methods: $AUC_{0-t}$, $AUC_{0-inf}$, $C_{max}$, $T_{max}$, $K_{el}$, and $t_{1/2}$.

Safety: The incidences of all adverse events (AEs) were tabulated by treatment and subject number. Absolute values for laboratory parameters were documented and values outside their respective normal ranges were flagged. Absolute values for vital signs, electrocardiogram (ECG) parameters, laboratory parameters and physical examinations were also documented and values outside the normal range were flagged. Shifts from baseline values were tabulated. AEs were documented using investigator and Medical Dictionary for Regulatory Activities (MedDRA) terms.

Statistical Methods Using General Linear Model (GLM) procedures in Statistical Analysis System (SAS), analysis of variance (ANOVA) was performed on ln transformed $AUC_{0-t}$, $AUC_{0-inf}$ and $C_{max}$ and on untransformed $K_{el}$ and $t_{1/2}$ at the significance level of 0.05. The intra-subject coefficient of variation (CV) was calculated using the Mean Square Error (MSE) from the ANOVA table. The ratio of geometric means and the 90% geometric confidence interval (90% C.I.) were calculated based on the difference in the Least Squares Means of the ln transformed $AUC_{0-t}$, $AUC_{0-inf}$ and $C_{max}$ between the test and reference formulations. $T_{max}$ was analyzed using nonparametric methods.

Summary of Safety Results: No serious adverse events were reported. There were a total of 13 AEs reported by 22 subjects during the study. Three AEs were "possibly" related to the study drug.

TABLE 69

PHARMACOKINETIC PARAMETERS FOR METFORMIN

| Pharma-cokinetic Parameters | Metformin HCl ER (AQ) 1000 mg Tablets (A) (n = 45) | Metformin HCl ER 500 mg Tablets (B) (n = 45) |
|---|---|---|
| | Geometric Mean (% CV) Arithmetic Mean ± SD | |
| $AUC_{0-t}$ (ng · hr/mL) | 11312.91 (24.12) 11644.36 ± 2808.29 | 11588.86 (23.53) 11912.74 ± 2803.07 |
| $AUC_{0-inf}$ (ng · hr/mL) | 11481.59 (23.89) 11811.61 ± 2822.23 | 11752.25 (23.44) 12076.82 ± 2830.41 |
| $C_{max}$ (ng/mL) | 1209.91 (25.63) 1251.80 ± 320.88 | 1063.90 (25.79) 1099.42 ± 283.55 |
| $T_{max}$ (hr)* | 9.00 (6.02-12.00) | 8.00 (4.00-10.13) |
| $t_{1/2}$ (hr) | 7.94 ± 2.81 | 8.50 ± 3.17 |
| $K_{el}$ (hr−1) | 9.96E−02 ± 3.81E−02 | 9.54E−02 ± 4.10E−02 |

*median (min-max)

TABLE 70

BIOEQUIVALENCE ASSESSMENTS FOR METFORMIN

| Parameter | 90% C.I. | Ratio of Means | Intra-Subject CV |
|---|---|---|---|
| | Potency Uncorrected Data | | |
| $AUC_{0-t}$ | 94.10% to 101.31% | 97.64% | 10.41% |
| $AUC_{0-inf}$ | 94.17% to 101.38% | 97.71% | 10.41% |
| $C_{max}$ | 107.44% to 120.26% | 113.67% | 15.90% |

| Parameter | 90% C.I. | Ratio of Means |
|---|---|---|
| | Potency Uncorrected Data | |
| $AUC_{0-t}$ | 94.48% to 101.72% | 98.04% |
| $AUC_{0-inf}$ | 94.55% to 101.79% | 98.10% |
| $C_{max}$ | 107.87% to 120.75% | 114.13% |

The objective of this study was to evaluate the dosage strength proportionality between 2 strengths of Metformin HCl ER Tablets by evaluating the relative peak and systemic exposures of the prototype Metformin HCl ER (AQ) 1000 mg Tablets (Treatment A) against the Metformin HCl ER 500 mg Tablets given as 2×500 mg (Treatment B) under single dose fed conditions.

The statistical results indicated that the 90% confidence intervals of the geometric mean test/reference ratios for $AUC_{0-t}$, $AUC_{0-inf}$ and $C_{max}$ of metformin were within 80.00%-125.00%. The potency corrected data also had similar results.

Overall, Metformin HCl ER (AQ) 1000 mg Tablets (Treatment A) demonstrated equivalent peak and total systemic exposure to Metformin HCl ER 2×500 mg Tablets (Treatment B), under single-dose, fed administration conditions.

No SAEs were reported.

Overall, Metformin HCl ER (AQ) 1000 mg Tablets were well tolerated as a single-dose of 1000 mg, administered under fed conditions, and no significant safety issues emerged.

This study was performed in compliance with GCP.

EXAMPLE 18

A Two-Way Crossover, Open-Label, Single Dose, Fed, Comparative Bioavailability Study of Metformin HCl ER (AQ) 1000 mg Tablets Versus Glumetza™ Tablets (2×500 mg Once Daily) in Normal, Healthy, Non-Smoking Male and Female Subjects Study Design and Phase of Development: Two-way crossover, randomized, open-label, single-dose, fed, comparative bioavailability study Objectives: The objective of this study was to determine the rate and extent of absorption of metformin from a test formulation of Metformin HCl ER Aqueous (AQ) 1000 mg Tablets versus the reference Glumetza™ (Metformin HCl ER) 500 mg Tablets under fed conditions.

Main Criteria for Inclusion: Normal, healthy, non-smoking male and female subjects between the ages of 18 and 65 years.

Test Product/Investigational Product, Lot Number and Mode of Administration: Following a fast of at least 4 hours, and 30 minutes after the start of a standardized dinner, 1 Metformin HCl ER (AQ) 1000 mg Tablet, Lot #: PR-06-507CL (potency value=99.0% of label claim), administered orally with 240 mL of ambient temperature water.

Reference Product, Lot Number and Mode of Administration: Following a fast of at least 4 hours, and 30 minutes after the start of a standardized dinner, 2 Glumetza™ (Metformin HCl ER) 500 mg Tablets, Lot #: 06T10461A (potency value=98.9% of label claim), administered orally with 240 mL of ambient temperature water.

Number of Subjects (planned and analyzed): Forty-eight subjects were planned for this study. Two subjects were dismissed (pre-dose) because they did not complete the critical meal within the allotted time. There were 46 subjects dosed in Period I, 42 of whom completed the study. Two subjects were dismissed because of adverse events (AEs), 1 subject withdrew because of AEs, and 1 subject withdrew for personal reasons. Pharmacokinetic and statistical analyses were performed on the 42 subjects who completed the study.

Blood Draw Timepoints: During each study period, 17 blood samples were collected from each subject at the following timepoints: 0.00 (pre-dose), 1.00, 2.00, 3.00, 4.00, 5.00, 6.00, 7.00, 8.00, 9.00, 10.00, 12.00, 16.00, 20.00, 24.00, 36.00, and 48.00 hours post-dose.

Bioanalytical Procedure: Metformin and the internal standard, atenolol, were extracted by protein precipitation using acetonitrile into an organic medium from 0.10 mL of human plasma. An aliquot of this extract was injected into a High Performance Liquid Chromatography system and detected using a mass spectrometer. The analytes were separated by normal phase chromatography. Evaluation of the assay was carried out by the construction of an 8 point calibration curve (excluding zero concentration) covering the range of 10.006 ng/mL to 2001.120 ng/mL for metformin in human plasma. The slope and intercept of the calibration curves were determined through weighted linear regression analysis (1/conc.$^2$). Two calibration curves and duplicate QC samples (at three concentration levels) were analyzed along with each batch of the study samples. Peak area ratios were used to determine the concentration of the standards, quality control samples, and the unknown study samples from the calibration curves.

Criteria for Evaluation: The pharmacokinetic analysis was performed on 42 subjects who completed the 2 study periods. The safety assessment was performed on all subjects who received at least 1 dose during the course of the study.

Pharmacokinetics (PK): The following pharmacokinetic parameters for metformin were calculated by standard non-compartmental methods: $AUC_{0-t}$, $AUC_{0-inf}$, $C_{max}$, $T_{max}$, $K_{el}$, and $t_{1/2}$.

Safety: The incidences of all adverse events (AEs) were tabulated by treatment and subject number. Absolute values for vital signs, electrocardiogram (ECG) parameters, laboratory parameters and physical examinations were also documented and values outside the normal range were flagged. Shifts from baseline values were tabulated. AEs were documented using investigator and Medical Dictionary for Regulatory Activities (MedDRA) terms.

Statistical Methods Using General Linear Model (GLM) procedures in Statistical Analysis System (SAS), analysis of variance (ANOVA) was performed on ln transformed $AUC_{0-t}$, $AUC_{0-inf}$ and $C_{max}$ and on untransformed $K_{el}$ and $t_{1/2}$ at the significance level of 0.05. The intra-subject coefficient of variation (CV) was calculated using the Mean Square Error (MSE) from the ANOVA table. The ratio of geometric means and the 90% geometric confidence interval (90% C.I.) were calculated based on the difference in the Least Squares Means of the ln transformed $AUC_{0-t}$, $AUC_{0-inf}$ and $C_{max}$ between the test and reference formulations. $T_{max}$ was analyzed using nonparametric methods.

Summary of Safety Results: There were a total of 27 AEs reported by 13 subjects during the study. After treatment with Glumetza™ (Metformin HCl ER) 500 mg Tablets, the most frequent AEs were the following: diarrhea (13.3%), headache (13.3%), and loose stool (13.3%). No AE was experienced more than once after treatment with Metformin HCl ER (AQ) 1000 mg Tablets during the course of the study. At the end-of-study exam, the most frequent AEs were the following: white blood cell count increased (13.3%) and white blood cell urine positive (13.3%). Six AEs were "possibly" related to the study drug. All subjects who experienced AEs during this study recovered completely. No serious adverse events were reported.

TABLE 71

PHARMACOKINETIC PARAMETERS FOR METFORMIN

| Pharmacokinetic Parameters | Geometric Mean (% CV) Arithmetic Mean ± SD | |
|---|---|---|
| | Metformin HCl ER (AQ) 1000 mg Tablets; Lot #: PR-06-507CL (A; n = 42) | Glumetza ™ (Metformin HCl ER) 2 × 500 mg Tablets; Lot #: 06T10461A (B; n = 42) |
| $AUC_{0-t}$ (ng · hr/mL) | 11442.91 (21.52) 11706.34 ± 2519.78 | 12132.39 (20.80) 12408.23 ± 2580.78 |
| $AUC_{0-inf}$ (ng · hr/mL) | 11648.30 (21.17) 11906.50 ± 2521.06 | 12319.92 (20.77) 12598.84 ± 2616.35 |
| $C_{max}$ (ng/mL) | 1210.14 (21.88) 1238.00 ± 270.90 | 1086.21 (22.74) 1116.13 ± 253.77 |
| $T_{max}$ (hr)* | 10.00 (8.00-12.00) | 8.00 (4.00-10.00) |
| $t_{1/2}$ (hr) | 7.40 ± 3.08 | 7.46 ± 3.76 |
| $K_{el}$ (hr-1) | 1.09E-01 ± 4.06E-02 | 1.17E-01 ± 5.78E-02 |

*median (min-max)

TABLE 72

RELATIVE BIOAVAILABILITY ASSESSMENTS FOR METFORMIN

| | Potency Uncorrected Data | | |
|---|---|---|---|
| Parameter | 90% C.I. | Ratio of Means | Intra-Subject CV |
| $AUC_{0-t}$ | 91.28% to 97.72% | 94.45% | 9.28% |
| $AUC_{0-inf}$ | 91.60% to 97.84% | 94.67% | 8.97% |
| $C_{max}$ | 105.85% to 117.22% | 111.39% | 13.94% |

| | Potency Corrected Data | |
|---|---|---|
| Parameter | 90% C.I. | Ratio of Means |
| $AUC_{0-t}$ | 91.19% to 97.62% | 94.35% |
| $AUC_{0-inf}$ | 91.51% to 97.74% | 94.58% |
| $C_{max}$ | 105.74% to 117.10% | 111.28% |

The objective of this study was to determine the rate and extent of absorption of metformin a novel one daily ER formulation of Metformin HCl ER Aqueous (AQ) 1000 mg Tablets and compare to the reference formulation, Glumetza™ (Metformin HCl ER) 500 mg Tablets given as 2 tablets under single-dose fed conditions.

The results indicated that equivalent peak and systemic exposure of metformin were observed between the novel formulation of Metformin HCl ER Aqueous (AQ) 1000 mg Tablets and Glumetza™ (Metformin HCl ER) 500 mg Tablets given as 2×500 mg. The 90% geometric CI of the mean ratios of $C_{max}$ and AUCs were found to be within the 80.00%-125.00% range based on potency uncorrected results. The potency corrected results also demonstrated similar results.

In conclusion, the novel once daily formulation (Metformin HCl ER Aqueous (AQ) 1000 mg Tablets) demonstrated equivalent peak and systemic exposure when compared to Glumetza™ (Metformin HCl ER) 500 mg Tablets when given as 2 tablets under single-dose fed conditions.

No SAEs were reported. Metformin HCl ER (AQ) 1000 mg Tablets were well tolerated as a single-dose of 1000 mg, administered under fed conditions, and no significant safety issues emerged.

This study was performed in compliance with GCP.

EXAMPLE 19

Metformin HCl 500 mg tablets having the AQ controlled release coating of the present invention (Metformin AQ tablets) were compared with the commercial product Glumetza® (Metformin HCl 500 mg tablet), which is based on Acuform® technology (by Depomed®) described in, e.g., U.S. Pat. No. 6,340,475.

It is generally accepted that in order to achieve once-daily delivery of metformin HCl, the dosage form must be ingested under fed conditions. In addition, it is believed that the dosage form should be designed to allow delivery to the upper gastrointestinal tract, as is provided by gastro-retentive type systems. Both of these dosage forms (Metformin AQ tablet and the Glumetza® tablet) provide pharmacokinetic performance that supports sustained release once-daily dosing, but the two products use different technologies and mechanisms of drug release to achieve this. They also demonstrate hydration behavior under laboratory observation that support and help explain these differences.

The Acuform® technology of the Glumetza® tablet provides a sustained release gastric retention effect by using a hydrophilic matrix dosage form design. As a hydrophilic matrix design, the Glumetza® tablet contains sufficient water soluble/swellable polymers to provide gelation and an accompanying sustained release functionality on the drug. As an example, the Glumetza® 500 mg tablet, which is a once-daily product of metformin HCl, contains significant amounts of Polyethylene Oxide (PEO) and hypromellose (HPMC) as functional polymers in the tablet. Laboratory observations show that when this Glumetza® 500 mg tablet is placed in simulated gastric fluid at 37 degree C. to simulate physiologic conditions in the stomach, the dosage form hydrates and swells outward in an unrestricted manner. There is no functional coating on the product—only a cosmetic coating. In addition to the unrestricted hydrogel expansion, the Glumetza® tablet was observed to be very dense and sticky in the swollen state, residing on the bottom of the dissolution vessel during the testing.

The Metformin AQ 500 mg tablet is structured very differently from the Glumetza® 500 mg tablet. The Metformin AQ 500 mg tablet core is primarily drug, and contains only a small amount of polyvinyl alcohol as a granulating polymer, which does not function as a sustained release polymer. The delivery system therefore relies on a functional polymer coating to provide its sustained release effect. This would be classified as a reservoir system, as opposed to a hydrogel like the Glumetza® tablet. In addition to differences in drug release mechanism, it has been observed in laboratory tests that the Metformin AQ 500 mg tablet floats upon hydration, whereas the Glumetza® 500 mg tablet sinks. Differences in buoyancy can be a key differentiator in gastric retentive behavior, along with other variables (see Timmermans J. Floating Hydrophilic matrix dosage forms for oral use: Factors controlling their buoyancy and gastric residence capabilities. Doctor of Sciences Thesis, Universite Libre de Bruxelles, March 1991). It is apparent from these observations that the two products are dissimilar in their system performance characteristics.

Based on reviewed literature and laboratory observations, the Depomed® Acuform® system is best classified as a swellable hydrophilic matrix (see, e.g., Arora S., et al. Floating Drug Delivery Systems: A Review. AAPS PharmSciTech 2005; 6 (3) Article 47) meaning that it appears to have unrestricted hydrogel expansion and sedimentation characteristics. Laboratory tests of the Depomed® Acuform® (system observed that this formulation does not float in simulated gastric fluid and forms a dense sticky mass upon hydration. In contrast, the AQ system of the Metformin AQ tablet was observed to be a floating reservoir system (see, e.g., Arora S., et al. Floating Drug Delivery Systems: A Review. AAPS PharmSciTech 2005; 6 (3) Article 47). The AQ system does not rely on hydrogel formation within the tablet core. With the AQ system, drug release is mediated by an applied functional coating. Its hydrated expansion is restricted, unlike a hydrogel, with the functional coating retaining its integrity and acting to form a reservoir-based delivery system.

The invention claimed is:

1. A controlled release oral dosage form comprising:
   a) a core, wherein said core comprises:
      i) an effective amount of metformin hydrochloride, and
      ii) at least one first pharmaceutically acceptable excipients, and
   b) a stable controlled release monolithic coating surrounding the core,
   wherein said dosage form provides a $T_{max}$ of said metformin hydrochloride of from about 6 hours to about 12 hours after administration to a patient; and/or provides an in-vitro release rate of the metformin hydrochloride when tested by the USP Apparatus I (Basket Apparatus) method at 100 rpm, in 900 mL simulated gastric fluid and at about 37° C., such that not more than 37% of the metformin hydrochloride is released after about 2 hours and not more than 61% of the metformin hydrochloride is released after about 4 hours,
   wherein the stable controlled release coating hydrates when placed into water, and wherein the at least one first pharmaceutically acceptable excipient comprises cross-linked polyvinylpyrrolidone, and
   wherein the stable controlled release coating is formed by a process comprising:
   coating the core with a coating composition to form a coated core, and curing the coated core to form the stable controlled release coating, wherein the coating composition comprises
      i) an aqueous dispersion of a neutral ester copolymer without any functional groups;
      ii) a poly glycol having a melting point of at least about 55° C., and
      iii) one or more second pharmaceutically acceptable excipients; and wherein the curing is conducted at a temperature at least equal to or greater than the melting point of the poly glycol.

2. The controlled release oral dosage form of claim 1 wherein the effective amount of the metformin hydrochloride is about 1000 mg.

3. The controlled release oral dosage form of claim 1 wherein the dosage form floats when placed in an aqueous environment.

4. The controlled release oral dosage form of claim 1 wherein the dosage form expands when placed in an aqueous environment.

5. The controlled release oral dosage form of claim 1 wherein upon oral administration to a patient, an effective amount of the metformin hydrochloride is released into a region of the patient's upper gastrointestinal tract.

6. The controlled release oral dosage form of claim 1 wherein upon oral administration to a patient, the dosage form remains substantially intact until substantially all of the metformin hydrochloride is released.

7. The controlled release oral dosage form of claim 1 wherein the stable controlled release monolithic coating is formed by a process that excludes usage of an organic solvent.

8. The controlled release oral dosage form of claim 1, wherein the core further comprises at least one of colloidal silicon dioxide, polyvinyl alcohol, and glyceryl behenate.

9. The controlled release oral dosage form of claim 1, wherein the at least one second pharmaceutically acceptable excipient comprises at least one of hypromellose, talc, titanium dioxide, simethicone, and polysorbate 80.

10. The controlled release oral dosage form of claim 1, wherein the at least one second pharmaceutically acceptable excipient comprises at least one of an anti-tacking agent agent, an emulsifying agent agent, a hydrophilic agent, an antifoaming agent, a flavorant, a colorant, and a sweetener.

11. The controlled release oral dosage form of claim 1 wherein the aqueous dispersion of neutral ester copolymer without any functional groups comprises at least one of a 30% aqueous dispersion of a neutral copolymer based on ethyl acrylate and methacrylate, and a 40% aqueous dispersion of a neutral copolymer based on ethyl acrylate and methacrylate.

12. The controlled release oral dosage form of claim 1 wherein the poly glycol comprises at least one of polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, poloxamer 188, poloxamer 338, poloxamer 407, polyethylene oxides, polyoxyethylene alkyl ethers, polyoxyethylene sorbitan fatty acid esters, and polyoxyethylene stearates.

13. The controlled release oral dosage form of claim 1 wherein the curing is conducted for a time period of from about 1 to about 24 hours.

14. The controlled release oral dosage form of claim 1 wherein the curing is conducted for a time period of from about 1 to about 16 hours.

15. The controlled release oral dosage form of claim 1 wherein the curing is conducted for a time period of from about 2 to about 7 hours.

16. The controlled release oral dosage form of claim 1 wherein the curing is conducted for a time period of from about 4 to about 7 hours.

17. The controlled release oral dosage form of claim 1 wherein the curing is conducted for a time period of from about 2 to about 4 hours.

18. The controlled release oral dosage form of claim 1 wherein the curing is conducted for a time period of from about 1 to about 3 hours.

19. The controlled release oral dosage form of claim 1 wherein the curing is conducted at a temperature at least equal to or greater than about 60 degrees C.

20. A controlled release oral dosage form comprising:
   a) a core, wherein said core comprises:
      i) metformin hydrochloride, and
      ii) at least one first pharmaceutically acceptable excipient excipients, and
   b) a stable controlled release monolithic coating surrounding the core,
wherein said dosage form provides a $T_{max}$ of said metformin hydrochloride of from about 6 hours to about 12 hours after administration to a patient; and/or provides an in-vitro release rate of the metformin hydrochloride when tested by the USP Apparatus I (Basket Apparatus) method at 100 rpm, in 900 mL simulated gastric fluid and at about 37° C., such that nor more than 37% of the metformin hydrochloride is released after about 2 hours and not more than 61% of the metformin hydrochloride is released after about 4 hours,
wherein the stable controlled release coating hydrates when placed into water, and wherein the at least one first pharmaceutically acceptable excipient comprises cross-linked polyvinylpyrrolidone,
   wherein the stable controlled release monolithic coating is formed by a process comprising:
   coating the core with a coating composition to form a coated core, and curing the coated core to form the stable controlled release coating, wherein the coating composition comprises
      i) an ethyl acrylate and methyl methacrylate copolymer dispersion;
      ii) a poly glycol comprising at least one of polyethylene glycol 4000, polyethylene glycol 4600, polyethylene glycol 6000, polyethylene glycol 8000, polyethylene glycol 10000, polyethylene glycol 12000, polyethylene glycol 20000, and polyethylene glycol 35000, and
      iii) at least one second pharmaceutically acceptable excipient; and wherein the curing is conducted at a temperature at least equal to or greater than the melting point of the poly glycol, wherein the polyglycol has a melting point of at least about 55° C.

21. The controlled release oral dosage form of claim 20, wherein the effective amount of the metformin hydrochloride is about 1000mg.

22. The controlled release oral dosage form of claim 20, wherein the dosage form floats when placed in an aqueous environment.

23. The controlled release oral dosage form of claim 20, wherein the dosage form expands when placed in an aqueous environment.

24. The controlled release oral dosage form of claim 20, wherein upon oral administration to a patient, an effective amount of the metformin hydrochloride is released into a region of the patient's upper gastrointestinal tract.

25. The controlled release oral dosage form of claim 20, wherein upon oral administration to a patient, the dosage form remains substantially intact until substantially all of the metformin hydrochloride is released.

26. The controlled release oral dosage form of claim 20, wherein the stable controlled release monolithic coating is formed by a process that excludes usage of an organic solvent.

27. The controlled release oral dosage form of claim 20, wherein the core further comprises at least one of colloidal silicon dioxide, polyvinyl alcohol, and glyceryl behenate.

28. The controlled release oral dosage form of claim 20, wherein the one or more second pharmaceutically acceptable excipients comprises at least one of hypromellose, talc, titanium dioxide, simethicone, polysorbate 80, and a mixture thereof.

29. The controlled release oral dosage form of claim 20, wherein the one or more second pharmaceutically acceptable excipients comprises at least one of an anti-tacking agent agent, an emulsifying agent agent, a hydrophilic agent, an antifoaming agent, a flavorant, a colorant, a sweetener and a mixture thereof.

30. The controlled release oral dosage form of claim 20, wherein the ethyl acrylate and methyl methacrylate copolymer dispersion comprises at least one of a 30% aqueous dispersion of a neutral copolymer based on ethyl acrylate and methacrylate, and a 40% aqueous dispersion of a neutral copolymer based on ethyl acrylate and methacrylate.

31. The controlled release oral dosage form of claim 20, wherein the curing is conducted for a time period of from about 1 to about 24 hours.

32. The controlled release oral dosage form of claim 20, wherein the curing is conducted for a time period of from about 1 to about 16 hours.

33. The controlled release oral dosage form of claim 20, wherein the curing is conducted for a time period of from about 2 to about 7 hours.

34. The controlled release oral dosage form of claim 20, wherein the curing is conducted for a time period of from about 4 to about 7 hours.

35. The controlled release oral dosage form of claim 20, wherein the curing is conducted for a time period of from about 2 to about 4 hours.

36. The controlled release oral dosage form of claim 20, wherein the curing is conducted for a time period of from about 1 to about 3 hours.

37. The controlled release oral dosage form of claim 20, wherein the curing is conducted at a temperature at least equal to or greater than about 60 degrees C.

* * * * *